US008455542B2

(12) United States Patent
Kang et al.

(10) Patent No.: US 8,455,542 B2
(45) Date of Patent: Jun. 4, 2013

(54) BENZOFURAN TYPE DERIVATIVES, A COMPOSITION COMPRISING THE SAME FOR TREATING OR PREVENTING COGNITIVE DYSFUNCTION AND THE USE THEREOF

(75) Inventors: Dong Wook Kang, Seoul (KR); Jee Woo Lee, Seoul (KR); Young Ho Kim, Gyeonggi-do (KR); Hee Kim, Gyeonggi-do (KR); Hee Jin Ha, Gyeonggi-do (KR); Eun Joo Nam, Seoul (KR); Chan Mi Joung, Gyeonggi-do (KR)

(73) Assignees: Daewoong Pharmaceutical Co., Ltd., Gyeonggi-do (KR); Medifron DBT Co., Ltd., Seoul (KR)

( * ) Notice: Subject to any disclaimer, the term of this patent is extended or adjusted under 35 U.S.C. 154(b) by 0 days.

(21) Appl. No.: 13/489,263

(22) Filed: Jun. 5, 2012

(65) Prior Publication Data

US 2012/0259006 A1    Oct. 11, 2012

Related U.S. Application Data

(62) Division of application No. 12/443,972, filed as application No. PCT/KR2007/004833 on Oct. 2, 2007, now Pat. No. 8,263,649.

(30) Foreign Application Priority Data

Oct. 2, 2006    (KR) ................. 10-2006-0097388

(51) Int. Cl.
*A61K 31/34*        (2006.01)
*C07D 307/00*    (2006.01)
(52) U.S. Cl.
USPC .......................................... 514/469; 549/469
(58) Field of Classification Search
USPC .......................................... 514/469; 549/469
See application file for complete search history.

(56) References Cited

U.S. PATENT DOCUMENTS

| 4,304,785 | A | 12/1981 | Griengl |
| 5,854,282 | A | 12/1998 | Mellin |
| 2004/0223909 | A1 | 11/2004 | Montaito et al. |

OTHER PUBLICATIONS

Ennaceur and Delacour, A new one-trial trest for neurobiological studies of memories in rats. 1:Behavioral data, Behav. Brain Res., 31, pp. 47-59. 1988.
Gillardon, F. et al., Activation of c-Fos contributes to amyloid beta-peptide-induced neurotoxicity, Brain Research, 706 (1), pp. 169-172, 1996.
Janus et al., A-beta peptide immunization reduces behavioral impairment and plaques in a model of Alzheimer's disease, Nature, 408, pp. 979-982, 2000.
Lausen & Belknap, Intracerebroventricular injections in Mice, J. Pharmacol. Methods, 16 pp. 355-357, 1986.
Morgan et al., A-beta peptide vaccination prevents memory loss in an animal model of Alzheimer's disease, Nature, 408, pp. 982-985, 2000.
Morris, Developments of a water maze procedure for studying spatial learning in the rat, J. Neurosci. Methods., 11, pp. 47-60, 1984.
Practico et al., Increased lipid peroxidation precedes amyloid plaque formation in an animal model of Alzheimer amyloidosis, J. Neurosci, 21(12), pp. 4183-4187, 2001.
Sarter et al., Attention of scopolamine-induced impairment of spontaneous alternation behavior of antagonist but not inverse agonist and agonist beta-carbolines, Psychopharmacology, 94, pp. 491-495, 1998.
Song et al., Behavioral and Neuropathological changes induced by central injection of carboxyl-terminal fragment of beta-amyloid precursor protein in mice, J. Neurochem., 71, pp. 875-878, 1998.
Yu et al., Methyl analogues of the experimental Alzheimer drug phenserine: synthesis and structure/activity relationship for acetyl— and butyrylcholinesterase inhibitory action, J. Med. Chem., 44, pp. 4062-4071, 2001.
Schreiber, Fred, et al., 1976, Synthesis of Benzofuran Styrax Extractives, J. Chem. Soc., Perkin Trans., 1 (14): 1514-1518.
Irvine, GB, et al., 2008, Protein Aggregation in the Brain: The Molecular Basis for Alzheimer's and Parkinson's Diseases, Mol. Med., 14(7-8), 451-464.
Search Report, European Patent Office, Oct. 27, 2011, 6 pages.

*Primary Examiner* — Paul Zarek
(74) *Attorney, Agent, or Firm* — Hogan Lovells US LLP

(57) ABSTRACT

The present invention relates to the novel benzofuran derivatives, the preparation thereof and the composition comprising the same. The benzofuran derivatives of the present invention showed potent inhibiting activity of beta-amyloid aggregation and cell cytotoxicity resulting in stimulating the proliferation of neuronal cells as well as recovering activity of memory learning injury caused by neuronal cell injury using transformed animal model with beta-amyloid precursor gene, therefore the compounds can be useful in treating or preventing cognitive function disorder.

8 Claims, 15 Drawing Sheets

BENZOFURAN TYPE DERIVATIVES, A COMPOSITION COMPRISING THE SAME FOR TREATING OR PREVENTING COGNITIVE DYSFUNCTION AND THE USE THEREOF

TECHNICAL FIELD

The present invention relates to novel benzofuran type derivatives, a composition comprising the same having preventing and treating activity of cognitive dysfunction disease and the use thereof.

BACKGROUND ART

CNS (Central Nervous System) consisting of brain and spinal cord which plays a main role in regulating life phenomenon is a essential organ governing all the human function through from sensory and (in)voluntary movement to thinking, memory, motion, language etc. Accordingly, a rapidly progressed apoptosis of neuronal cell caused by stroke, trauma etc as well as slowly progressed apoptosis such as degenerative disease occurring in CNS caused by senile dementia for example, Alzheimer's disease or Parkinson disease etc result in irreversible functional disorder of neuronal network, which give rise to immortal failure of human function in the end. Among them, the patients suffering from Alzheimer disease, a representative senile dementia have been increased in proportion to both of extended life-span and modernized welfare facility. According to the public survey of Korea Institute for Health and Social Affair, the ratio of older people among Korean people exceeds 7% in 2000, reaches to 8.3% (3,970,000) and shall approach to 14.4% in 2019. Especially, the ratio of more than 65 years old patient suffering with senile dementia is presumed to 8.2% in Korea. In Western countries, about 10% among more than 65 years old and about 40-50% among 80 years old patient suffers with senile dementia. Since more than five million patients suffer with the disease, the medical expense caused thereby is presumed to hundred billion dollars in a year. There have been found that more than about two hundred thousand people are suffering from dementia in Korea. In America, it has been presumed the number of the patients be increased to two fold than the number of present patients in 2030 and fourteen million (more than 350%) in 2050.

Since Alzheimer's disease initiated with cognitive function disorder is one of long-term degenerative diseases resulting in the breakdown of human nature, there have been tried to develop effective and preventive drugs till now, for example, acetylcholineesterase inhibitor such as Aricept® (Pfizer Co.), Exelon (Novartis Co.), Reiminyl® (Janssen Co.) or NMDA receptor antagonist such as Ebixa (Lundbeck Co.). However, the acetylcholine esterase inhibitor could just alleviate reduced cognitive ability and could not satisfactorily treat etiological cause of the disease. Although the drug shows temporarily alleviated effect on only some of patients (about 40-50%), it could not maintain it's potency for a long time moreover it shows various adverse response such as hepatotoxicity, vomiting, anorexia in case of long-term treatment. Accordingly, there has been urgently needed to develop new therapeutic agent to prevent and treat the disease nowadays. Many multi-national pharmaceutical companies have been invested on the development in a large scale and in particular, focused in the development for beta- or gamma secretase inhibitor reducing the reproduced amount of beta-amyloid consisting of about 40 amino acids which has been presumed to be an etiological factor of Alzheimer disease. The basic study on the Alzheimer disease has been actively attempted in Korea however the development of Alzheimer treating agent has been merely progressed till now. Since there have been found in animal model test as well as clinical trial that the development of gamma secretase inhibitor is associated with considerable toxicity, it has been proved to be not recommendable whereas the development of beta secretase inhibitor is recommendable as proven by gene deficiency transformed animal model test. It is also regarded as a safe tool to focus on targeting the factors involved in beta amyloid aggregation. There has been reported that 'phenserine' developed by Axonyx Co. in USA has been progressed in Clinical trial 2 phase and it shows dual activities of inhibiting cholinesterase as well as beta amyloid aggregation. (Greig et al., *J. Med. Chem.*, 44, pp. 4062-4071, 2001; www.medicalnewstoday.com; www.alzforum.org/drg/drc)

The development of vaccine using beta amyloid has been known as another possible method. There has been reported that the serial study on the vaccine progressed by Elan Co. failed because of its un-predictable adverse response such as encephalitis during clinical trial. However, it has been reported that beta amyloid vaccine could alleviate cognitive function in animal model test and improve the activity of brain cell as well as damaged brain neuronal cells, resulting in alleviating Alzheimer syndrome. (Janus et al., *Nature*, 408, pp. 979-982, 2000; Morgan et al., *Nature*, 408, pp. 982-985, 2000)

To investigate novel benzofuran derivatives having potent inhibiting effect on cognitive function disorder through already well-known screening tests, the inventors of the present invention have intensively screened various benzofuran derivatives showing potent inhibiting activity of beta-amyloid aggregation and memory learning recovery study using passive avoidance test etc, and finally completed present invention by confirming that the benzofuran derivatives inhibits beta-amyloid aggregation and cell cytotoxicity resulting in stimulating the proliferation of neuronal cells as well as recovers memory learning injury caused by neuronal cell injury.

These and other objects of the present invention will become apparent from the detailed disclosure of the present invention provided hereinafter.

DISCLOSURE

Technical Problem

The present invention provides novel benzofuran derivatives and the pharmacologically acceptable salt thereof showing potent inhibiting effect on cognitive function disorder.

The present invention also provides a pharmaceutical composition comprising novel benzofuran derivatives and the pharmacologically acceptable salt thereof as an active ingredient in an effective amount to treat and prevent cognitive function disorder.

The present invention also provides a use of novel benzofuran derivatives and the pharmacologically acceptable salt thereof for the preparation of pharmaceutical composition to treat and prevent cognitive function disorder.

The present invention also provides a method of treating or preventing cognitive function disorder in a mammal comprising administering to said mammal an effective amount of novel benzofuran derivatives and the pharmacologically acceptable salt thereof, together with a pharmaceutically acceptable carrier thereof.

The present invention also provides a health functional food comprising novel benzofuran derivatives for the prevention or alleviation of cognitive function disorder.

Technical Solution

The present invention provides a novel compound represented by the following general formula (I), and the pharmaceutically acceptable salt thereof:

[Chemical Formula 1]

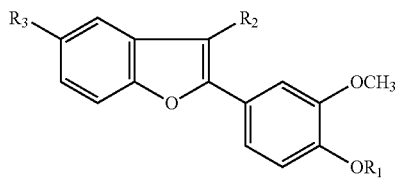
(I)

wherein $R_1$ is at least one selected from the group consisting of a hydrogen atom, $C_1$-$C_6$ alkyl group, $C_2$-$C_6$ alkyl ketone group and —($CH_2$)n-Q, of which Q is an ether group or amine group substituted with $C_1$-$C_6$ lower alkyl group;

$R_2$ is a hydrogen atom, or an ether group or thio group substituted with $C_1$-$C_6$ alkyl group;

$R_3$ is a group selected from following substituents of general formula (Ia), (Ib), (Ic) or (Id),

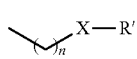
(Ia)

wherein R' is a hydrogen atom, or $C_1$-$C_6$ alkyl group,

X is at least one selected from amine group unsubstituted or substituted with O, S or R", of which R" is a benzyl group substituted with ester group or carboxyl group, n is an integer of 0-9;

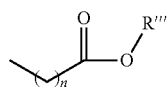
(Ib)

wherein R'" is at least one selected from a hydrogen atom, $C_1$-$C_6$ alkyl group or benzyl group, n is an integer of 0-9;

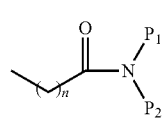
(Ic)

wherein $P_1$, $P_2$ is independently, at least one selected from the group consisting of a hydrogen atom, $C_1$-$C_6$ alkyl group, phenyl group, benzyl group and 2-methyl-3-acetamide group, n is an integer of 0-9;

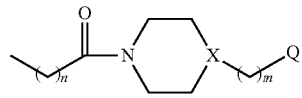
(Id)

wherein X is C, O, S or N atom,
m is an integer of 0 or 1,
Q is a phenyl group substituted with $C_1$-$C_3$ alkyl group, halogen atom, or nitro group,
n is an integer of 0-9.

As preferable compounds of general formula (I), the compounds of the present invention wherein $R_1$ is a methyl group, ethyl group, methylketone group or ethyl ketone group; Q is a methoxy group, an ethoxy group, dimethylamino group or diethylamino group; $R_2$ is a hydrogen atom or methylthio group; $R_3$ is selected from the group of general formula (Ia) wherein X is an oxygen atom or an ester group substituted with benzyl group; a group of general formula (Ib) wherein R'" is a methyl group, an ethyl group or a benzyl group; a group of general formula (Ic) wherein $P_1$, $P_2$ is independently a methyl group, an ethyl group, a dimethyl group, diethyl group or 2-methyl-3-acetamide group; a group of general formula (Id) wherein Q is a phenyl group substituted with a methyl group or an ethyl group are more preferable.

The most preferred compound of general formula (I) is one selected from the group consisting of;

Among the group of general formula (Ia),
3-[2-(4'-hydroxy-3'-methoxyphenyl)-3-(methylthio)-benzofuran-5-yl]-1-propanol,
2-methoxy-4-[5-(3-methoxy-propyl)-3-methylsulfanyl-benzofuran-2-yl]-1-phenol,
2-[2-(4'-hydroxy-3'-methoxyphenyl)-3-(methylthio)-benzofuran-5-yl]-1-ethanol,
2-methoxy-4-[5-(2-methoxy-ethyl)-3-methylsulfanyl-benzofuran-2-yl]-phenol,
3-[2-(4'-hydroxy-3'-methoxyphenyl)-benzofuran-5-yl]-1-propanol,
2-methoxy-4-[5-(3-methoxy-propyl)-benzofuran-2-yl]-phenol,
2-[2-(4'-hydroxy-3'-methoxyphenyl)-benzofuran-5-yl]-1-ethanol,
3-[2-(3,4-dimethoxyphenyl)-3-methylsufanyl-benzofuran-5-yl]-propan-1-ol,
2-(3,4-dimethoxyphenyl)-5-(3-methoxy-propyl)-3-methylsufanyl-benzofuran,
2-[2-(3,4-dimethoxyphenyl)-3-methylsufanyl-benzofuran-5-yl]-ethanol,
2-(3,4-dimethoxyphenyl)-5-(2-methoxy-ethyl)-3-methylsufanyl-benzofuran,
3-[2-(3,4-dimethoxy-phenyl)-benzofuran-5-yl]-propan-1-ol,
2-(3,4-dimethoxy-phenyl)-5-(3-methoxy-propyl)-benzofuran,
2-[2-(3,4-dimethoxy-phenyl)-benzofuran-5-yl]-ethanol,
2-(3,4-dimethoxy-phenyl)-5-(2-methoxy-ethyl)-benzofuran,
3-[2-{4'-[3-(diethylamino)propoxy]-3'-methoxy-phenyl}-3-(methylthio)-benzofuran-5-yl]-1-propanol,
2-(3-methoxy-4-methoxymethoxy-phenyl)-5-(3-methoxy-propyl)-3-methylsulfanyl-benzofuran,
5-(2-methoxy-ethyl)-2-(3-methoxy-4-methoxymethoxy-phenyl)-3-methylsulfanyl-benzofuran,
3-[2-{4'-[3-(diethylamino)propoxy]-3'-methoxy-phenyl}-benzofuran-5-yl]-1-propanol,
3-[2-{4'-hydroxy-3'-methoxy-phenyl}-3-(methylthio)-benzofuran-5-yl]-propylamine, Benzyl N-3-[2-{4'-hydroxy-3'-methoxyphenyl}-3-(methylthio)-benzofuran-5-yl]-propylcarbamate,
2-[2-{4'-hydroxy-3'-methoxy-phenyl}-3-(methylthio)-benzofuran-5-yl]-ethylamine,
Benzyl N-2-[2-{4'-hydroxy-3'-methoxyphenyl}-3-(methylthio)-benzofuran-5-yl]-ethylcarbamate,
2-(2-(3,4-Dimethoxyphenyl)-3-(methylthio)benzofuran-5-yl)propanoic acid,
5-Allyloxy-2-(3,4-dimethoxy-phenyl)-benzofuran,
2-(3,4-dimethoxyphenyl)-N-propylbenzofuran-5-amine,
2-(3,4-Dimethoxy-phenyl)-5-propoxy-benzofuran;
Among the group of general formula (Ib),
Methyl 3-[2-(4'-hydroxy-3'-methoxyphenyl)-3-(methylthio)-benzofuran-5-yl]-propionate,
Benzyl 2-[2-(4'-hydroxy-3'-methoxyphenyl)-3-(methylthio)-benzofuran-5-yl]-propionate,
3-[2-(4'-hydroxy-3'-methoxyphenyl)-3-(methylthio)-benzofuran-5-yl]-propionic acid,
Methyl 2-[2-(4'-hydroxy-3'-methoxyphenyl)-3-(methylthio)-benzofuran-5-yl]-acetate,
Benzyl 2-[2-(4'-hydroxy-3'-methoxyphenyl)-3-(methylthio)-benzofuran-5-yl]-acetate,
2-[2-(4' hydroxy-3' methoxyphenyl)-3-(methylthio)-benzofuran-5-yl]acetic acid,
[2-(3,4-dimethoxyphenyl)-benzofuran-5-yl]acetic acid,
3-[2-(4' hydroxy-3-(methoxyphenyl)-benzofuran-5-yl]propionic acid,
Methyl 2-[2-(4' hydroxy-3'-methoxyphenyl)-benzofuran-5-yl]acetate,
2-[2-(4'-hydroxy-3'-methoxyphenyl)-benzofuran-5-yl]acetic acid,
3-[2-(3,4-dimethoxyphenyl)-3-methylsufanyl-benzofuran-5-yl]-propionic acid,
3-[2-(3,4-dimethoxyphenyl)-3-methylsufanyl-benzofuran-5-yl]-propionic acid methyl ester,
[2-(3,4-dimethoxyphenyl)-3-methylsulfanyl-benzofuran-5-yl]acetic acid,
[2-(3,4-dimethoxyphenyl)-3-methylsulfanyl-benzofuran-5-yl]acetic acid methyl ester,
3-[2-(3,4-dimethoxy-phenyl)-benzofuran-5-yl]-propionic acid,
3-[2-(3,4-dimethoxy-phenyl)-benzofuran-5-yl]-propionic acid methyl ester,
[2-(3,4-dimethoxyphenyl)-benzofuran-5-yl]acetic acid methyl ester,
Methyl 3-[2-(4'-acetoxy-3'-methoxyphenyl)-3-(methylthio)-benzofuran-5-yl]-propionate,
Methyl 2-[2-(4'-acetyloxy-3'-methoxyphenyl)-3-(methylthio)-benzofuran-5-yl]-acetate,
Methyl 3-[2-(4'-{4-[3-(diethylamino)propoxy]-3'-methoxyphenyl}-3-(methylthio)-benzofuran-5-yl]-1-propionate,
Methyl 2-[4-(acetyloxy)-3-methoxyphenyl]-1-benzofuran-5-yl-acetate,
Methyl 3-[2-(4'-acetoxy-3'-methoxyphenyl)-benzofuran-5-yl]propionate,
Methyl 3-[2-{4'-[3-(diethylamino)propoxy]-3'-methoxyphenyl}-benzofuran-5-yl]-1-propionate,
Methyl 2-(2-(4-acetoxy-3-methoxyphenyl)-3-(methylthio)benzofuran-5-yl)propanoate,
Methyl 2-(2-(4-acetoxy-3-methoxyphenyl)benzofuran-5-yl)propanoate;
Among the group of general formula (Ic),
N,N-diethyl 3-[2-(4'-hydroxy-3'-methoxyphenyl)-3-(methylthio)-benzofuran-5-yl]-propionamide,
N,N-dimethyl 3-[2-(4'-hydroxy-3'-methoxyphenyl)-3-(methylthio)-benzofuran-5-yl]-propionamide,
N-methyl 3-[2-(4'-hydroxy-3'-methoxyphenyl)-3-(methylthio)-benzofuran-5-yl]-propionamide,
N,N-diethyl 2-[2-(4'-hydroxy-3'-methoxyphenyl)-3-(methylthio)-benzofuran-5-yl]-acetamide,
N,N-dimethyl 2-[2-(4'-hydroxy-3'-methoxyphenyl)-3-(methylthio)-benzofuran-5-yl]-acetamide,
N-methyl 2-[2-(4'-hydroxy-3'-methoxyphenyl)-3-(methylthio)-benzofuran-5-yl]-acetamide,
(R)-2-(2-(2-(4-hydroxy-3-methoxyphenyl)-3-(methylthio)-benzofuran-5-yl]-acetamide-4-methylpentanamide,
N-phenyl 3-[2-(4'-hydroxy-3'-methoxyphenyl)-3-(methylthio)-benzofuran-5-yl]-propionamide,
N-benzyl 3-[2-(4'-hydroxy-3'-methoxyphenyl)-3-(methylthio)-benzofuran-5-yl]-propionamide,
(R)-3-(2-[2-(4-hydroxy-3-methoxyphenyl)-3-(methylsulfanyl)-1-benzofuran-5-yl]-acetylamino-4-methylpentanamide,
N-phenyl 2-[2-(4'-hydroxy-3'-methoxyphenyl)-3-(methylthio)-benzofuran-5-yl]-acetamide,
N-benzyl 2-[2-(4'-hydroxy-3'-methoxyphenyl)-3-(methylthio)-benzofuran-5-yl]-acetamide,
2-[2-(4'-hydroxy-3'-methoxyphenyl)-3-(methylthio)-benzofuran-5-yl]acetamide,
3-[2-(4'-hydroxy-3'-methoxyphenyl)-3-(methylthio)-benzofuran-5-yl]propionamide,
3-(2-(4-Hydroxy-3-methoxyphenyl)-3-(methylthio)benzofuran-5-yl)-N,N-dipropylpropanamide,
3-(2-(3,4-Dimethoxyphenyl)-3-(methylthio)benzofuran-5-yl)-N,N-dipropylpropanamide,
2-(2-(4-Hydroxy-3-methoxyphenyl)-3-(methylthio)benzofuran-5-yl)-N,N-dimethylacetamide,
N,N-Diethyl-2-(2-(4-hydroxy-3-methoxyphenyl)-3-(methylthio)benzofuran-5-yl)propanamide,
2-(2-(3,4-Dimethoxyphenyl)-3-(methylthio)benzofuran-5-yl)-N-propylacetamide,
N,N-Diethyl-3-(2-(3,4-dimethoxyphenyl)benzofuran-5-yl)propanamide,
N,N-Diethyl-2-(2-(4-hydroxy-3-methoxyphenyl)benzofuran-5-yl)acetamide,
2-(2-(4-Hydroxy-3-methoxyphenyl)benzofuran-5-yl)-N,N-dipropylacetamide,
N,N-Diethyl-2-(2-(4-hydroxy-3-methoxyphenyl)benzofuran-5-yl)propanamide,
2-(2-(4-Hydroxy-3-methoxyphenyl)benzofuran-5-yl)-N,N-dimethylpropanamide,
2-(2-(4-Hydroxy-3-methoxyphenyl)benzofuran-5-yl)-N,N-dipropylpropanamide,
2-(2-(4-Hydroxy-3-methoxyphenyl)benzofuran-5-yl)-N-propylpropanamide,
N,N-Diethyl-2-(2-(3,4-dimethoxyphenyl)benzofuran-5-yl)acetamide,
2-(2-(3,4-Dimethoxyphenyl)benzofuran-5-yl)-N,N-dimethylacetamide,
N-[2-(3,4-Dimethoxy-phenyl)-benzofuran-5-yl]-propionamide,
N-[2-(3,4-Dimethoxy-phenyl)-benzofuran-5-yl]-butyramide,
Butyl-[2-(3,4-dimethoxy-phenyl)-benzofuran-5-yl]-amine;
Among the group of general formula (Id),
Methyl 3-[2-(4'-hydroxy-3'-methoxyphenyl)-benzofuran-5-yl]-propionate,
2-[2-(3-methoxy-4-methoxymethoxy-phenyl)-3-methylsulfanyl-benzofuran-5-yl]-1-ethanol,
3-[2-(3-methoxy-4-methoxymethoxy-phenyl)-3-methylsulfanyl-benzofuran-5-yl]-propan-1-ol,
2-methoxy-4-[5-(2-methoxy-ethyl)-benzofuran-2-yl]-phenol, Pentafluorophenyl 2-[2-(4'-hydroxy-3'-methoxyphenyl)-3-(methylthio)-benzofuran-5-yl]-acetate,
Pentafluorophenyl 3-[2-(4'-hydroxy-3'-methoxyphenyl)-3-(methylthio)-benzofuran-5-yl]-propionate,
Pentafluorophenyl 2-[2-(4'-hydroxy-3'-methoxyphenyl)-benzofuran-5-yl]-acetate,
Pentafluorophenyl 3-[2-(4'-hydroxy-3'-methoxyphenyl)-benzofuran-5-yl]-propionate,
2-[2-(4'-hydroxy-3'-methoxyphenyl)-3-(methylthio)-benzofuran-5-yl]-1-morpholino-1-ethanone,
2-[2-(4'-hydroxy-3'-methoxyphenyl)-3-(methylthio)-benzofuran-5-yl]-1-piperazino-1-ethanone,
2-[2-(4'-hydroxy-3'-methoxyphenyl)-3-(methylthio)-benzofuran-5-yl]-1-(4-benzylpiperazino)-1-ethanone,
2-[2-(4'-hydroxy-3'-methoxyphenyl)-3-(methylthio)-benzofuran-5-yl]-1-(4-benzylpiperidino)-1-ethanone,
3-[2-(4'-hydroxy-3'-methoxyphenyl)-3-(methylthio)-benzofuran-5-yl]-1-morpholino-1-propanone,
3-[2-(4'-hydroxy-3'-methoxyphenyl)-3-(methylthio)-benzofuran-5-yl]-1-piperazino-1-propanone,
3-[2-(4'-hydroxy-3'-methoxyphenyl)-3-(methylthio)-benzofuran-5-yl]-1-(4-benzylpiperazino)-1-propanone,
3-[2-(4'-hydroxy-3'-methoxyphenyl)-3-(methylthio)-benzofuran-5-yl]-1-(4-benzylpiperidino)-1-propanone,
Methyl 3-{2-[4'-(3-chloropropoxy)-3'-methoxyphenyl]-3-(methylthio)-benzofuran-5-yl}propionate,
[2-(3,4-dimethoxyphenyl)-3-methylsulfanyl-benzofuran-5-yl]acetic acid pentafluorophenyl ester,
3-[2-(3,4-dimethoxy-phenyl)-3-methylsulfanyl-benzofuran-5-yl]propionic acid pentafluorophenyl ester,
[2-(3,4-dimethoxy-phenyl)-benzofuran-5-yl]acetic acid pentafluorophenyl ester,
3-[2-(3,4-dimethoxy-phenyl)-benzofuran-5-yl]propionic acid pentafluorophenyl ester,
2-[2-(3,4-dimethoxy-phenyl)-3-methylsulfanyl-benzofuran-5-yl]-1-(4-phenyl-piperazin-1-yl)-ethanone,
3-[2-(3,4-dimethoxy-phenyl)-3-methylsulfanyl-benzofuran-5-yl]-1-(4-phenyl-piperazin-1-yl)-propan-1-one,
1-(4-benzyl-piperazin-1-yl)-2-[2-(3,4-dimethoxy-phenyl)-3-methylsulfanyl-benzofuran-5-yl]-ethanone,
1-(4-benzyl-piperazin-1-yl)-3-[2-(3,4-dimethoxy-phenyl)-3-methylsulfanyl-benzofuran-5-yl]-propan-1-one,
2-[2-(3,4-dimethoxy-phenyl)-benzofuran-5-yl]-1-(4-phenyl-piperazine-1-yl) ethanone,
3-[2-(3,4-dimethoxy-phenyl)-benzofuran-5-yl]-1-(4-phenyl-piperazine-1-yl) propan-1-one,
1-(4-benzyl-piperazin-1-yl)-2-[2-(3,4-dimethoxy-phenyl)-benzofuran-5-yl]-ethanone,
1-(4-benzyl-piperazin-1-yl)-3-[2-(3,4-dimethoxy-phenyl)-benzofuran-5-yl]-propan-1-one,
3-(2-(4-Hydroxy-3-methoxyphenyl)-3-(methylthio)benzofuran-5-yl)-1-(piperidin-1-yl)propan-1-one,
3-(2-(4-Hydroxy-3-methoxyphenyl)-3-(methylthio)benzofuran-5-yl)-1-(pyrrolidin-1-yl)propan-1-one,
3-(2-(3,4-Dimethoxyphenyl)-3-(methylthio)benzofuran-5-yl)-1-(piperidin-1-yl)propan-1-one,
3-(2-(3,4-Dimethoxyphenyl)-3-(methylthio)benzofuran-5-yl)-1-(pyrrolidin-1-yl)propan-1-one,
2-(2-(4-Hydroxy-3-methoxyphenyl)-3-(methylthio)benzofuran-5-yl)-1-(piperidin-1-yl)ethanone,
2-(2-(4-Hydroxy-3-methoxyphenyl)-3-(methylthio)benzofuran-5-yl)-1-((2S,6R)-2,6-dimethylmorpholino)ethanone,
2-(2-(4-Hydroxy-3-methoxyphenyl)-3-(methylthio)benzofuran-5-yl)-1-(4-methylpiperazin-1-yl)ethanone,
2-(2-(4-Hydroxy-3-methoxyphenyl)-3-(methylthio)benzofuran-5-yl)-1-(piperidin-1-yl)propan-1-one,
2-(2-(3,4-Dimethoxyphenyl)-3-(methylthio)benzofuran-5-yl)-1-(piperidin-1-yl)ethanone,
2-(2-(3,4-Dimethoxyphenyl)-3-(methylthio)benzofuran-5-yl)-1-(pyrrolidin-1-yl)ethanone,
2-(2-(3,4-Dimethoxyphenyl)-3-(methylthio)benzofuran-5-yl)-1-morpholinoethanone,
2-(2-(3,4-Dimethoxyphenyl)-3-(methylthio)benzofuran-5-yl)-1-(4-methylpiperidin-1-yl)ethanone,
2-(2-(3,4-Dimethoxyphenyl)-3-(methylthio)benzofuran-5-yl)-1-((2S,6R)-2,6-dimethylmorpholino)ethanone,
3-(2-(3,4-Dimethoxyphenyl)benzofuran-5-yl)-1-(pyrrolidin-1-yl)propan-1-one,
3-(2-(3,4-Dimethoxyphenyl)benzofuran-5-yl)-1-(piperidin-1-yl)propan-1-one,
3-(2-(3,4-Dimethoxyphenyl)benzofuran-5-yl)-1-morpholinopropan-1-one,
3-(2-(3,4-Dimethoxyphenyl)benzofuran-5-yl)-1-((2S,6R)-2,6-dimethylmorpholino)propan-1-one,
2-(2-(4-Hydroxy-3-methoxyphenyl)benzofuran-5-yl)-1-(piperidin-1-yl)ethanone,
2-(2-(4-Hydroxy-3-methoxyphenyl)benzofuran-5-yl)-1-(pyrrolidi n-1-yl)ethanone,
2-(2-(4-Hydroxy-3-methoxyphenyl)benzofuran-5-yl)-1-((2S,6R)-2,6-dimethylmorpholino)ethanone,
1-(4-Benzylpiperidin-1-yl)-2-(2-(4-hydroxy-3-methoxyphenyl)benzofuran-5-yl)ethanone,
2-(2-(4-Hydroxy-3-methoxyphenyl)benzofuran-5-yl)-1-(4-phenylpiperazin-1-yl)ethanone,
2-(2-(4-Hydroxy-3-methoxyphenyl)benzofuran-5-yl)-1-(piperidin-1-yl)propan-1-one,
2-(2-(4-Hydroxy-3-methoxyphenyl)benzofuran-5-yl)-1-(4-methylpiperidin-1-yl)propan-1-one,
2-(2-(4-Hydroxy-3-methoxyphenyl)benzofuran-5-yl)-1-morpholinopropan-1-one,
2-(2-(4-Hydroxy-3-methoxyphenyl)benzofuran-5-yl)-1-((2S,6R)-2,6-dimethylmorpholino)propan-1-one,
2-(2-(4-Hydroxy-3-methoxyphenyl)benzofuran-5-yl)-1-(pyrrolidin-1-yl)propan-1-one,
2-(2-(3,4-Dimethoxyphenyl)benzofuran-5-yl)-1-(piperidin-1-yl)ethanone,
2-(2-(3,4-Dimethoxyphenyl)benzofuran-5-yl)-1-(4-methylpiperidin-1-yl)ethanone,
2-(2-(3,4-Dimethoxyphenyl)benzofuran-5-yl)-1-morpholinoethanone,
2-(2-(3,4-Dimethoxyphenyl)benzofuran-5-yl)-1-(pyrrolidin-1-yl)ethanone,
1-(4-Benzylpiperidin-1-yl)-2-(2-(3,4-dimethoxyphenyl)benzofuran-5-yl)ethanone,
2-(2-(3,4-Dimethoxyphenyl)benzofuran-5-yl)-1-(4-methylpiperazin-1-yl)ethanone,
3-(2-(4-Hydroxy-3-methoxyphenyl)benzofuran-5-yl)-1-(piperidin-1-yl)propan-1-one.

The inventive compounds represented by general formula (I) can be transformed into their pharmaceutically acceptable salt and solvates by the conventional method well known in the art. For the salts, acid-addition salt thereof formed by a pharmaceutically acceptable free acid thereof is useful and can be prepared by the conventional method. For example, after dissolving the compound in the excess amount of acid solution, the salts are precipitated by the water-miscible organic solvent such as methanol, ethanol, acetone or acetonitrile to prepare acid addition salt thereof and further the mixture of equivalent amount of compound and diluted acid with water or alcohol such as glycol monomethylether, can be heated and subsequently dried by evaporation or filtrated under reduced pressure to obtain dried salt form thereof.

As a free acid of above-described method, organic acid or inorganic acid can be used. For example, organic acid such as methansulfonic acid, p-toluensulfonic acid, acetic acid, trifluoroacetic acid, citric acid, maleic acid, succinic acid, oxalic acid, benzoic acid, lactic acid, glycolic acid, gluconic acid, galacturonic acid, glutamic acid, glutaric acid, glucuronic acid, aspartic acid, ascorbic acid, carbonylic acid, vanillic acid, hydroiodic acid and the like, and inorganic acid such as hydrochloric acid, phosphoric acid, sulfuric acid, nitric acid, tartaric acid and the like can be used herein.

Further, the pharmaceutically acceptable metal salt form of inventive compounds may be prepared by using base. The alkali metal or alkali-earth metal salt thereof can be prepared by the conventional method, for example, after dissolving the compound in the excess amount of alkali metal hydroxide or alkali-earth metal hydroxide solution, the insoluble salts are filtered and remaining filtrate is subjected to evaporation and drying to obtain the metal salt thereof. As a metal salt of the present invention, sodium, potassium or calcium salt are pharmaceutically suitable and the corresponding silver salt can be prepared by reacting alkali metal salt or alkali-earth metal salt with suitable silver salt such as silver nitrate.

The pharmaceutically acceptable salt of the compound represented by general formula (I) comprise all the acidic or basic salt which may be present at the compounds, if it does not indicated specifically herein. For example, the pharmaceutically acceptable salt of the present invention comprise the salt of hydroxyl group such as the sodium, calcium and potassium salt thereof; the salt of amino group such as the hydrogen bromide salt, sulfuric acid salt, hydrogen sulfuric acid salt, phosphate salt, hydrogen phosphate salt, dihydrophosphate salt, acetate salt, succinate salt, citrate salt, tartarate salt, lactate salt, mandelate salt, methanesulfonate(mesylate) salt and p-toluenesulfonate (tosylate) salt etc, which can be prepared by the conventional method well known in the art.

There may exist in the form of optically different diastereomers since the compounds represented by general formula (I) have unsymmetrical centers, accordingly, the compounds of the present invention comprise all the optically active isomers, R or S stereoisomers and the mixtures thereof. Present invention also comprises all the uses of racemic mixture, more than one optically active isomer or the mixtures thereof as well as all the preparation or isolation method of the diastereomer well known in the art.

The compounds of the invention of formula (I) may be chemically synthesized by the methods which will be explained by following reaction schemes hereinafter, which are merely exemplary and in no way limit the invention. The reaction schemes show the steps for preparing the representative compounds of the present invention, and the other compounds also may be produced by following the steps with appropriate modifications of reagents and starting materials, which are envisaged by those skilled in the art.

General Synthetic Procedures

Scheme 1.

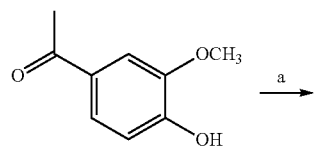

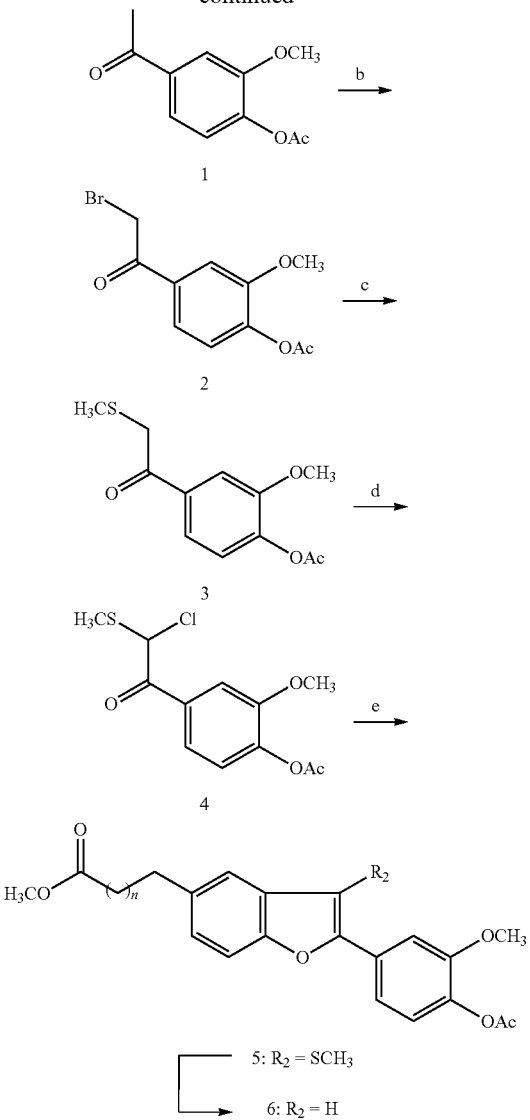

a. Ac$_2$O, pyridine, THF, quantitavive;
b. Br$_2$, 45% HBr(cat.), AcOH, 94%;
c. NaSCH$_3$, aliquat336, benzene/H$_2$O, 83%;
d. N-chloro-succinimide, CCl$_4$ 87%;
e. 4-hydroxyphenylacetic acid methylester (n = 0) or 3-(4-hydroxyphenyl) propionic acid methylester (n = 1), ZnCl$_2$, CH$_2$Cl$_2$, 81%(n = 0), 84%(n = 1);
f. Raney Nickel, EtOH, 92%(n = 0), 94%(n = 1)

As depicted in the above Scheme 1, the scheme explains the process for preparing novel benzofuran derivatives (5-6) from conventionally available or easily prepared starting materials well-known in the art as follows:

At the 1$^{st}$ step, 3-methoxy-4-hydroxy-benzaldehyde is acetylated with the solvent to obtain acetylated intermediate compound (1). The solvent which does not cause to adverse effect such as acetic acid, pyridine, THF etc may be used in the reaction. It is preferable that the reaction temperature in the reaction can be performed at cool temperature to room temperature, preferably, at room temperature however it is not limited thereto. It is preferable that the reaction period in the reaction can be performed in the range from 5 hrs to 24 hrs, more preferably, 24 hrs with stirring to synthesize the intermediate (1).

At the 2nd step, the brominated intermediate compound (2) can be prepared by reacting the intermediate (1) with the appropriate reagent such as bromine, 45% hydrogen bromide and acetate.

At the 3rd step, the intermediate compound (3) can be prepared by reacting the intermediate (2) with the appropriate reagent such as NaSCH₃, Aliquat 336 and benzene/H₂O.

At the 4th step, the intermediate compound (4) can be prepared by reacting the intermediate (3) with the appropriate reagent such as N-chloro-succiimide and CCl₄.

At the 5th step, the intermediate compound (5) can be prepared by reacting the intermediate (4) with the appropriate reagent such as zinc chloride, dichloromethane, 4-hydroxyphenylacetic acid (n=0) and 3-(4-hydroxyphenyl)propionic acid methylester (n=1).

At the 6th step, the intermediate compound (6) can be prepared by reacting the intermediate (5) with the appropriate reducing condition such as Raney nickel and ethanol etc.

The solvent which does not cause to adverse effect, for example, dichloromethane, alcohol solvent such as methanol, ethanol etc, or acetone etc, preferably, ethanol may be used in the reaction.

The solvent which does not cause to adverse effect, for example, dimethylformamide, alcohol solvent such as methanol, ethanol etc or acetone may be used in the reaction. It is preferable that the reaction temperature in the reaction can be performed at cool temperature to room temperature, preferably, at room temperature however it is not limited thereto.

At the 3rd step, the intermediate compound (11-12) can be prepared by reacting the intermediate (9-10) with the appropriate reagent such as LAH (lithium hydrogenated aluminum), THF etc.

Scheme 3.

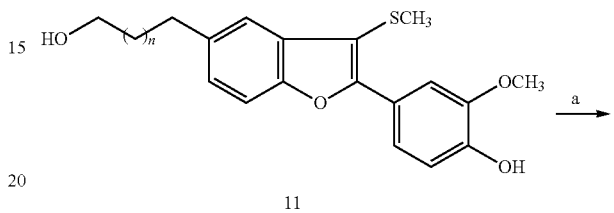

11

Scheme 2.

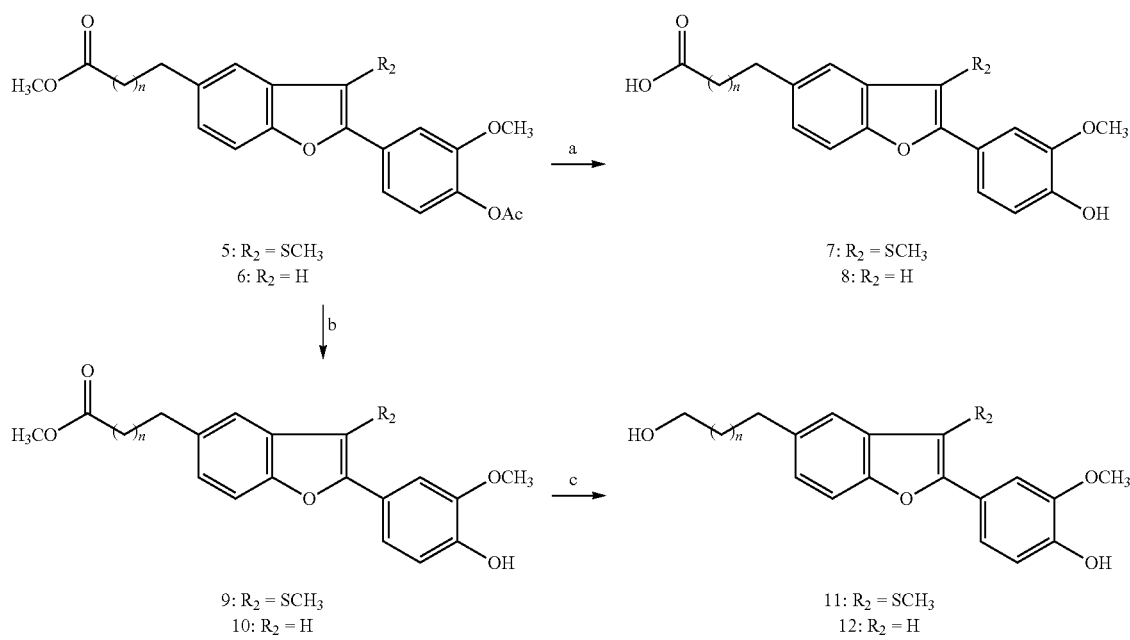

a. LiOH H₂O, THF, 94-99%;
b. K₂CO₃, H₂O, MeOH, 92-95%;
c. LiAlH₄, THF, 51-58%

As depicted in the above Scheme 2, the scheme explains the process for preparing novel benzofuran derivatives (11-12) from conventionally available or easily prepared starting materials well-known in the art as follows:

At the 1st step, the compounds (5-6) prepared in the above-described step is reacted to obtain the intermediate compound (7-8) under appropriate condition such as lithium hydroxide, water and THF etc.

At the 2nd step, the compounds (7-8) prepared in the above-described step is reacted to obtain the intermediate compound (9-10) under appropriate condition such as potassium carbonate, water and ethanol etc.

-continued

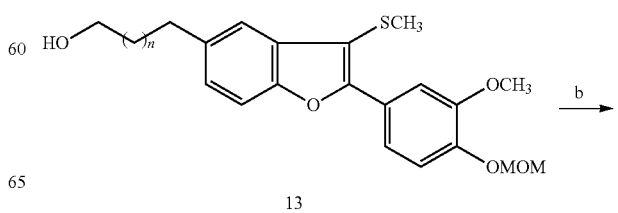

13

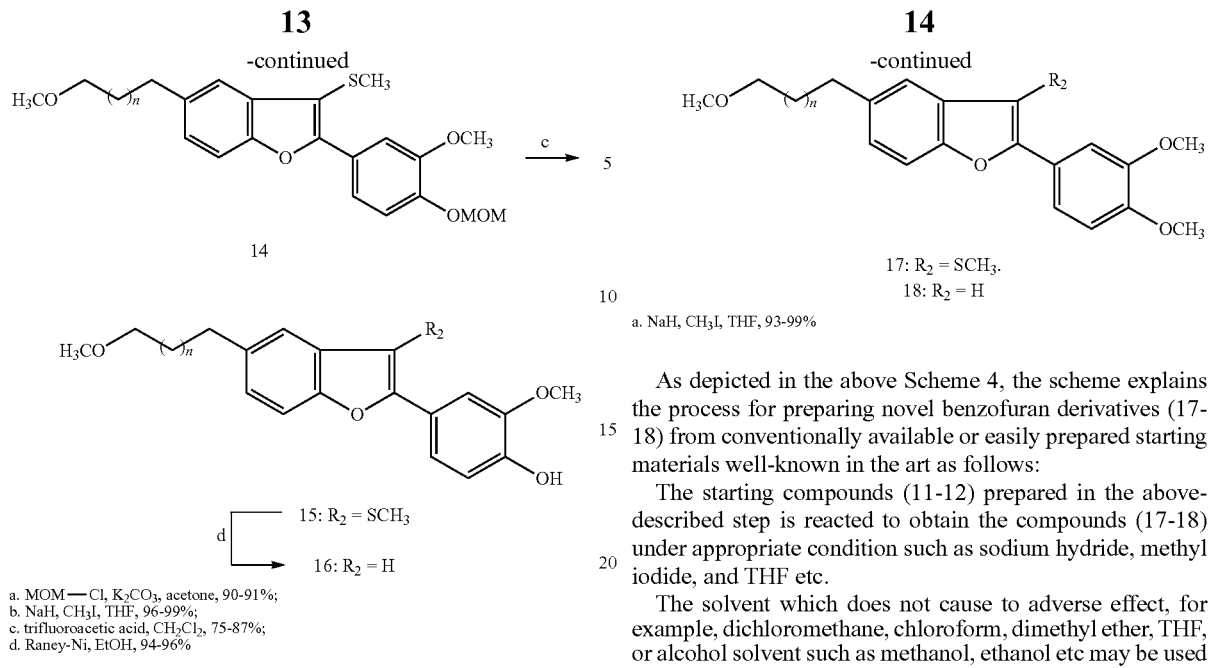

15: R$_2$ = SCH$_3$
16: R$_2$ = H a. MOM—Cl, K$_2$CO$_3$, acetone, 90-91%;
b. NaH, CH$_3$I, THF, 96-99%;
c. trifluoroacetic acid, CH$_2$Cl$_2$, 75-87%;
d. Raney-Ni, EtOH, 94-96%

As depicted in the above Scheme 3, the scheme explains the process for preparing novel benzofuran derivatives (15-16) from conventionally available or easily prepared starting materials well-known in the art as follows:

At the 1$^{st}$ step, the starting compound (11) prepared in the above-described step is reacted to obtain the compound (13) under appropriate condition such as MOM-Cl, potassium carbonate and acetone etc.

At the 2$^{nd}$ step, the compounds (13) prepared in the above-described step is reacted to obtain the compound (14) under appropriate condition such as sodium hydroxide, methyl iodide and TI-IF etc.

At the 3$^{rd}$ step, the compounds (14) prepared in the above-described step is reacted to obtain the compound (15) under appropriate condition such as trifluoroacetic acid and dichloromethane etc.

At the 4$^{th}$ step, the compound (16) can be prepared by reacting the intermediate (15) with the appropriate reducing reagent such as Raney nickel and ethanol etc.

The solvent which does not cause to adverse effect, for example, dichloromethane, chloroform, dimethyl ether, THF, or alcohol solvent such as methanol, ethanol etc may be used in the reaction. It is preferable that the reaction temperature in the reaction can be performed at cool temperature to room temperature, preferably, at room temperature however it is not limited thereto.

Scheme 4.

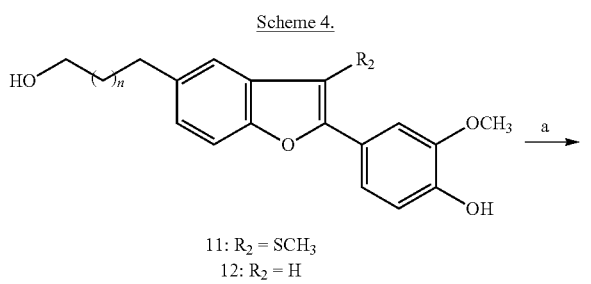

11: R$_2$ = SCH$_3$
12: R$_2$ = H

17: R$_2$ = SCH$_3$.
18: R$_2$ = H a. NaH, CH$_3$I, THF, 93-99%

As depicted in the above Scheme 4, the scheme explains the process for preparing novel benzofuran derivatives (17-18) from conventionally available or easily prepared starting materials well-known in the art as follows:

The starting compounds (11-12) prepared in the above-described step is reacted to obtain the compounds (17-18) under appropriate condition such as sodium hydride, methyl iodide, and THF etc.

The solvent which does not cause to adverse effect, for example, dichloromethane, chloroform, dimethyl ether, THF, or alcohol solvent such as methanol, ethanol etc may be used in the reaction. It is preferable that the reaction temperature in the reaction can be performed at cool temperature to room temperature, preferably, at room temperature however it is not limited thereto.

Scheme 5.

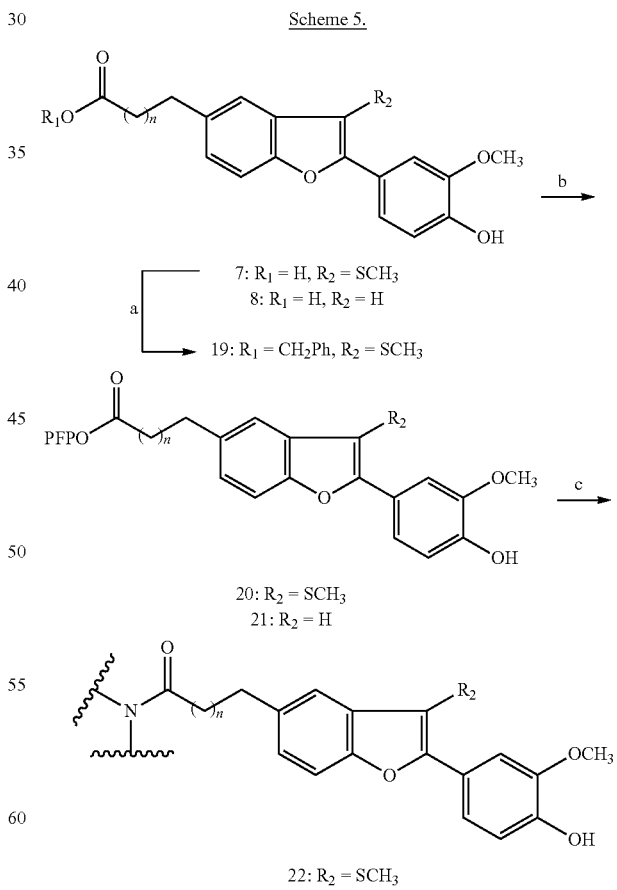

7: R$_1$ = H, R$_2$ = SCH$_3$
8: R$_1$ = H, R$_2$ = H

19: R$_1$ = CH$_2$Ph, R$_2$ = SCH$_3$

20: R$_2$ = SCH$_3$
21: R$_2$ = H

22: R$_2$ = SCH$_3$ a. Benzyl alcohol, EDC, DMAP; DMF, 97-98%;
b. pentafluorophenol, EDC, CH$_2$Cl$_2$/DMF, 84-88%;
c. substituted amines, various method, 34-98%

As depicted in the above Scheme 5, the scheme explains the process for preparing novel benzofuran derivatives (22) from conventionally available or easily prepared starting materials well-known in the art as follows:

At the 1$^{st}$ step, the starting compound (7) prepared in the above-described Scheme 2 is reacted to obtain the compound (19) under appropriate condition such as benzyl alcohol, dimethylaminopyridine, and EDC etc.

At the 2$^{nd}$ step, the compounds (19) prepared in the above-described step is reacted to obtain the compounds (20-21) under appropriate condition such as pentafluorophenol, EDC, and dichloromethane dissolved in DMF (Dimethylformamide) etc.

At the 3$^{rd}$ step, the compounds (20-21) prepared in the above-described step is reacted with amines having various substituents to obtain the compound (22) under appropriate condition.

The solvent which does not cause to adverse effect, for example, dichloromethane, chloroform, dimethyl ether, THF, or alcohol solvent such as methanol, ethanol etc may be used in the reaction. It is preferable that the reaction temperature in the reaction can be performed at cool temperature to room temperature, preferably, at room temperature however it is not limited thereto.

Scheme 6.

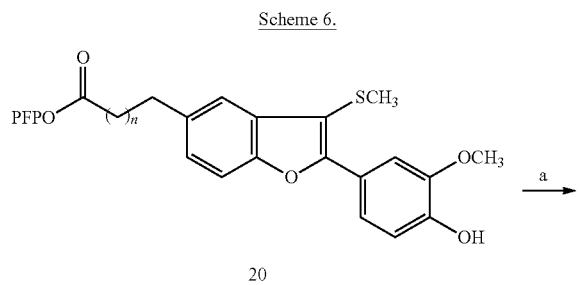

20

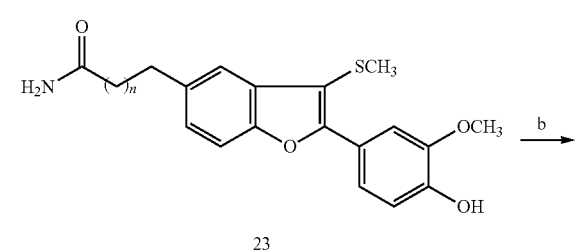

23

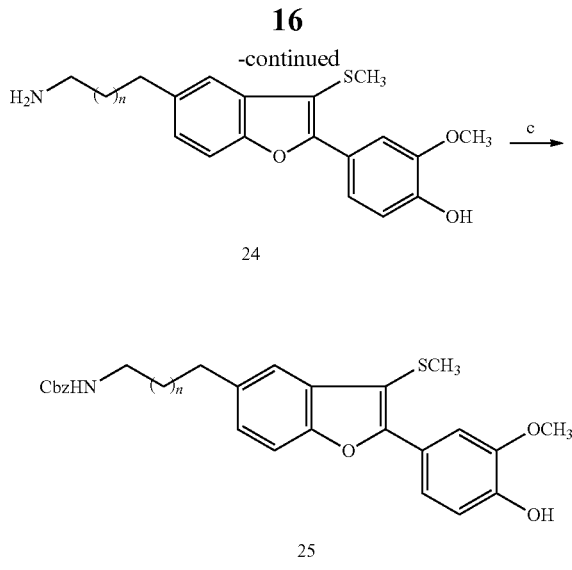

a. NH$_3$, MeOH, 88-95%;
b. LiAlH$_4$, THF, 62-65%;
c. benzylchloroformate, TEA, THF, 84-85%

As depicted in the above Scheme 6, the scheme explains the process for preparing benzofuran derivatives (25) from conventionally available or easily prepared starting materials well-known in the art as follows:

At the 1$^{st}$ step, the starting compound (20) prepared in the above-described Scheme 5 is reacted to obtain the compound (23) under appropriate condition such as ammonia and methanol etc.

At the 2$^{nd}$ step, the compound (23) prepared in the above-described step is reacted to obtain the compound (24) under appropriate condition such as LAH and THF etc.

At the 3$^{rd}$ step, the compound (24) prepared in the above-described step is reacted to obtain the compound (25) under appropriate condition such as benzylchloroformate, TEA and THF etc.

The solvent which does not cause to adverse effect, for example, dichloromethane, chloroform, dimethyl ether, THF, or alcohol solvent such as methanol, ethanol etc may be used in the reaction. It is preferable that the reaction temperature in the reaction can be performed at cool temperature to room temperature, preferably, at room temperature however it is not limited thereto.

Scheme 7.

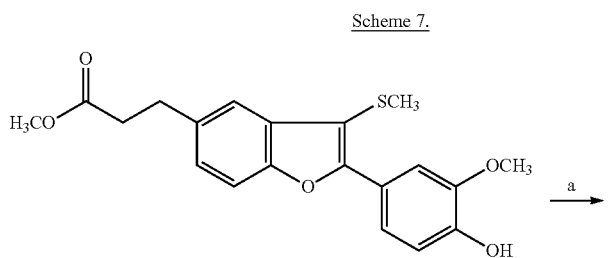

9a

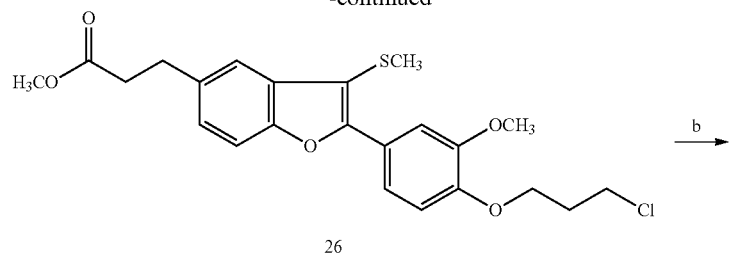

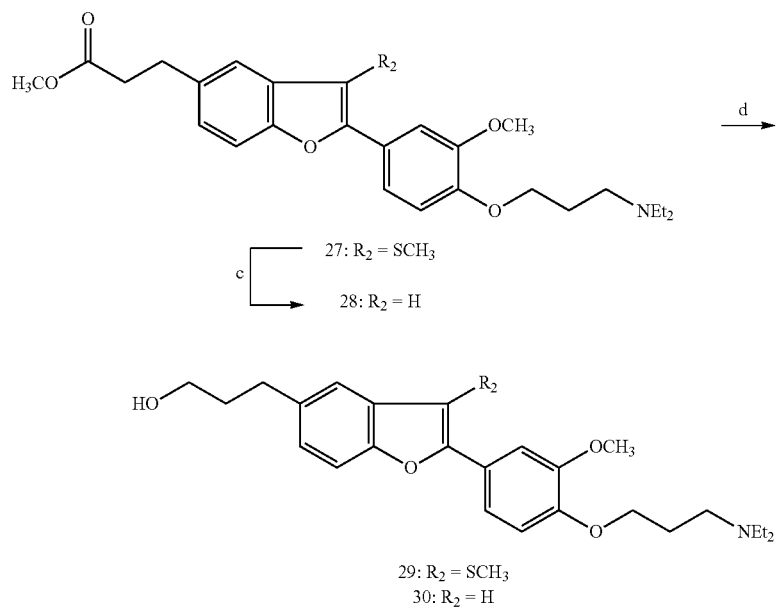

a. 1-bromo-3-chloropropane, K₂CO₃, acetone, 85%;
b. Et₂NH, MeOH, 92%;
c. Raney-Ni, MeOH, 84%;
d. LiAlH₄, THF, 58-62%

As depicted in the above Scheme 7, the scheme explains the process for preparing benzofuran derivatives (29-30) from conventionally available or easily prepared starting materials well-known in the art as follows:

At the 1$^{st}$ step, the starting compound (9) prepared in the above-described Scheme 2 is reacted to obtain the compound (26) under appropriate condition such as 1-bromo-3-chloropropane, calcium carbonate, and methanol etc.

At the 2$^{nd}$ step, the compound (26) prepared in the above-described step is reacted to obtain the compound (27) under appropriate condition such as diethylamine, and methanol etc.

At the 3$^{rd}$ step, the compound (27) prepared in the above-described step is reacted to obtain the compound (28) under appropriate reducing condition such as Raney nickel, and methanol etc.

At the 4$^{th}$ step, the compound (28) prepared in the above-described step is reacted to obtain the compounds (29-30) under appropriate condition such as LAH, and THF etc.

The solvent which does not cause to adverse effect, for example, dichloromethane, chloroform, dimethyl ether, THF, or alcohol solvent such as methanol, ethanol etc may be used in the reaction. It is preferable that the reaction temperature in the reaction can be performed at cool temperature to room temperature, preferably, at room temperature however it is not limited thereto.

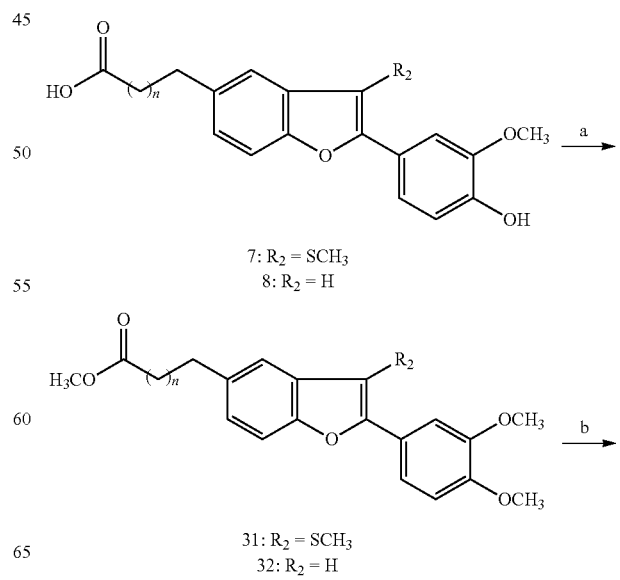

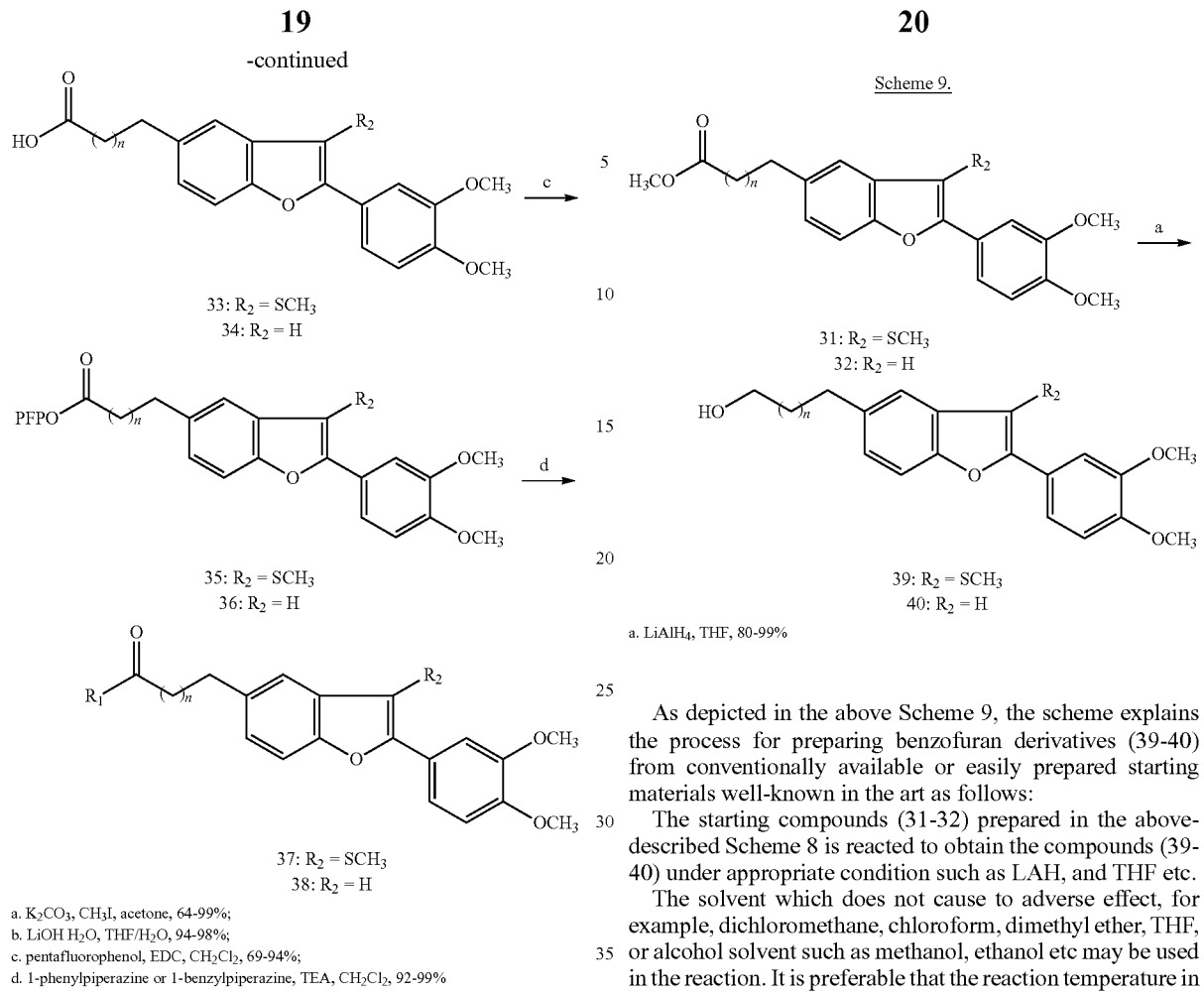

a. K₂CO₃, CH₃I, acetone, 64-99%;
b. LiOH H₂O, THF/H₂O, 94-98%;
c. pentafluorophenol, EDC, CH₂Cl₂, 69-94%;
d. 1-phenylpiperazine or 1-benzylpiperazine, TEA, CH₂Cl₂, 92-99%

As depicted in the above Scheme 8, the scheme explains the process for preparing benzofuran derivatives (37-38) from conventionally available or easily prepared starting materials well-known in the art as follows:

At the 1$^{st}$ step, the starting compounds (7-8) prepared in the above-described Scheme 2 is reacted to obtain the compounds (31-32) under appropriate condition such as potassium carbonate, methyl iodide, and acetone etc.

At the 2$^{nd}$ step, the compounds (31-32) prepared in the above-described step is reacted to obtain the compounds (33-34) under appropriate condition such as lithium hydroxide dissolved in water and THF in water etc.

At the 3$^{rd}$ step, the compounds (33-34) prepared in the above-described step is reacted to obtain the compounds (35-36) under appropriate condition such as pentafluorophenol, EDC and dichloromethane etc.

At the 4$^{th}$ step, the compounds (35-36) prepared in the above-described step is reacted to obtain the compounds (37-38) under appropriate condition such as 1-phenylpiperazine, 1-benzylpiperazine, TEA and dichloromethane etc.

The solvent which does not cause to adverse effect, for example, dichloromethane, chloroform, dimethyl ether, THF, or alcohol solvent such as methanol, ethanol etc may be used in the reaction. It is preferable that the reaction temperature in the reaction can be performed at cool temperature to room temperature, preferably, at room temperature however it is not limited thereto.

a. LiAlH₄, THF, 80-99%

As depicted in the above Scheme 9, the scheme explains the process for preparing benzofuran derivatives (39-40) from conventionally available or easily prepared starting materials well-known in the art as follows:

The starting compounds (31-32) prepared in the above-described Scheme 8 is reacted to obtain the compounds (39-40) under appropriate condition such as LAH, and THF etc.

The solvent which does not cause to adverse effect, for example, dichloromethane, chloroform, dimethyl ether, THF, or alcohol solvent such as methanol, ethanol etc may be used in the reaction. It is preferable that the reaction temperature in the reaction can be performed at cool temperature to room temperature, preferably, at room temperature however it is not limited thereto.

The novel benzofuran derivatives prepared by the above-described method represented by general formula (I) shows potent inhibiting activity of beta-amyloid aggregation and cell cytotoxicity resulting in stimulating the proliferation of neuronal cells as well as recovering activity of memory learning injury caused by neuronal cell injury using transformed animal model with beta-amyloid precursor gene, therefore the compounds can be useful in treating or preventing cognitive function disorder.

Accordingly, it is another object of the present invention to provide the pharmaceutical composition comprising an efficient amount of the compound represented by general formula (I) or the pharmaceutically acceptable salt thereof as an active ingredient in amount effective to treat or prevent cognitive function disorder, together with pharmaceutically acceptable carriers or diluents.

It is another object of the present invention to provide the pharmaceutical composition comprising an efficient amount of the compound represented by general formula (I) or the pharmaceutically acceptable salt thereof as an active ingredient in amount effective to treat or prevent cognitive function disorder, together with pharmaceutically acceptable carriers or diluents.

In accordance with the other aspect of the present invention, there is also provided a use of the compound represented by general formula (I) or the pharmaceutically acceptable salt thereof for manufacture of medicines employed for treating or preventing cognitive function disorder in mammals including human as an active ingredient in amount effective to treat or prevent cognitive function disorder.

In accordance with the other aspect of the present invention, there is also provided a use of the compound represented by general formula (I) or the pharmaceutically acceptable salt thereof for manufacture of medicines employed for treating or preventing cognitive function disorder in mammals including human as an active ingredient in amount effective to treat or prevent cognitive function disorder.

In accordance with the other aspect of the present invention, there is also provided a method of treating or preventing cognitive function disorder in a mammal comprising administering to said mammal an effective amount of novel derivatives represented by general formula (I) and the pharmacologically acceptable salt thereof, together with a pharmaceutically acceptable carrier thereof into the mammals including human suffering from said disease.

In accordance with the other aspect of the present invention, there is also provided a method of inhibiting accumulated beta-amyloid in a mammal comprising administering to said mammal an effective amount of novel derivatives represented by general formula (I) and the pharmacologically acceptable salt thereof, together with a pharmaceutically acceptable carrier thereof into the mammals including human suffering from said disease.

The term "cognitive function disorder" disclosed herein comprise various cognitive function disorder caused by accumulated beta-amyloid, for example, Alzheimer type dementia, cerebrovascular type dementia, Pick's disease, Creutzfeldt-jakob's disease, dementia caused by cephalic damage, Parkinson's disease, and the like, preferably, Parkinson's disease.

The compound according to the present invention can be provided as a pharmaceutical composition containing pharmaceutically acceptable carriers, adjuvants or diluents. For example, the compound of the present invention can be dissolved in oils, propylene glycol or other solvents which are commonly used to produce an injection. Suitable examples of the carriers include physiological saline, polyethylene glycol, ethanol, vegetable oils, isopropyl myristate, etc., but are not limited to them.

Hereinafter, the following formulation methods and excipients are merely exemplary and in no way limit the invention.

The compound of the present invention in pharmaceutical dosage forms may be used in the form of their pharmaceutically acceptable salts, and also may be used alone or in appropriate association, as well as in combination with other pharmaceutically active compounds.

The compound of the present invention may be formulated into preparations for injections by dissolving, suspending, or emulsifying them in aqueous solvents such as normal saline, 5% Dextrose, or non-aqueous solvent such as vegetable oil, synthetic aliphatic acid glycerides, esters of higher aliphatic acids or propylene glycol. The formulation may include conventional additives such as solubilizers, isotonic agents, suspending agents, emulsifying agents, stabilizers and preservatives.

The desirable dose of the inventive compound varies depending on the condition and the weight of the subject, severity, drug form, route and period of administration, and may be chosen by those skilled in the art. However, in order to obtain desirable effects, it is generally recommended to administer at the amount ranging 0.0001-100 mg/kg, preferably 0.001-10 mg/kg by weight/day of the inventive compound of the present invention. The dose may be administered in single or divided into several times per day. In terms of composition, the compound should be present between 0.0001 to 10% by weight, preferably 0.0001 to 1% by weight based on the total weight of the composition.

The pharmaceutical composition of present invention can be administered to a subject animal such as mammals (rat, mouse, domestic animals or human) via various routes. All modes of administration are contemplated, for example, administration can be made by inhaled, orally, rectally or by intravenous, intramuscular, subcutaneous, intrathecal, epidural or intracerebroventricular injection.

The novel benzofuran derivatives represented by general formula (I) of the present invention also can be used as a main component or additive and aiding agent in the preparation of various functional health food and health care food.

Accordingly, it is the other object of the present invention to provide a functional health food comprising novel benzofuran derivatives represented by general formula (I), or the pharmacologically acceptable salt thereof for alleviating or improve cognitive function disorder in human or mammal.

The term "a functional health food" defined herein the functional food having enhanced functionality such as physical functionality or physiological functionality by adding the compound of the present invention to conventional food to prevent or improve cognitive function disorder in human or mammal.

It is the other object of the present invention to provide a health care food comprising benzofuran derivatives represented by the following general formula (I), or the pharmacologically acceptable salt thereof, together with a sitologically acceptable additive for the prevention and alleviation of cognitive function disorder.

The term "a health care food" defined herein the food containing the compound of the present invention showing no specific intended effect but general intended effect in a small amount of quantity as a form of additive or in a whole amount of quantity as a form of capsule, pill, tablet etc.

The term "a sitologically acceptable additive" defined herein any substance the intended use which results or may reasonably be expected to result—directly or indirectly—in its becoming a component or otherwise affecting the characteristics of any food for example, thickening agent, maturing agent, bleaching agent, sequesterants, humectant, anti-caking agent, clarifying agents, curing agent, emulsifier, stabilizer, thickner, bases and acid, foaming agents, nutrients, coloring agent, flavoring agent, sweetner, preservative agent, antioxidant, etc, which shall be explained in detail as follows.

If a substance is added to a food for a specific purpose in that food, it is referred to as a direct additive and indirect food additives are those that become part of the food in trace amounts due to its packaging, storage or other handling.

Above described health foods can be contained in food, health beverage, dietary therapy etc, and may be used as a form of powder, granule, tablet, chewing tablet, capsule, beverage etc for preventing or improving cognitive function disorder.

Also, above described compounds can be added to food or beverage for prevention and improvement of cognitive function disorder. The amount of above described compound in food or beverage as a functional health food or health care food may generally range from about 0.01 to 100 w/w % of total weight of food for functional health food composition. In particular, although the preferable amount of the compound of the present invention in the functional health food, health care food or special nutrient food may be varied in accordance to the intended purpose of each food, it is preferably used in general to use as a additive in the amount of the compound of the present invention ranging from about 0.01 to 5% in food such as noodles and the like, from 40 to 100% in health care food on the ratio of 100% of the food composition.

Providing that the health beverage composition of present invention contains above described compound as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose etc; disaccharide such as maltose, sucrose etc; conventional sugar such as dextrin, cyclodextrin; and sugar alcohol such as xylitol, and erythritol etc. As the other deodorant than aforementioned ones, natural deodorant such as taumatin, stevia extract such as levaudioside A, glycyrrhizin et al., and synthetic deodorant such as saccharin, aspartam et al., may be useful favorably. The amount of above described natural carbohydrate is generally ranges from about 1 to 20 g, preferably 5 to 12 g in the ratio of 100 of present beverage composition.

The other components than aforementioned composition are various nutrients, a vitamin, a mineral or an electrolyte, synthetic flavoring agent, a coloring agent and improving agent in case of cheese, chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage, wherein the component can be used independently or in combination. The ratio of the components is not so important but is generally range from about 0 to 20 w/w % per 100 w/w % present composition. Examples of addable food comprising aforementioned extract therein are various food, beverage, gum, vitamin complex, health improving food and the like.

The present invention is more specifically explained by the following examples. However, it should be understood that the present invention is not limited to these examples in any manner.

Advantageous Effects

As described in the present invention, the novel benzofuran derivatives of the present invention showed potent inhibiting activity of beta-amyloid aggregation and cell cytotoxicity resulting in stimulating the proliferation of neuronal cells as well as recovering activity of memory learning injury caused by neuronal cell injury using transformed animal model with beta-amyloid precursor gene, therefore the compounds can be useful in treating or preventing cognitive function disorder.

DESCRIPTION OF DRAWINGS

The above and other objects, features and other advantages of the present invention will more clearly understood from the following detailed description taken in conjunction with the accompanying drawings, in which.

BEST MODE

Figure 1:
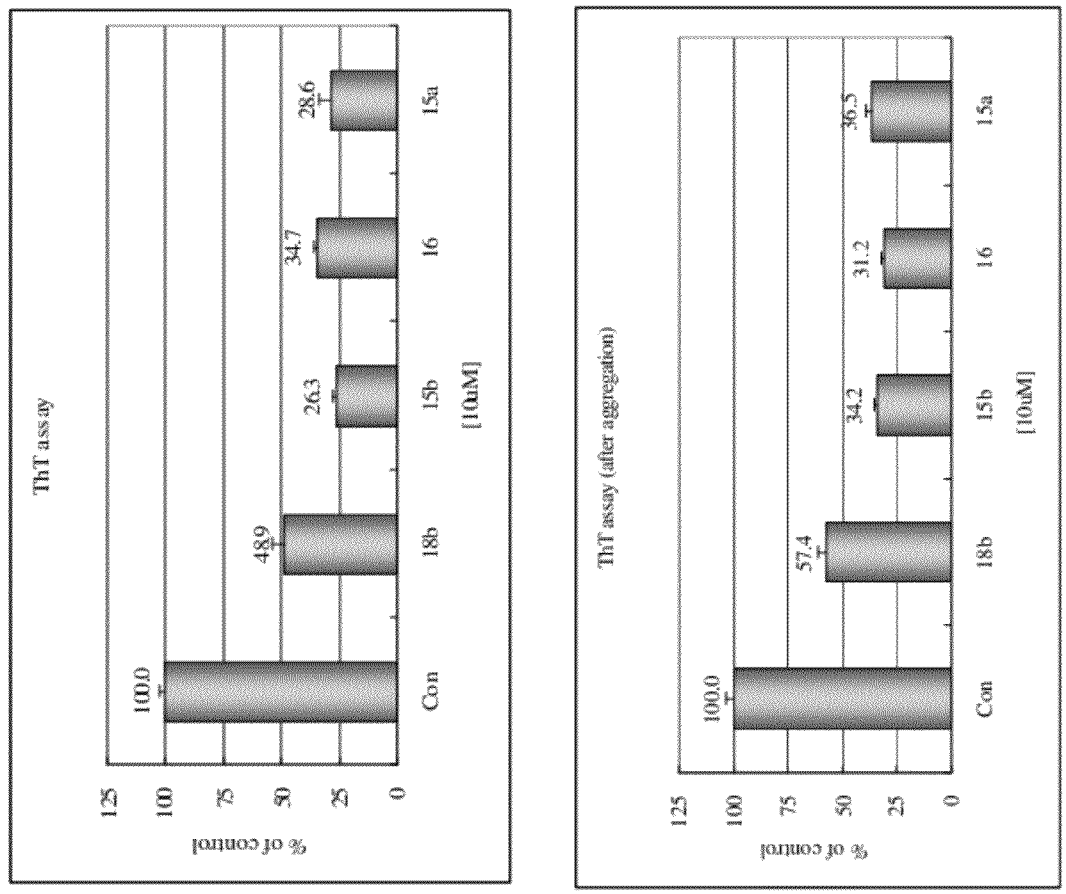
FIG. 1 shows the inhibition effect of inventive compounds on the aggregation of beta-amyloid and the lysis of aggregated beta-amyloid.

It will be apparent to those skilled in the art that various modifications and variations can be made in the compositions, use and preparations of the present invention without departing from the spirit or scope of the invention.

The present invention is more specifically explained by the following examples.

However, it should be understood that the present invention is not limited to these examples in any manner.

Mode for Invention

The following Reference Example, Examples and Experimental Examples are intended to further illustrate the present invention without limiting its scope.

Reference Example 1

Preparation of Intermediate (1):
4-acetyl-2-methoxyphenyl acetate (1)

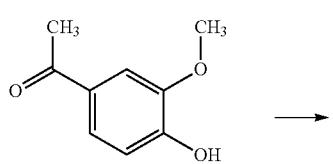

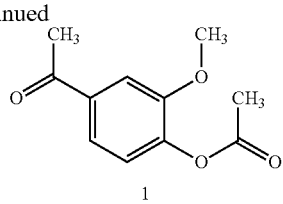

As shown in the above-described reaction formula, acetovanillone (500 mg, 3 mM) dissolved in 20 ml of THF was mixed with 0.5 ml of pyridine and 0.6 ml of anhydrous acetic acid. The mixture was stirred for 3 hours at room temperature. The resulting product was recovered with the extraction with diethylether and dried with anhydrous magnesium sulfate to remove remaining solvent. The remaining residue was performed to Silica gel column chromatography with a mobile phase (n-hexane:ethylacetate=4:1) to obtain white solid type of 4-acetyl-2-methoxyphenyl acetate (1; 625 mg).

m.p: 58.7° C.;

$^1$H NMR (CDCl$_3$): δ ppm 7.60 (d, 1H, J=1.8 Hz, H-3), 7.55 (dd, 1H, J=1.8, 8.2 Hz, H-5), 7.12 (d, 1H, J=8.2 Hz, H-6), 3.89 (s, 3H, OCH$_3$), 2.59 (s, 3H, OCOCH$_3$), 2.33 (s, 3H, COCH$_3$).

Reference Example 2

Preparation of Intermediate (2): 4-(2-bromoacetyl)-2-methoxyphenyl acetate (2)

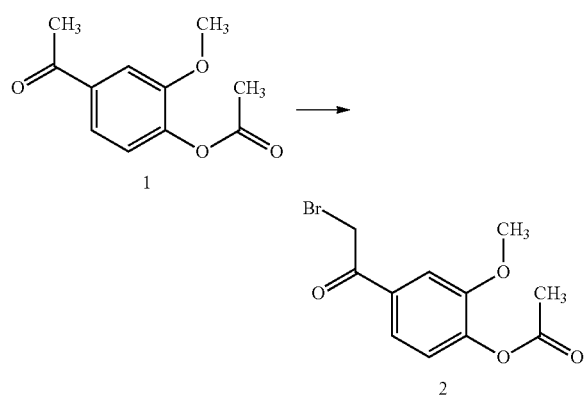

As shown in the above-described reaction formula, the solution containing 3.44 g of 4-acetyl-2-methoxyphenyl acetate (16.5 mM) was added to 7 ml of acetic acid dropwisely. 3 drops of 45% hydrobromic acid was added thereto and then 0.85 ml of brome (16.5 mM) was slowly added thereto.

The mixture solution was stirred to the extent that the product changed to colorless and the reaction mixture was cooled by adding 7 ml of water. The resulting product was extracted with dichloromethane, dried with anhydrous magnesium sulfate and the remaining solvent was removed. The remaining residue was performed to Silica gel column chromatography with a mobile phase (n-hexane:ethylacetate=4:1) to obtain white solid type of 4-(2-bromoacetyl)-2-methoxyphenyl acetate (2; 4.73 g).

Yield: 94%;

m.p: 82.0° C.;

$^1$H NMR (CDCl$_3$): δ ppm 7.63 (d, 1H, J=2 Hz, H-3), 7.58 (dd, 1H, J=2, 8 Hz, H-5), 7.16 (d, 1H, J=8 Hz, H-6), 4.43 (s, 2H, CH$_2$Br), 3.91 (s, 3H, OCH$_3$), 2.34 (s, 3H, COCH$_3$).

Reference Example 3

Preparation of Intermediate (3):2-methoxy-4-[-2-(methylthio)acetyl]phenyl acetate (3)

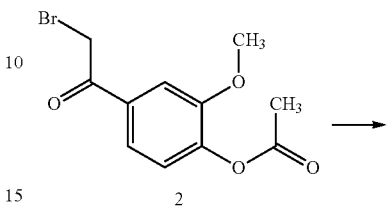

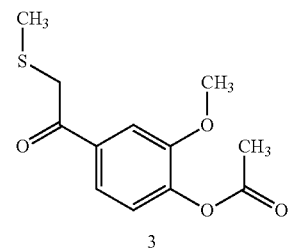

As shown in the above-described reaction formula, the mixture of 600 ml of sodium methyl mercaptan (8.56 ml) and three drops of aliquat/5 ml of water solution was added to the solution containing 2.46 g of 4-(2-bromoacetyl)-2-methoxyphenyl acetate (8.56 mM) dissolved in 10 ml of benzene. The mixture solution was stirred for 20 hours. The resulting product was extracted with ethylacetate, dried with anhydrous magnesium sulfate and the remaining solvent was removed. The remaining residue was performed to Silica gel column chromatography with a mobile phase (n-hexane:ethylacetate=4:1) to obtain white solid type of 2-methoxy-4-[-2-(methylthio)acetyl]phenyl acetate (3; 2.18 g).

Yield: 83%;

m.p=70.4° C.;

1H NMR (CDCl$_3$): δ ppm 7.64 (d, 1H, J=1.8 Hz, H-3), 7.57 (dd, 1H, J=1.8, 8.2 Hz, H-5), 7.13 (d, 1H, J=8.2 Hz, H-6), 3.90 (s, 3H, OCH$_3$), 3.74 (s, 2H, SCH$_2$CO), 2.34 (s, 3H, COCH$_3$), 2.15 (s, 3H, SCH$_3$).

Reference Example 4

Preparation of Intermediate (4): 4-[2-chloro-2-(methylthio)acetyl]-2-methoxy phenyl acetate (4)

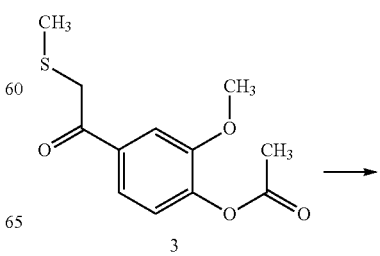

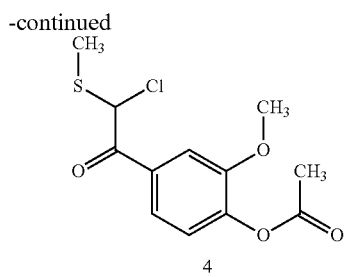

4

As shown in the above-described reaction formula, the mixture of 10 ml of carbon tetrachloride and 251 mg of N-chlorosuccinimide (1.88 mM) was added to 478 mg of 2-methoxy-4-[-2-(methylthio)acetyl]phenyl acetate (1.88 mM) at 0□. The mixture solution was left alone at room temperature and stirred for 6 hours. The resulting product was filtrated and the remaining solvent was removed. The remaining residue was performed to Silica gel column chromatography with a mobile phase (n-hexane:ethylacetate=4:1) to obtain colorless oil type of 4-[2-chloro-2-(methylthio)acetyl]-2-methoxy phenyl acetate (4; 542 mg).

Yield: 87%;
$^1$H NMR (CDCl$_3$): δ ppm 7.65 (d, 1H, J=2 Hz, H-3), 7.61 (dd, 1H, J=2, 8.2 Hz, H-5), 7.14 (d, 1H, J=8.2 Hz, H-6), 6.31 (s, 1H, SCHCl), 3.90 (s, 3H, OCH$_3$), 2.34 (s, 3H, COCH$_3$), 2.24 (s, 3H, SCH$_3$).

Example 1

Methyl 2-[2-(4' acetyloxy-3' methoxyphenyl)-3-(methylthio)-benzofuran-5-yl]acetate (5a)

1.17 g of zinc chloride (18.6 mM) was added to the mixture of 7.8 ml phenol dissolved in 40 ml of dichloromethane and 2.25 g of 4-[2-chloro-2-(methylthio)acetyl]-2-methoxy phenyl acetate (7.8 mM) under nitrogen gas atmosphere at −5° C.

The reaction mixture was stirred for 1 hour at −5° C. and cooled with adding water thereto slowly. The resulting product was filtrated and the remaining solvent was removed. The remaining residue was performed to Silica gel column chromatography with a mobile phase (n-hexane:ethylacetate=4:1) to obtain white solid type of Methyl 2-[2-(4'-acetyloxy-3'-methoxyphenyl)-3-(methylthio)-benzofuran-5-yl]acetate (5a; 3.12 g).

Yield: 81%;
m.p: 103° C.;
$^1$H NMR (CDCl$_3$): δ ppm 8.02 (d, 1H, J=1.8 Hz, H-2'), 7.93 (dd, 1H, J=1.8, 8.4 Hz, H-6), 7.61 (d, 1H, J=1.3 Hz, H-4), 7.47 (d, 1H, J=8.4 Hz, H-5', 7.26 (dd, 1H, J=1.3, 8.2 Hz, H-6), 7.15 (d, 1H, J=8.2 Hz, H-7), 3.95 (s, 3H, OCH$_3$), 3.77 (s, 2H, CH$_2$Ar), 3.72 (s, 3H, CO$_2$CH$_3$), 2.39 (s, 3H, COCH$_3$), 2.36 (s, 3H, SCH$_3$);
IR(KBr): δ ppm 2950, 1737, 1504, 1466, 1368, 1244, 1201, 1167, 1022 cm$^{-1}$;
MS (EI) m/z 400 [M$^+$].

Example 2

Methyl 3-[2-(4'-acetyloxy-3'-methoxyphenyl)-3-(methylthio)-benzofuran-5-yl]propionate (5b)

Through similar procedure to the method disclosed in Example 1, white solid type of methyl 3-[2-(4'-acetyloxy-3'-methoxyphenyl)-3-(methylthio)-benzofuran-5yl]propionate (5b; 9.87 g) showing following physicochemical property was obtained (yield: 84%).

m.p: 105° C.;
$^1$H NMR (CDCl$_3$): δ ppm 8.01 (d, 1H, J=1.8 Hz, H-2'), 7.92 (dd, 1H, J=1.8, 8.4 Hz, H-6), 7.53 (d, 1H, J=1.8 Hz, H-4), 7.42 (d, 1H, J=8.4 Hz, H-5), 7.18 (dd, 1H, J=1.8, 8.4 Hz, H-6), 7.14 (d, 1H, J=8.4 Hz, H-7), 3.95 (s, 3H, OCH$_3$), 3.69 (s, 3H, CO$_2$CH$_3$), 3.09 (t, 2H, J=7.5 Hz, MeO$_2$CCH$_2$), 2.71 (t, 2H, J=7.5 Hz, CH$_2$Ar), 2.38 (s, 3H, COCH$_3$), 2.35 (s, 3H, SCH$_3$);
IR (KBr): δ ppm 2947, 1764, 1736, 1601, 1500, 1468, 1369, 1242, 199, 1168, 1031 cm$^{-1}$;
MS (EI) m/z 414 [M$^+$].

Example 3

Methyl 2-[2-(4'-acetyloxy-3'-methoxyphenyl)-1-benzofuran-5-yl]acetate (6a)

305 mg of 2-[2-(4'-acetyloxy-3'-methoxyphenyl)-3-(methylthio)-benzofuran-5-yl]acetate (5a; 0.76 mM) dissolved in 2 ml of ethanol was reacted with Raney nickel for 2 hours at 60-65° C. The remaining agent was removed with filtration and then the solvent was removed.

The remaining residue was purified with Silica gel column chromatography with a mobile phase (n-hexane:ethylacetate=4:1) to obtain white solid type of methyl 2-[2-(4'-acetyloxy-3'-methoxyphenyl)-1-benzofuran-5yl]acetate (6a; 269 mg).

Yield: 92%;
m.p.: 99.9° C.;
$^1$H NMR (CDCl$_3$): δ ppm 7.42-7.48 (m, 4H, Ar), 7.20 (dd, 1H, J=1.8, 8.4 Hz, H-6), 7.11 (d, 1H, J=8.2 Hz, H-7), 6.96 (S, 1H, H-3), 3.95 (s, 3H, OCH$_3$), 3.72 (s, 2H, CH$_2$Ar), 3.71 (s, 3H, CO$_2$CH$_3$), 2.34 (s, 3H, COCH$_3$);
IR (KBr): δ ppm 1765, 1736, 1507, 1469, 1368, 1246, 1196, 1166, 1021 cm$^{-1}$;
MS (FAB) m/z 354 [M$^+$].

Example 4

Methyl 3-[2-(4'-acetyloxy-3'-methoxyphenyl)-benzofuran-5-yl]propionate (6b)

Through similar procedure to the method disclosed in Example 3, white solid type of methyl 3-[2-(4'-acetyloxy-3'-methoxyphenyl)-benzofuran-5-yl]propionate (6b; 8.62 g) showing following physicochemical property was obtained (yield: 94%).

m.p: 101.1° C.;
$^1$H NMR (CDCl$_3$): δ ppm 7.38-7.46 (m, 4H, Ar), 7.13 (dd, 1H, J=1.8, 8 Hz, H-6), 7.10 (d, 1H, J=8 Hz, H-7), 6.94 (d, 1H, J=0.9 Hz, H-3), 3.94 (s, 3H, OCH$_3$), 3.68 (s, 3H, CO$_2$CH$_3$), 3.05 (t, 2H, J=7.8 Hz, MeO$_2$CCH$_2$), 2.68 (t, 2H, J=7.8 Hz, CH$_2$Ar), 2.34 (s, 3H, COCH$_3$); IR (KBr): δ ppm 1765, 1735, 1607, 1505, 1470, 1245, 1196, 1121, 1028 cm$^{-1}$;
MS (EI) m/z 368 [M$^+$].

Example 5

2-[2-(4'-hydroxy-3'-methoxyphenyl)-3-(methylthio)-1-benzofuran-5-yl]acetate (7a)

7.58 g of 2-[2-(4'-acetyloxy-3'-methoxyphenyl)-3-(methylthio)-benzofuran-5-yl]acetate (5a; 18.92 mM) dissolved in 200 ml of THF was reacted with 100 ml of 1N lithium hydroxide. The reaction mixture was stirred for 2 hours at room temperature and the reacted product was acidified with diluted hydrochloric acid salt. The resulting product was extracted with ethylacetate, dried with anhydrous magnesium sulfate and the remaining solvent was removed.

The remaining residue was purified with Silica gel column chromatography with a mobile phase (n-hexane:ethylacetate=4:1) to obtain white solid type of 2-[2-(4'-hydroxy-3'-methoxyphenyl)-3-(methylthio)-1-benzofuran-5-yl]acetate (7a; 6.50 g).

Yield: 99%;
m.p: 197° C.;
$^1$H NMR (CDCl$_3$): δ ppm 7.85-7.9 (m, 2H, H-2' and H-6), 7.59 (d, 1H, J=1.8 Hz, H-4), 7.46 (d, 1H, J=8.3 Hz, H-5), 7.23 (dd, 1H, J=1.8, 8.3 Hz, H-6), 7.03 (d, 1H, J=8.3 Hz, H-7), 4.01 (s, 3H, OCH$_3$), 3.80 (s, 2H, CH$_2$Ar), 2.36 (s, 3H, SCH$_3$);
IR (KBr): δ ppm 3533, 3433, 1698, 1511, 1443, 1281, 1194, 1068 cm$^{-1}$; MS (EI) m/z 344 [M$^+$].

Example 6

3-[2-(4'-hydroxy-3'-methoxyphenyl)-3-(methylthio)-benzofuran-5-yl]propionate (7b)

Through similar procedure to the method disclosed in Example 5, white solid type of 3-[2-(4'-hydroxy-3'-methoxyphenyl)-3-(methylthio)-benzofuran-5-yl]propionate (7b; 3.84 g) showing following physicochemical property was obtained (yield: 94%).

m.p: 163.3° C.;
$^1$H NMR (CDCl$_3$): δ ppm 7.84-7.9 (m, 2H, H-2' and H-6'), 7.52 (d, 1H, J=1.7 Hz, H-4), 7.41 (d, 1H, J=8.4 Hz, H-5), 7.16 (dd, 1H, J=1.7, 8.4 Hz, H-6), 7.03 (d, 1H, J=8.4 Hz, H-7), 4.01 (s, 3H, OCH$_3$), 3.10 (t, 2H, J=7.7 Hz, HO$_2$CCH$_2$) 2.77 (t, 2H, J=7.7 Hz, CH$_2$Ar), 2.36 (s, 3H, SCH$_3$);
IR (KBr): δ ppm 3470, 2921, 1717, 1605, 1508, 1473, 1443, 1278, 1203, 1021 cm$^{-1}$;
MS (EI) m/z 358 [M$^+$].

Example 7

2-[2-(4'-hydroxy-3'-methoxyphenyl)-benzofuran-5-yl]acetate (8a)

Through similar procedure to the method disclosed in Example 5, white solid type of 2-[2-(4' hydroxy-3' methoxyphenyl)-benzofuran-5-yl]acetate (8a; 2.60 g) showing following physicochemical property was obtained (yield: 95%).

m.p: 111.5° C.;
$^1$H NMR (CDCl$_3$): δ ppm 7.28-7.45 (m, 4H, Ar), 6.81-6.85 (m, 2H, H-3 and H-7), 6.75 (dd, 1H, J=1.8, 8.2 Hz, H-6), 5.14 (s, 1H, OH), 3.88 (s, 3H, OCH$_3$), 3.58 (s, 2H, CH$_2$Ar);
IR (KBr): δ ppm 3433, 1703, 1518, 1461, 1413, 1330, 1264, 1224, 1139, 1025 cm$^{-1}$;
MS (FAB) m/z 298 [M$^+$]

Example 8

3-[2-(4'-hydroxy-3'-methoxyphenyl)-benzofuran-5-yl]propionic acid (8b)

Through similar procedure to the method disclosed in Example 5, white solid type of 3-[2-(4'-hydroxy-3'-methoxyphenyl)-benzofuran-5-yl]propionic acid (8b; 1.73 g) showing following physicochemical property was obtained (yield: 99%).

m.p.: 187.8° C.;
$^1$H NMR (CDCl$_3$): δ ppm 7.36-7.43 (m, 4H, Ar), 7.10 (dd, 1H, J=1.3, 8.3 Hz, H-7), 6.99 (d, 1H, J=8.1 Hz, H-3), 6.83 (s, 1H, H-6), 5.75 (s, 1H, OH), 4.01 (s, 3H, OCH$_3$), 3.06 (t, 2H, J=7.7 Hz, HO$_2$CCH$_2$), 2.74 (t, 2H, J=7.7 Hz, CH$_2$Ar);
IR (KBr): δ ppm 3420, 1692, 1506, 1429, 1255, 1214, 1119, 1018 cm$^{-1}$; MS (EI) m/z 312 [M$^+$].

Example 9

Methyl-2-[2-(4'-hydroxy-3'-methoxyphenyl)-3-(methylthio)-benzofuran-5-yl]acetate (9a)

The solution containing 98 mg of potassium carbonate (0.71 mM) dissolved in 2 ml of water was added to the solution containing 195.6 mg of 212-(4'-acetyloxy-3'-methoxyphenyl)-3-(methylthio)-benzofuran-5-yl)acetate (5a; 0.47 mM) dissolved in 5 ml of methanol at 0□. The reaction mixture was left alone at room temperature and stirred for 1 hour. The remaining solvent was removed. The resulting product was extracted with ethylacetate, dried with anhydrous magnesium sulfate and the remaining solvent was removed.

The remaining residue was purified with Silica gel column chromatography with a mobile phase (n-hexane:ethylacetate=4:1) to obtain white solid type of methyl 2-[2-(4'-hydroxy-3'-methoxyphenyl)-3-(methylthio)-benzofuran-5-yl]acetate (9a; 254 mg).

Yield: 94%;
m.p: 197° C.;
$^1$H NMR (CDCl$_3$): δ ppm 7.85-7.9 (m, 2H, H-2' and H-6), 7.58 (d, 1H, J=1.8 Hz, H-4), 7.44 (d, 1H, J=8.4 Hz, H-5, 7.23 (dd, 1H, J=1.8, 8.3 Hz, H-6), 7.03 (d, 1H, J=8.3 Hz, H-7), 5.82 (s, 1H, OH), 4.01 (s, 3H, OCH$_3$), 3.76 (s, 2H, CH$_2$Ar), 3.72 (s, 3H, CO$_2$CH$_3$), 2.37 (s, 3H, SCH$_3$);
IR (KBr): δ ppm 3430, 1735, 1607, 1505, 1468, 1257, 1202, 1027 cm$^{-1}$; MS (FAB) m/z 359 [MH$^+$].

Example 10

Methyl-3-[2-(4'-hydroxy-3'-methoxyphenyl)-3-(methylthio)-benzofuran-5-yl]propionate (9b)

Through similar procedure to the method disclosed in Example 9, white solid type of methyl 3-[2-(4'-hydroxy-3'-methoxyphenyl)-3-(methylthio)-benzofuran-5-yl]propionate (9b; 1.73 g) showing following physicochemical property was obtained (yield: 93%).

m.p: 82.8° C.;
$^1$H NMR (CDCl$_3$): δ ppm 7.85-7.9 (m, 2H, H-2' and H-6), 7.50 (d, 1H, J=1.8 Hz, H-4), 7.40 (d, 1H, J=8.4 Hz, H-5', 7.15 (dd, 1H, J=1.8, 8.4 Hz, H-6), 7.02 (d, 1H, J=8.4 Hz, H-7), 5.81 (s, 1H, OH), 4.01 (s, 3H, OCH$_3$), 3.69 (s, 3H, CO$_2$CH$_3$), 3.09 (t, 2H, J=7.5 Hz, MeO$_2$CCH$_2$), 2.71 (t, 2H, J=7.5 Hz, CH$_2$Ar), 2.37 (s, 3H, SCH$_3$);
IR (KBr): δ ppm 3433, 2924, 1733, 1601, 1504, 1467, 1256, 1201, 1030 cm$^{-1}$;
MS (FAB) m/z 372 [MH$^+$]

Example 11

Methyl 2-[2-(4'-hydroxy-3'-methoxyphenyl)-benzofuran-5-yl]acetate (10a)

Through similar procedure to the method disclosed in Example 9, white solid type of methyl 2-[2-(4'-hydroxy-3'- methoxyphenyl)-benzofuran-5-yl]acetate (10a; 265 mg) showing following physicochemical property was obtained (yield: 95%).

m.p: 132° C.;
$^1$H NMR (CDCl$_3$): δ ppm 7.34-7.45 (m, 4H, Ar), 7.15 (dd, 1H, J=1.7, 8.2 Hz, H-6), 6.98 (d, 1H, J=8.2 Hz, H-7), 6.83 (s, 1H, H-3), 3.99 (s, 3H, OCH$_3$), 3.70 (bs, 5H, CO$_2$CH$_3$ and CH$_2$Ar);
IR (KBr): δ ppm 3401, 2952, 1727, 1607, 1509, 1446, 1261, 1199, 1031 cm$^{-1}$;
MS (FAB) m/z 313 [MH$^+$].

Example 12

Methyl 3-[2-(4'-hydroxy-3'-methoxyphenyl)-benzofuran-5-yl]propionate (10b)

Through similar procedure to the method disclosed in Example 9, white solid type of methyl 3-[2-(4'-hydroxy-3'-methoxyphenyl)-benzofuran-5-yl]propionate (10b; 325 mg) showing following physicochemical property was obtained (yield: 92%).

m.p.: 124.0° C.;
$^1$H NMR (CDCl$_3$): δ ppm 7.34-7.42 (m, 4H, Ar), 7.08 (dd, 1H, J=1.7, 8 Hz, H-6), 6.98 (d, 1H, J=8 Hz, H-7), 6.83 (s, 1H, H-3), 5.75 (s, 1H, OH), 4.00 (s, 3H, OCH$_3$), 3.68 (s, 3H, CO$_2$CH$_3$), 3.04 (t, 2H, J=7.8 Hz, MeO$_2$CCH$_2$), 2.68 (t, 2H, J=7.8 Hz, CH$_2$Ar);
IR (KBr): δ ppm 3435, 1718, 1606, 1508, 1442, 1374, 1262, 1199, 1032 cm$^{-1}$;
MS (EI) m/z 326 [M$^+$].

Example 13

2-[2-(4'-hydroxy-3'-methoxyphenyl)-3-(methylthio)-benzofuran-5-yl]-1-ethanol (11a)

The suspension solution containing 68 mg of LAH (Lithium aluminum hydride; 1.8 m) dissolved in 1 ml of THF was added to the solution containing 300 mg of 2-[2-(4'-hydroxy-3'-methoxyphenyl)-3-(methylthio)-benzofuran-5-yl]acetate (9a; 1.8 mM) dissolved in 1 ml of THF. The reaction mixture was left alone at room temperature and stirred for 5 hours. The reacted product was cooled by adding 15 ml of water and 15 ml of 10% sulfuric acid slowly, extracted with diethyl ether, dried with anhydrous magnesium sulfate and the remaining solvent was removed.

The remaining residue was purified with Silica gel column chromatography with a mobile phase (n-hexane:ethylacetate=4:1) to obtain white solid type of 2-[2-(4'-hydroxy-3'-methoxyphenyl)-3-(methylthio)-benzofuran-5-yl]-1-ethanol (11a; 237 mg).

Yield: 55%;
m.p: 162.4° C.;
$^1$H NMR (CDCl$_3$): δ ppm 7.85-7.9 (m, 2H, H-2' and H-6'), 7.54 (d, 1H, J=1.8 Hz, H-4), 7.44 (d, 1H, J=8.3 Hz, H-5'), 7.17 (dd, 1H, J=1.8, 8.1 Hz, H-6), 7.03 (d, 1H, J=8.1 Hz, H-7), 4.01 (s, 3H, OCH$_3$), 3.93 (t, 2H, J=6.5 Hz, HOCH$_2$), 3.01 (t, 2H, J=6.5 Hz, CH$_2$Ar) 2.37 (s, 3H, SCH$_3$);
IR (KBr): δ ppm 3398, 2948, 1600, 1499, 1463, 1405, 1287, 1236, 1130, 1085, 1026 cm$^{-1}$;
MS (FAB) m/z 331 [MH$^+$].

Example 14

3-[2-(4'-hydroxy-3'-methoxyphenyl)-3-(methylthio)-benzofuran-5-yl]propanol (11b)

Through similar procedure to the method disclosed in Example 13, white solid type of 3-[2-(4'-hydroxy-3'-methoxyphenyl)-3-(methylthio)-benzofuran-5-yl]propanol (11b; 650 mg) showing following physicochemical property was obtained (yield: 51%).

m.p.: 106° C.;
$^1$H NMR (CDCl$_3$): δ ppm 7.75-7.82 (m, 2H, H-2' and H-6'), 7.42 (d, 1H, J=1.8 Hz, H-4), 7.32 (d, 1H, J=8.4 Hz, H-5'), 7.06 (dd, 1H, J=1.8, 8.4 Hz, H-6), 6.94 (d, 1H, J=8.4 Hz, H-7), 5.21 (s, 1H, OH), 3.92 (s, 3H, OCH$_3$), 3.64 (t, 2H, J=6.4 Hz, HOCH$_2$), 2.77 (t, 2H, J=7.5 Hz, CH$_2$Ar), 2.29 (s, 3H, SCH$_3$), 1.84-1.97 (m, 2H, HOCH$_2$CH$_2$);
IR (KBr): δ ppm 3393, 2936, 1602, 1505, 1467, 1277, 1127, 1034 cm$^{-1}$;
MS (FAB) m/z 344 [MH$^+$].

Example 15

2-[2-(4'-hydroxy-3'-methoxyphenyl)-benzofuran-5-yl]-1-ethanol (12a)

Through similar procedure to the method disclosed in Example 13, white solid type of 2-[2-(4'-hydroxy-3'-methoxyphenyl)-benzofuran-5-yl]-1-ethanol (12a; 365 mg) showing following physicochemical property was obtained (yield: 58%).

m.p.: 171.6° C.;
$^1$H NMR (CDCl$_3$): δ ppm 7.36-7.46 (m, 4H, Ar), 7.11 (dd, 1H, J=1.7, 8.2 Hz, H-6), 6.99 (d, 1H, J=8.2 Hz, H-7), 6.84 (s, 1H, H-3), 4.01 (s, 3H, OCH$_3$), 3.90 (t, 2H, J=6.5 Hz, HOCH$_2$), 2.96 (t, 2H, J=6.5 Hz, CH$_2$Ar);
IR (KBr): δ ppm 3431, 2952, 1732, 1608, 1510, 1469, 1261, 1201, 1024 cm$^{-1}$;
MS (FAB) m/z 285 [MH$^+$].

Example 16

3-[2-(4'-hydroxy-3'-methoxyphenyl)-benzofuran-5-yl]-1-propanol (12b)

Through similar procedure to the method disclosed in Example 13, white solid type of 3-[2-(4'-hydroxy-3'-methoxyphenyl)-benzofuran-5-yl]-1-propanol (12b; 410 mg) showing following physicochemical property was obtained (yield: 53%).

m.p.: 156.6° C.;
$^1$H NMR (CD$_3$OD): δ ppm 7.22-7.32 (m, 4H, Ar), 6.98 (dd, 1H, J=1.7, 8.3 Hz), 6.81 (d, 1H, J=0.7 Hz, H-3), 6.77 (d, 1H, J=8.3 Hz, H-7), 3.83 (s, 3H, OCH$_3$), 3.49 (t, 2H, J=6.4 Hz, HOCH$_2$), 2.65 (t, 2H, J=7.5 Hz, CH$_2$Ar), 1.72-1.82 (dt, 2H, HOCH$_2$CH$_2$);
IR (KBr): δ ppm 3444, 3123, 2932, 1606, 1514, 1419, 1276, 1239, 1130, 1047 cm$^{-1}$;
MS (EI) m/z 298 [M$^+$].

Example 17

2-[2-(3-methoxy-4-methoxymethoxy-phenyl)-3-methylsulfanyl-benzofuran-5-yl]-ethanol (13a)

650 mg of potassium carbonate (4.70 mM) and 329 mg of chloromethyl methyl ether (4.09 mM) were added to the solution containing 670 mg of 2-[2-(4'-hydroxy-3'-methoxyphenyl)-3-(methylthio)-benzofuran-5-yl]-1-ethanol (11a; 2.03 mM) dissolved in 35 ml of acetone. The reaction mixture was performed to reflux distillation for 4 hours and cooled to room temperature. The remaining potassium carbonate was removed with filtration and washing process and the filtrate was concentrated with vaccuo.

The remaining residue was purified with Silica gel column chromatography with a mobile phase (n-hexane:ethylacetate=4:1) to obtain white solid type of 2-[2-(3-methoxy-4-methoxymethoxy-phenyl)-3-methylsulfanyl-benzofuran-5-yl]-ethanol (13a; 605 mg).

Yield: 80%;
m.p.: 80-82° C.;
$^1$H NMR (CDCl$_3$): δ ppm 7.95 (d, 1H, J=1.8 Hz), 7.88 (dd, 1H, J=8.4, 2.0 Hz), 7.55 (d, 1H), 7.45 (d, 1H, J=8.3 Hz), 7.26 (d, 1H, J=8.6 Hz), 7.19 (dd, 1H, J=8.4, 1.4 Hz), 5.31 (s, 2H), 4.00 (s, 3H), 3.94 (m, 2H), 3.55 (s, 3H), 3.02 (t, 2H, J=6.1 Hz), 2.38 (s, 3H);
IR (KBr): δ ppm 3399, 2922, 1504, 1468, 1245, 1136, 1079, 990 cm$^{-1}$.

Example 18

3-[2-(3-methoxy-4-methoxymethoxy-phenyl)-3-methylsulfanyl-benzofuran-5-yl]-1-propan-1-ol (13b)

Through similar procedure to the method disclosed in Example 13, white solid type of 3-[2-(3-methoxy-4-methoxymethoxy-phenyl)-3-methylsulfanyl-benzofuran-5-yl]-1-propan-1-ol (13b; 1.97 g) showing following physicochemical property was obtained (yield: 91%).

m.p.: 60~64° C.;
$^1$H NMR (CD$_3$OD): δ ppm 7.94 (d, 1H, J=2.0 Hz), 7.87 (dd, 1H, J=8.4, 2.0 Hz), 7.51 (d, 1H), 7.42 (d, 1H, J=8.2 Hz), 7.26 (d, 1H, J=8.4 Hz), 7.16 (dd, 1H, J=8.4, 1.7 Hz), 5.31 (s, 2H), 4.00 (s, 3H), 3.75 (m, 2H), 3.55 (s, 3H), 2.86 (t, 2H, J=7.5 Hz), 2.38 (s, 3H), 1.98 (m, 2H);
IR (KBr): δ ppm 3396, 2924, 1504, 1468, 1245, 1136, 1079, 990 cm$^{-1}$.

Example 19

5-(2-methoxy-ethyl)-2-(3-methoxy-4-methoxymethoxy-phenyl)-3-methylsulfanyl-benzofuran (14a)

642 mg of hydride substance (16.1 mM) and 2.26 g of iodomethane (15.9 mM) were added to the solution containing 595 mg of 2-[2-(3-methoxymethoxy-phenyl)-3-methylsulfanyl-benzofuran-5-yl]-ethanol (13a; 1.59 mM) dissolved in 40 ml of THF. The reaction mixture was performed to reflux distillation for 16 hours and cooled to room temperature. The reaction mixture was extracted with 50 ml of water and ethylacetate to divide into water layer and organic solvent layer. The organic solvent layer was dried with magnesium sulfuric acid, filtrated and the filtrate was concentrated with vaccuo.

The remaining residue was purified with Silica gel column chromatography with a mobile phase (n-hexane:ethylacetate=4:1) to obtain white solid type of 5-(2-methoxy-ethyl)-2-(3-methoxy-4-methoxymethoxy-phenyl)-3-methylsulfanyl-benzofuran (14a; 410 mg).

Yield: 99%;
m.p.: 70° C.;
$^1$H NMR (CDCl$_3$): δ ppm 7.94 (d, 1H, J=2.01 Hz) 7.87 (dd, 1H, J=8.07 Hz & J=2.01 Hz), 7.53 (s, 1H,) 7.42 (d, 1H, J=8.43 Hz,), 7.26 (m, 1H) 7.19 (d, 1H, J=8.43 Hz, 5.29 (s, 2H), 4.0 (s, 3H), 3.67 (t, 2H, J=7.14 Hz), 3.55 (s, 3H), 3.39 (s, 3H), 3.02 (t, 2H, J=6.6 Hz), 2.38 (s, 3H);
IR (KBr): δ ppm 2923, 1736, 1605, 1504, 1467, 1245, 1114, 1080, 993, 886, 809 cm$^{-1}$;
MS (FAB+) m/z 388[M$^+$].

Example 20

2-(3-methoxy-4-methoxymethoxy-phenyl)-5-(3-methoxy-propyl)-3-methylsulfanyl-benzofuran (14b)

Through similar procedure to the method disclosed in Example 19, white solid type of 2-(3-methoxy-4-methoxymethoxy-phenyl)-5-(3-methoxy-propyl)-3-methylsulfanyl-benzofuran (14b; 1.86 g) showing following physicochemical property was obtained (yield: 96%).

m.p: 50~52° C.;
$^1$H NMR (CDCl$_3$): δ ppm 7.94 (d, 1H, J=2.0 Hz), 7.87 (dd, 1H, J=8.6, 2.0 Hz), 7.51 (d, 1H), 7.42 (d, 1H, J=8.3 Hz), 7.26 (d, 1H, J=8.4 Hz), 7.15 (dd, 1H, J=8.2, 1.7 Hz), 5.31 (s, 2H), 4.00 (s, 3H), 3.55 (s, 3H), 3.43 (t, 2H, J=6.4 Hz), 3.37 (s, 3H), 2.83 (t, 2H, J=7.3 Hz), 2.38 (s, 3H), 2.01-1.92 (m, 2H);
IR (KBr): δ ppm 2924, 1504, 1468, 1246, 1133, 1080, 992 cm$^{-1}$;
MS (FAB+) m/z 402[M$^+$].

Example 21

2-methoxy-4-[5-(2-methoxy-ethyl)-3-methylsulfanyl-benzofuran-2-yl]-phenol (15a)

The solution containing 590 mg of 5-(2-methoxy-ethyl)-2-(3-methoxy-4-methoxymethoxy-phenyl)-3-methylsulfanyl-benzofuran (14a; 1.52 mM) dissolved in 8 ml of dichloromethane was cooled to 0□. 4.0 ml of trifluoroacetic acid was added thereto and stirred for 40 mins at 0□. 7.5 g of solid sodium hydrogen carbonate and 60 ml of water were added thereto slowly at 0□. The reaction mixture was extracted with dichloromethane. The organic solvent layer was dried with magnesium sulfuric acid, filtrated and the filtrate was concentrated with vaccuo.

The remaining residue was purified with Silica gel column chromatography with a mobile phase (n-hexane:ethylacetate=4:1) to obtain white solid type of 2-methoxy-4-[5-(2-methoxy-ethyl)-3-methylsulfanyl-benzofuran-2-yl]-phenol (15a; 455 mg).

Yield: 87%;
m.p.: 67° C.;
$^1$H NMR (CDCl$_3$): δ ppm 7.87-7.84 (m, 2H), 7.52 (d, 1H, J=1.29 Hz), 7.40 (d, 1H, J=8.25 Hz), 7.16 (dd, 1H, J=8.4 & 1.65 Hz), 7.01 (d, 1H, J=8.07), 6.0 (s, 1H), 3.98 (s, 3H), 3.67 (t, 2H, J=7.14 Hz), 3.39 (s, 3H), 3.02 (t, 2H, J=6.96), 2.37 (s, 3H);
IR (KBr): δ ppm 3398, 2923, 1603, 1505, 1468, 1256, 1200, 1113, 1033, 969, 861, 813 cm$^{-1}$;
MS (FAB+) m/z 344 [M$^+$].

Example 22

2-methoxy-4-[5-(3-methoxy-propyl)-3-methylsulfanyl-benzofuran-2-yl]-phenol (15b)

Through similar procedure to the method disclosed in Example 21, white solid type of 2-methoxy-4-[5-(3-methoxy-propyl)-3-methylsulfanyl-benzofuran-2yl]-phenol (15b; 1.22 g) showing following physicochemical property was obtained (yield: 75%).

m.p.: 57~59° C.;
$^1$H NMR (CDCl$_3$): δ ppm 7.88~7.85 (m, 2H), 7.49 (d, 1H), 7.40 (d, 1H, J=8.3 Hz,), 7.14 (dd, 1H, J=8.3, 1.8 Hz), 7.03 (d, 1H, J=8.4 Hz), 5.82 (s, OH), 4.01 (s, 3H), 3.43 (t, 2H, J=6.4 Hz), 3.37 (s, 3H), 2.82 (t, 2H, J=7.4 Hz), 2.37 (s, 3H), 2.01-1.92 (m, 2H);

IR (KBr): δ ppm 3396, 2923, 1505, 1468, 1256, 1201, 1118 $cm^{-1}$;

MS (FAB+) m/z 358 [$M^+$].

Example 23

2-methoxy-4-[5-(2-methoxy-ethyl)-benzofuran-2-yl]-phenol (16a)

Through similar procedure to the method disclosed in Example 3, white solid type of 2-methoxy-4-[5-(2-methoxy-ethyl)-benzofuran-2-yl]-phenol (16a; 330 mg) showing following physicochemical property was obtained (yield: 94%).

m.p: 180° C.;

$^1$H NMR (CDCl$_3$): δ ppm d 7.87-7.84 (m, 2H), 7.52 (d, 1H, J=1.29 Hz), 7.40 (d, 1H, J=8.25 Hz), 7.16 (dd, 1H, J=8.4 & 1.65 Hz), 7.01 (d, 1H, J=8.07 Hz), 6.0 (s, 1H), 3.98 (s, 3H), 3.67 (t, 2H, J=7.14), 3.39 (s, 3H), 3.02 (t, 2H, J=6.96 Hz), 2.37 (s, 3H);

IR (KBr): δ ppm 3395, 2928, 1725, 1609, 1509, 1469, 1257, 1200, 1116, 1030, 995, 862, 805 $cm^{-1}$;

MS (FAB+) m/z 298 [$M^+$].

Example 24

2-methoxy-4-[5-(3-methoxy-propyl)-benzofuran-2-yl]-phenol (16b)

Through similar procedure to the method disclosed in Example 21, white solid type of 2-methoxy-4-[5-(3-methoxy-propyl)-benzofuran-2-yl]-phenol (16b; 750 mg) showing following physicochemical property was obtained (yield: 96%).

m.p.: 76~78° C.;

$^1$H NMR (CDCl$_3$): δ ppm 7.41-7.36 (m, 4H), 7.09 (dd, 1H), 6.98 (d, 1H, J=8.0 Hz), 6.83 (s, 1H), 5.75 (s, OH), 4.00 (s, 3H), 3.41 (t, 2H, J=6.4 Hz), 3.36 (s, 3H), 2.78 (t, 2H, J=7.0 Hz), 1.98-1.91 (m, 2H);

IR (KBr): δ ppm 3396, 2925, 1609, 1510, 1469, 1257, 1201, 1119 $cm^{-1}$;

MS (FAB+) m/z 312 [$M^+$].

Example 25

2-(3,4-dimethoxy-phenyl)-5-(2-methoxy-ethyl)-3-methylsulfanyl-benzofuran (17a)

Through similar procedure to the method disclosed in Example 19, white solid type of 2-(3,4-dimethoxy-phenyl)-5-(2-methoxy-ethyl)-3-methylsulfanyl-benzofuran (17a; 674 mg) showing following physicochemical property was obtained (yield: 93.3%).

m.p.: 61° C.;

$^1$H NMR (CDCl$_3$): δ ppm 7.92 (s, 1H), 7.89 (d, 1H, J=2.0 Hz), 7.53 (s, 1H), 7.42 (d, 1H, J=8.22 Hz), 7.17 (dd, 1H, J=8.43 & 2.01 Hz), 6.98 (d, 1H, J=8.04), 4.0 (s, 3H), 3.96 (s, 3H), 3.67 (t, 2H, J=7.14 Hz), 3.39 (s, 3H), 3.02 (t, 2H, J=6.96 Hz), 2.38 (s, 3H);

IR (KBr): δ ppm 2923, 2855, 1507, 1464, 1255, 1144, 1113, 1027, 807 $cm^{-1}$;

MS (FAB+) m/z 358 [$M^+$].

Example 26

2-(3,4-dimethoxy-phenyl)-5-(3-methoxy-propyl)-3-methylsulfanyl-benzofuran (17b)

Through similar procedure to the method disclosed in Example 19, white solid type of 2-(3,4-dimethoxy-phenyl)-5-(3-methoxy-propyl)-3-methylsulfanyl-benzofuran (17b; 3.75 g) showing following physicochemical property was obtained (yield: 99.5%).

m.p.: 68~70° C.;

$^1$H NMR (CDCl$_3$): δ ppm 7.92-7.89 (m, 2H), 7.50 (s, 1H), 7.41 (d, 1H, J=8.4 Hz), 7.15 (d, 1H, J=7.7 Hz), 6.98 (d, 1H, J=8.5 Hz), 4.01 (s, 3H), 3.96 (s, 3H), 3.43 (t, 2H, J=6.2 Hz), 3.37 (s, 3H), 2.83 (t, 2H, J=7.5 Hz), 2.38 (s, 3H), 1.97 (m, 2H);

IR (KBr): δ ppm 2925, 1605, 1506, 1467, 1254, 1145, 1118, 1027 $cm^{-1}$;

MS (FAB+) m/z 372 [$M^+$].

Example 27

2-(3,4-dimethoxy-phenyl)-5-(2-methoxy-ethyl)-benzofuran (18a)

Through similar procedure to the method disclosed in Example 19, white solid type of 2-(3,4-dimethoxy-phenyl)-5-(2-methoxy-ethyl)-benzofuran (18a; 486 mg) showing following physicochemical property was obtained (yield: 95.3%).

m.p.: 81° C.;

$^1$H NMR (CDCl$_3$): δ ppm 7.43-7.36 (m, 4H), 7.14 (dd, 1H, J=8.25 & Hz J=1.65 Hz), 6.93 (d, 1H, J=8.43 Hz), 6.85 (s, 1H), 3.99 (s, 3H), 3.93 (s, 3H), 3.64 (t, 2H, J=7.14 Hz), 3.38 (s, 3H), 2.97 (t, 2H, J=6.96 Hz);

IR (KBr): δ ppm 2924, 2855, 1730, 1608, 1511, 1463, 1377, 1255, 1115, 1028, 861, 804 $cm^{-1}$;

MS (FAB+) m/z 312 [$M^+$].

Example 28

2-(3,4-dimethoxy-phenyl)-5-(3-methoxy-propyl)-benzofuran (18b)

Through similar procedure to the method disclosed in Example 19, pale yellow solid type of 2-(3,4-dimethoxy-phenyl)-5-(3-methoxy-propyl)-benzofuran (18b; 2.65 g) showing following physicochemical property was obtained (yield: 97.7%).

m.p: 93~95° C.;

$^1$H NMR (CDCl$_3$): δ ppm 7.45-7.36 (m, 4H), 7.09 (dd, 1H, J=8.3, 1.7 Hz), 6.94 (d, 1H, J=8.6 Hz), 6.86 (d, 1H, J=0.7 Hz), 4.00 (s, 3H), 3.94 (s, 3H), 3.41 (t, 2H, J=6.2 Hz), 3.36 (s, 3H), 2.78 (t, 2H, J=7.3 Hz), 1.99-1.89 (m, 2H);

IR (KBr): δ ppm 2927, 1608, 1511, 1468, 1254, 1170, 1119, 1026 $cm^{-1}$; MS (FAB+) m/z 326

Example 29

Benzyl 2-[2-(4'-hydroxy-3'-methoxyphenyl)-3-(methylthio)-benzofuran-5-yl]-acetate (19a)

Benzyl alcohol was added to the solution containing 128 mg of 2-[2-(4'-hydroxy-3'-methoxyphenyl)-3-(methylthio)-1-benzofuran-5-yl]acetate (7a; 0.37 mM) dissolved in 4 ml of dimethylformamide and the solution was cooled to 0□. 107 mg of ethylene dichloride (0.56 mM) was added thereto and then dimethylaminopyridine was added thereto as a catalyst. The solution was heated for overnight at 120□. The reaction mixture was extracted with diethylether. The organic solvent layer was dried with magnesium sulfuric acid, filtrated and the filtrate was concentrated with vaccuo.

The remaining residue was purified with Silica gel column chromatography with a mobile phase (n-hexane:ethylacetate=4:1) to obtain white solid type of benzyl 2-[2-(4'-hydroxy-3'-methoxyphenyl)-3-(methylthio)-benzofuran-5-yl]-acetate (19a; 160 mg).

Yield: 98%;
m.p: 94.2° C.;
$^1$H NMR (CDCl$_3$): δ ppm 7.85-7.9 (m, 2H, H-2' and H-6'), 7.60 (d, 1H, J=1.8 Hz, H-4), 7.44 (d, 1H, J=8.4 Hz, H-5', 7.3°). 4 (m, 5H, Ph), 7.23 (dd, 1H, J=1.8, 8.4 Hz, H-6), 7.03 (d, 1H, J=8.4 Hz, H-7), 5.83 (s, 1H, OH), 5.16 (s, 2H, PhCH$_2$CO), 4.01 (s, 3H, OCH$_3$), 3.80 (s, 2H, CH$_2$Ar), 2.34 (s, 3H, SCH$_3$);
IR (KBr): δ ppm 3443, 2924, 1732, 1602, 1505, 1467, 1257, 1080, 1029 cm$^{-1}$;
MS (FAB) m/z 435 [MH$^+$].

Example 30

Benzyl 2-[2-(4'-hydroxy-3'-methoxyphenyl)-3-(methylthio)-benzofuran-5yl]propionate (19b)

Through similar procedure to the method disclosed in Example 29, white solid type of benzyl 2-[2-(4'-hydroxy-3'-methoxyphenyl)-3-(methylthio)-benzofuran-5yl]propionate (19b; 145 mg) showing following physicochemical property was obtained (yield: 97%).

m.p: 87° C.;
$^1$H NMR (CDCl$_3$): δ ppm 7.84-7.9 (m, 2H, H-2' and H-6'), 7.49 (d, 1H, J=1.8 Hz, H-4), 7.38 (d, 1H, J=8.4 Hz, H-5', 7.3-7.4 (m, 5H, Ph), 7.13 (dd, 1H, J=1.8, 8 Hz, H-6), 7.02 (d, 1H, J=8 Hz, H-7), 5.82 (s, 1H, OH), 5.12 (s, 2H, PhCH$_2$CO), 4.01 (s, 3H, OCH$_3$), 3.11 (t, 2H, J=7.7 Hz, MeO$_2$CCH$_2$), 2.76 (t, 2H, J=7.7 Hz, CH$_2$Ar), 2.34 (s, 3H, SCH$_3$);
IR (KBr): δ ppm 3397, 2928, 1732, 1649, 1506, 1462, 1258, 1080, 1030 cm$^{-1}$;
MS (FAB) m/z 449 [MH$^+$].

Example 31 pentafluorophenyl 2-[2-(4'-hydroxy-3'-methoxyphenyl)-3-(methylthio)-benzofuran-5-yl]-acetate (20a)

95.55 mg of pentafluorophenol (0.52 mM) was added to the solution containing 154.7 mg of 2-[2-(4'-hydroxy-3'-methoxyphenyl)-3-(methylthio)-1-benzofuran-5-yl]acetate (7a; 0.52 mM) dissolved in 2 ml of dichloromethane added with 2 drops of dimethylformamide and the solution was cooled to 0□. 107 mg of ethylene dichloride (0.56 mM) was added thereto and then the solution was left alone at room temperature. The reaction mixture was extracted with dichloromethane. The organic solvent layer was dried with magnesium sulfuric acid, filtrated and the filtrate was concentrated with vaccuo.

The remaining residue was purified with Silica gel column chromatography with a mobile phase (n-hexane:ethylacetate=4:1) to obtain white solid type of pentafluorophenyl 2-[2-(4'-hydroxy-3'-methoxyphenyl)-3-(methylthio)-benzofuran-5-yl]-acetate (20a; 241 mg).

Yield: 81%;
m.p: 109° C.;
$^1$H NMR (CDCl$_3$): δ ppm 7.85-7.92 (m, 2H, H-2' and H-6'), 7.67 (d, 1H, J=1.8 Hz, H-4), 7.50 (d, 1H, J=8.3 Hz, H-5'), 7.28 (dd, 1H, J=1.8, 7.9 Hz, H-6), 7.04 (d, 1H, J=7.9 Hz, H-7), 5.83 (s, 1H, OH), 4.10 (s, 3H, OCH$_3$), 4.02 (s, 2H, ArO$_2$CCH$_2$), 2.38 (s, 3H, SCH$_3$).

Example 32

Pentafluorophenyl 3-[2-(4'-hydroxy-3'-methoxyphenyl)-3-(methylthio)-benzofuran-5-yl]propionate (20b)

Through similar procedure to the method disclosed in Example 31, white solid type of Pentafluorophenyl 3-[2-(4'-hydroxy-3'-methoxyphenyl)-3-(methylthio)-benzofuran-5-yl]propionate (20b; 180 mg) showing following physicochemical property was obtained (yield: 85%).

m.p: 141° C.;
$^1$H NMR (CDCl$_3$): δ ppm 7.85-7.92 (m, 2H, H-2' and H-6'), 7.56 (d, 1H, J=1.8 Hz, H-4), 7.44 (d, 1H, J=8.2 Hz, H-5'), 7.19 (dd, 1H, J=1.8, 8.3 Hz, H-6), 7.03 (d, 1H, J=8.3 Hz, H-7), 4.01 (s, 3H, OCH$_3$), 3.23 (t, 2H, J=7.4 Hz, ArO$_2$CCH$_2$), 3.07 (t, 2H, J=7.4 Hz, CH$_2$Ar), 2.37 (s, 3H, SCH$_3$).

Example 33

Pentafluorophenyl 2-[2-(4'-hydroxy-3'-methoxyphenyl)-benzofuran-5-yl]acetate (21a)

Through similar procedure to the method disclosed in Example 31, white solid type of Pentafluorophenyl 2-[2-(4'-hydroxy-3'-methoxyphenyl)-benzofuran-5-yl]acetate (21a; 684 mg) showing following physicochemical property was obtained (yield: 88%).

m.p: 140.2° C.;
$^1$H NMR (CDCl$_3$): δ ppm 7.54 (bs, 1H, H-2'), 7.50 (bd, 1H, H-6'), 7.35-7.42 (m, 2H, H-5' and H-4), 7.24 (dd, 1H, J=1.8, 8.3 Hz, H-6), 7.00 (d, 1H, J=8.3 Hz, H-7), 6.88 (s, 1H, H-3), 5.76 (s, 1H, OH), 4.05 (s, 2H, ArO$_2$CCH$_2$), 4.01 (s, 3H, OCH$_3$).

Example 34

Pentafluorophenyl 3-[2-(4'-hydroxy-3'-methoxyphenyl)-benzofuran-5-yl]propionate (21b)

Through similar procedure to the method disclosed in Example 31, white solid type of Pentafluorophenyl 3-[2-(4'-hydroxy-3'-methoxyphenyl)-benzofuran-5-yl]propionate (21b; 1.21 g) showing following physicochemical property was obtained (yield: 87%).

m.p: 138° C.;
$^1$H NMR (CDCl$_3$): δ ppm 7.35-7.46 (m, 4H, Ar), 7.13 (dd, 1H, J=1.7, 8.3 Hz, H-6), 6.99 (d, 1H, J=8.3 Hz, H-7), 6.85 (s, 1H, H-3), 5.76 (s, 1H, OH), 4.01 (s, 3H, OCH$_3$), 3.18 (t, 2H, J=7.4 Hz, ArO$_2$CCH$_2$), 3.03 (t, 2H, J=7.4 Hz, CH$_2$Ar).

Example 35

N,N-diethyl 2-[2-(4'-hydroxy-3'-methoxyphenyl)-3-(methylthio)-benzofuran-5-yl]acetamide (22a)

0.06 ml of diethylamine (0.6 mM) was added to the solution containing 213 mg of pentafluorophenyl 2-[2-(4'-hydroxy-3'-methoxyphenyl)-3-(methylthio)-benzofuran-5-yl]-acetate (20a; 0.4 mM) dissolved in 0.6 ml of dichloromethane and the solution was cooled to 0° C. The reaction mixture was left alone at room temperature and stirred for 1 hour. The organic solvent was removed and the remaining residue was purified with Silica gel column chromatography with a mobile phase (dichloromethane:methanol=8:1) to obtain white solid type of N,N-diethyl 2-[2-(4'-hydroxy-3'-methoxyphenyl)-3-(methylthio)-benzofuran-5-yl]acetamide (22a; 160 mg).

Yield: 65%;

m.p: 167° C.;

$^1$H NMR (CDCl$_3$): δ ppm 7.85-7.9 (m, 2H, H-2' and H-6'), 7.55 (d, 1H, J=1.5 Hz, H-4), 7.43 (d, 1H, J=8.1 Hz, H-5'), 7.22 (dd, 1H, J=1.5, 8.3 Hz, H-6), 7.02 (d, 1H, J=8.3 Hz, H-7), 5.82 (s, 1H, OH), 4.01 (s, 3H, OCH$_3$), 3.83 (s, 2H, CH$_2$Ar), 3.39 (dq, 4H, (CH$_3$CH$_2$)$_2$N), 2.36 (s, 3H, SCH$_3$), 1.14 (dd, 6H, (CH$_3$CH$_2$)$_2$N);

IR (KBr): δ ppm 3427, 2482, 1646, 1502, 1469, 1243, 1162, 1006 cm$^{-1}$;

MS (FAB) m/z 400 [MH$^+$].

Example 36

N,N-dimethyl 2-[2-(4'-hydroxy-3'-methoxyphenyl)-3-(methylthio)-benzofuran-5-yl]acetamide (22b)

2 N diethylamine dissolved in 0.2 ml of methanol (0.38 mM) was added to the solution containing 127 mg of pentafluorophenyl 2-[2-(4'-hydroxy-3'-methoxyphenyl)-3-(methylthio)-benzofuran-5-yl]-acetate (20a; 0.38 mM) dissolved in 2 ml of methanol cooled to −78° C. The reaction mixture was heat at 80° C. and stirred for 2 hours. The organic solvent was removed and the remaining residue was purified with Silica gel column chromatography with a mobile phase (dichloromethane:methanol=8:1) to obtain white solid type of N,N-dimethyl 2-[2-(4'-hydroxy-3'-methoxyphenyl)-3-(methylthio)-benzofuran-5-yl]acetamide (22b; 92 mg).

Yield: 98%;

m.p: 134.9° C.;

$^1$H NMR (CDCl$_3$): δ ppm 7.83-7.9 (m, 2H, H-2' and H-6'), 7.55 (d, 1H, J=1.8 Hz, H-4), 7.43 (d, 1H, J=8.4 Hz, H-5'), 7.21 (dd, 1H, J=1.8, 8.4 Hz, H-6), 7.01 (d, 1H, J=8.4 Hz, H-7), 5.89 (s, 1H, OH), 4.01 (s, 3H, OCH$_3$), 3.85 (s, 2H, CH$_2$Ar), 3.05 (s, 3H, (CH$_3$)$_2$N), 3.00 (s, 3H, (CH$_3$)$_2$N), 2.35 (s, 3H, SCH$_3$);

IR (KBr): δ ppm 2925, 1631, 1504, 1466, 1279, 1129, 1031 cm$^{-1}$;

MS (EI) m/z 371 [M$^+$].

Example 37

N-methyl 2-[2-(4'-hydroxy-3'-methoxyphenyl)-3-(methylthio)-benzofuran-5-yl]acetamide (22c)

Through similar procedure to the method disclosed in Example 36, white solid type of N-methyl. 2-[2-(4'-hydroxy-3'-methoxyphenyl)-3-(methylthio)-benzofuran-5-yl]acetamide (22c; 157 mg) showing following physicochemical property was obtained (yield: 60%).

m.p: 157.5° C.;

$^1$H NMR (CDCl$_3$): δ ppm 7.86-7.9 (m, 2H, H-2' and H-6'), 7.56 (d, 1H, J=1.8 Hz, H-4), 7.48 (d, 1H, J=8.4 Hz, H-5'), 7.19 (dd, 1H, J=1.8, 8.1 Hz, H-6), 7.04 (d, 1H, J=8.1 Hz, H-7), 5.38 (bs, 1H, NH), 4.02 (s, 3H, OCH$_3$), 3.72 (s, 2H, CH$_2$Ar), 2.77 (d, 3H, J=4.95 Hz, CH$_3$NH), 2.37 (s, 3H, SCH$_3$);

IR (KBr): δ ppm 3742, 1646, 1507, 1465, 1279 cm$^{-1}$;

MS (EI) m/z 357 [M$^+$].

Example 38

2-[2-(4'-hydroxy-3'-methoxyphenyl)-3-(methylthio)-benzofuran-5-yl]-1-morpholino-1-ethanone (22d)

0.04 ml of morpholine (0.4 mM) was added to the solution containing 137 mg of pentafluorophenyl 2-[2-(4'-hydroxy-3'-methoxyphenyl)-3-(methylthio)-benzofuran-5-yl]-acetate (20a; 0.27 mM) dissolved in 2 ml of dichloromethane. The reaction mixture was stirred for 1 hour and the solvent was removed. The remaining residue was purified with Silica gel column chromatography with a mobile phase (dichloromethane:methanol=8:1) to obtain white solid type of 2-[2-(4'-hydroxy-3'-methoxyphenyl)-3-(methylthio)-benzofuran-5-yl]-1-morpholino-1-ethanone (22d; 112 mg).

Yield: 55%;

m.p: 170.5° C.;

$^1$H NMR (CDCl$_3$): δ ppm 7.85-7.9 (m, 2H, H-2' and H-6'), 7.53 (d, 1H, J=1.5 Hz, H-4), 7.45 (d, 1H, J=8.4 Hz, H-5'), 7.19 (dd, 1H, J=1.5, 8 Hz, H-6), 7.02 (d, 1H, J=8 Hz, H-7), 5.84 (s, 1H, OH), 4.01 (s, 3H, OCH$_3$), 3.86 (s, 2H, CH$_2$Ar), 3.67 (s, 4H, CH$_2$OCH$_2$), 3.50 (s, 4H, CH$_2$NCH$_2$), 2.35 (s, 3H, SCH$_3$);

IR (KBr): δ ppm 3280, 2920, 1633, 1505, 1464, 1276, 1117, 1034 cm$^{-1}$;

MS (FAB) m/z 414 [MH$^+$].

Example 39

2-[2-(4'-hydroxy-3'-methoxyphenyl)-3-(methylthio)-benzofuran-5-yl]-1-piperazino-1-ethanone (22e)

0.09 ml of 1-benzyl piperazine (0.52 mM) was added to the solution containing 17.88 mg of pentafluorophenyl 2-[2-(4'-hydroxy-3'-methoxyphenyl)-3-(methylthio)-benzofuran-5-yl]-acetate (20a; 0.21 mM) dissolved in 1 ml of dimethyl sulfoxide. The reaction mixture was stirred for 10 minutes and the solvent was removed. The remaining residue was purified with Silica gel column chromatography with a mobile phase (dichloromethane:methanol=8:1) to obtain white solid type of 2-[2-(4'-hydroxy-3'-methoxyphenyl)-3-(methylthio)-benzofuran-5-yl]-1-piperazino-1-ethanone (22e; 87 mg).

Yield: 63%;

m.p: 88.5° C.;

$^1$H NMR (CDCl$_3$): δ ppm 7.85-7.9 (m, 2H; H-2' and H-6'), 7.54 (d, 1H, J=2 Hz, H-4), 7.44 (d, 1H, J=8.4 Hz, H-5'), 7.20 (dd, 1H, J=2, 8.4 Hz, H-6), 7.02 (d, 1H, J=8.4 Hz, H-7), 4.01 (s, 3H, OCH$_3$), 3.86 (s, 2H, CH$_2$Ar), 3.67 (bt, 2H, CH$_2$N(C=O)CH$_2$), 3.49 (bt, 2H, CH$_2$N(C=O)CH$_2$), 2.85 (s, 2H, CH$_2$NHCH$_2$), 2.69 (s, 2H, CH$_2$NHCH$_2$), 2.35 (s, 3H, SCH$_3$);

IR (KBr): δ ppm 2921, 1631, 1504, 1463, 1279, 1127, 1030 cm$^{-1}$;

MS (FAB) m/z 413 [MH$^+$].

Example 40

2-[2-(4'-hydroxy-3'-methoxyphenyl)-3-(methylthio)-benzofuran-5-yl]-1-(4-benzylpiperazino)-1-ethanone (22f)

0.09 ml of 1-benzyl piperazine (0.52 mM) was added to the solution containing 132 mg of pentafluorophenyl 2-[2-(4'-hydroxy-3'-methoxyphenyl)-3-(methylthio)-benzofuran-5-yl]-acetate (20a; 0.26 mM) dissolved in 2 ml of dichloromethane. The reaction mixture was stirred for 1 hour and the solvent was removed. The remaining residue was purified with Silica gel column chromatography with a mobile phase (dichloromethane:methanol=8:1) to obtain white solid type of 2-[2-(4'-hydroxy-3'-methoxyphenyl)-3-(methylthio)-benzofuran-5-yl]-1-(4-benzylpiperazino)-1-ethanone (22f; 130 mg).

Yield: 34%;
m.p: 69.1° C.;
$^1$H NMR (CDCl$_3$): δ ppm 7.85-7.9 (m, 2H, H-2' and H-6'), 7.52 (bs, 1H, H-4), 7.42 (d, 1H, J=8.4 Hz, H-5'), 7.24-7.3 (m, 5H, Ph), 7.17 (dd, 1H, J=1.8, 8 Hz, H-6), 7.02 (d, 1H, J=8 Hz, H-7), 4.01 (s, 3H, OCH$_3$), 3.85 (s, 2H, CH$_2$Ar), 3.69 (bt, 2H, CH$_2$N(C=O)CH$_2$), 3.50 (bt, 2H, CH$_2$N(C=O)CH$_2$), 3.48 (s, 2H, PhCH$_2$N), 2.44 (s, 2H, CH$_2$NCH$_2$), 2.35 (s, 3H, SCH$_3$), 2.28 (s, 2H, CH$_2$NCH$_2$);
IR (KBr): δ ppm 2921, 1638, 1506, 1462, 1279, 1128 cm$^{-1}$;
MS (FAB) m/z 503 [MH$^+$].

Example 41

2-[2-(4'-hydroxy-3'-methoxyphenyl)-3-(methylthio)-benzofuran-5-yl]-1-(4-benzylpiperidino)-1-ethanone (22 g)

0.035 ml of 4-benzyl piperidine (0.2 mM) was added to the solution containing 103 mg of pentafluorophenyl 2-[2-(4'-hydroxy-3'-methoxyphenyl)-3-(methylthio)-benzofuran-5-yl]-acetate (20a; 0.2 mM) dissolved in 2 ml of dichloromethane. The reaction mixture was stirred for 30 mins and the solvent was removed. The remaining residue was purified with Silica gel column chromatography with a mobile phase (dichloromethane:methanol=8:1) to obtain white solid type of 2-[2-(4'-hydroxy-3'-methoxyphenyl)-3-(methylthio)-benzofuran-5-yl]-1-(4-benzylpiperidino)-1-ethanone (22 g; 101 mg).

Yield: 65%;
m.p: 206.8° C.;
$^1$H NMR (CDCl$_3$): δ ppm 7.85-7.9 (m, 2H, H-2' and H-6'), 7.53 (d, 1H, J=1.5 Hz, H-4), 7.42 (d, 1H, J=8.4 Hz, H-5'), 7.05-7.3 (m, 6H, Ph and H-6), 7.02 (d, 1H, J=8.4 Hz, H-7), 5.82 (bs, 1H, OH), 4.66 (m, 1H, CH$_2$NCH$_2$), 4.01 (s, 3H, OCH$_3$), 3.92 (m, 1H, CH$_2$NCH$_2$), 3.85 (s, 2H, CH$_2$Ar), 2.93 (m, 1H, CH$_2$NCH$_2$), 2.45-2.6 (m, 3H, CH$_2$NCH$_2$ and PhCH$_2$), 2.35 (s, 3H, SCH$_3$), 1.58-1.72 (m, 4H, CH$_2$CH$_2$NCH$_2$CH$_2$), 0.9-1.3 (m, 1H, BnCH);
IR (KBr): δ ppm 2922, 1618, 1507, 1461, 1278, 1028 cm$^{-1}$;
MS (FAB) m/z 502 [MH$^+$].

Example 42

(R)-3-(2-[2-(4-hydroxy-3-methoxyphenyl)-3-(methylsulfanyl)-1-benzofuran-5-yl]acetylamino-4-methyl pentanamide (22 h)

0.04 ml of triethylamine (0.4 mM) and 32 mg of L-Leucinamide hydrochloride (0.4 mM) was added to the solution containing 98.8 mg of pentafluorophenyl 2-[2-(4'-hydroxy-3'-methoxyphenyl)-3-(methylthio)-benzofuran-5-yl]-acetate (20a; 0.4 mM) dissolved in 2 ml of dimethylformamide. The reaction mixture was stirred for 30 mins and the solvent was removed. The remaining residue was purified with Silica gel column chromatography with a mobile phase (dichloromethane:methanol=8:1) to obtain white solid type of (R)-3-(2-[2-(4-hydroxy-3-methoxyphenyl)-3-(methylsulfanyl)-1-benzofuran-5-yl]acetylamino-4-methyl pentanamide (22 h; 91 mg).

Yield: 98%;
m.p: 220.1° C.;
$^1$H NMR (CD$_3$OD): δ ppm 7.94 (d, 1H, J=1.8 Hz, H-2'), 7.77 (dd, 1H, J=1.8, 8.4 Hz, H-6'), 7.62 (d, 1H, J=1.5 Hz, H-4), 7.43 (d, 1H, J=8.4 Hz, H-5', 7.25 (dd, 1H, J=1.5, 8.4 Hz, H-6), 6.90 (d, 1H, J=8.4 Hz, H-7), 5.48 (bs, 1H, OH), 4.41 (m, 1H, CHNH), 3.94 (s, 3H, OCH$_3$), 3.68 (dd of AB, 2H, J=14, 21 Hz, CH$_2$Ar), 2.36 (s, 3H, SCH$_3$), 1.55-1.7 (m, 3H, CHMe$_2$ and CH$_2$CONH$_2$), 0.9 (dd, 6H, J=6, 16.5 Hz, CH(CH$_3$)$_2$);
IR (KBr): δ ppm 3855, 3742, 2955, 1651, 1541, 1509, 1464, 1278 cm$^{-1}$; MS (FAB) m/z 457 [MH$^+$], 479 [MNa$^+$].

Example 43

N-phenyl 2-[2-(4'-hydroxy-3'-methoxyphenyl)-3-(methylthio)-benzofuran-5-yl]acetamide (22i)

0.05 ml of aniline (0.5 mM) was added to the solution containing 170.6 mg of pentafluorophenyl 2-[2-(4'-hydroxy-3'-methoxyphenyl)-3-(methylthio)-benzofuran-5-yl]-acetate (20a; 0.33 mM) dissolved in 5 ml of dichloromethane. The reaction mixture was heated at 65□, stirred for 2 hours and the solvent was removed. The remaining residue was purified with Silica gel column chromatography with a mobile phase (dichloromethane:methanol=8:1) to obtain white solid type of N-phenyl 2-[2-(4'-hydroxy-3'-methoxyphenyl)-3-(methylthio)-benzofuran-5-yl]acetamide (22i; 138 mg).

Yield: 40%;
m.p: 166.3° C.;
$^1$H NMR (CDCl$_3$): δ ppm 7.88-7.92 (m, 2H, H-2' and H-6'), 7.64 (d, 1H, J=1.5 Hz, H-4), 7.52 (d, 1H, J=8.4 Hz, H-5'), 7.41 (d, 2H, Ph), 7.26-7.30 (m, 2H, Ph and H-6), 7.09 (d, 2H, Ph), 7.04 (d, 1H, J=8.4 Hz, H-7), 5.85 (s, 1H, OH), 4.02 (s, 3H, OCH$_3$), 3.88 (s, 2H, CH$_2$Ar), 2.38 (s, 3H, SCH$_3$);
IR (KBr): δ ppm 3435, 1658, 1505, 1464, 1278 cm$^{-1}$;
MS (EI) m/z 419 [M$^+$].

Example 44

N-benzyl 2-[2-(4'-hydroxy-3'-methoxyphenyl)-3-(methylthio)-benzofuran-5-yl]acetamide (22j)

0.06 ml of benzylamine (0.53 mM) was added to the solution containing 176.8 mg of pentafluorophenyl 2-[2-(4'-hydroxy-3'-methoxyphenyl)-3-(methylthio)-benzofuran-5-yl]-acetate (20a; 0.35 mM) dissolved in 5 ml of dichloromethane. The reaction mixture was stirred for 1 hour and the solvent was removed. The remaining residue was purified with Silica gel column chromatography with a mobile phase (dichloromethane:methanol=8:1) to obtain white solid type of N-benzyl 2-[2-(4'-hydroxy-3'-methoxyphenyl)-3-(methylthio)-benzofuran-5-yl]acetamide (22j; 151 mg).

Yield: 61%;
m.p: 166.4° C.;
$^1$H NMR (CDCl$_3$): δ ppm 7.85-7.9 (m, 2H, H-2' and H-6'), 7.57 (d, 1H, J=1.5 Hz, H-4), 7.47 (d, 1H, J=8.3 Hz, H-5'), 7.17-7.4 (m, 6H, Ph and H-6), 7.03 (d, 1H, J=8 Hz, H-7), 5.74 (bt, 1H, NH), 4.44 (d, 2H, J=5.9 Hz, PhCH$_2$NH), 4.01 (s, 3H, OCH$_3$), 3.77 (s, 2H, CH$_2$Ar), 2.34 (s, 3H, SCH$_3$);
IR (KBr): δ ppm 3855, 3741, 1644, 1505, 1463, 1277, 1029 cm$^{-1}$;
MS (FAB) m/z 434 [MH$^+$].

Example 45

N,N-diethyl 3-[2-(4'-hydroxy-3'-methoxyphenyl)-3-(methylthio)-benzofuran-5-yl]propionamide (22k)

Through similar procedure to the method disclosed in Example 35, white solid type of N,N-diethyl 3-[2-(4'-hydroxy-3'-methoxyphenyl)-3-(methylthio)-benzofuran-5-yl] propionamide (22k; 140 mg) showing following physicochemical property was obtained (yield: 63%).

m.p: 108.4° C.;
$^1$H NMR (CDCl$_3$): δ ppm 7.84-7.9 (m, 2H, H-2' and H-6'), 7.51 (d, 1H, J=1.5 Hz, H-4), 7.40 (d, 1H, J=8.2 Hz, H-5'), 7.17 (dd, 1H, J=1.7, 8.3 Hz, H-6), 7.02 (d, 1H, J=8.3 Hz, H-7), 5.93 (s, 1H, OH), 4.01 (s, 3H, OCH$_3$), 3.39 (q, 2H, J=7.1 Hz, CH$_3$CH$_2$N), 3.24 (q, 2H, J=7.1 Hz, CH$_3$CH$_2$N), 3.12 (t, 2H, J=7.9 Hz, >NCOCH$_2$), 2.67 (t, 2H, J=7.9 Hz, CH$_2$Ar), 2.37 (s, 3H, SCH$_3$), 1.12 (dt, 6H, (CH$_3$CH$_2$)$_2$N);
IR (KBr): δ ppm 2974, 1617, 1504, 1466, 1279, 1129, 1081, 1032 cm$^{-1}$;
MS (FAB) m/z 414 [MH$^+$].

Example 46

N,N-dimethyl 3-[2-(4'-hydroxy-3'-methoxyphenyl)-3-(methylthio)-benzofuran-5-yl]propionamide (22l)

Through similar procedure to the method disclosed in Example 36, white solid type of N,N-dimethyl 3-[2-(4'-hydroxy-3'-methoxyphenyl)-3-(methylthio)-benzofuran-5-yl] propionamide (22l; 122 mg) showing following physicochemical property was obtained (yield: 97%).

m.p: 149.3° C.;
$^1$H NMR (CDCl$_3$): δ ppm 7.85-7.9 (m, 2H, H-2' and H-6'), 7.51 (d, 1H, J=1.8 Hz, H-4), 7.41 (d, 1H, J=8.2 Hz, H-5'), 7.17 (dd, 1H, J=1.8, 8.2 Hz, H-6), 7.03 (d, 1H, J=8.2 Hz, H-7), 4.01 (s, 3H, OCH$_3$), 3.11 (t, 2H, J=7.9 Hz, >NCOCH$_2$), 2.97 (s, 3H, (CH$_3$)$_2$N), 2.95 (s, 3H, (CH$_3$)$_2$N), 2.69 (t, 2H, J=7.9 Hz, CH$_2$Ar), 2.37 (s, 3H, SCH$_3$);
IR (KBr): δ ppm 2924, 1627, 1506, 1466, 1279 cm$^{-1}$;
MS (FAB) m/z 386 [MH$^+$], 408 [MNa$^+$].

Example 47

N-methyl 3-[2-(4'-hydroxy-3'-methoxyphenyl)-3-(methylthio)-benzofuran-5-yl]propionamide (22m)

Through similar procedure to the method disclosed in Example 37, white solid type of N-methyl 3-[2-(4'-hydroxy-3'-methoxyphenyl)-3-(methylthio)-benzofuran-5-yl]propionamide (22m; 98 mg) showing following physicochemical property was obtained (yield: 62%).

m.p: 145.4° C.;
$^1$H NMR (CDCl$_3$): δ ppm 7.85-7.9 (m, 2H, H-2' and H-6'), 7.50 (d, 1H, J=1.8 Hz, H-4), 7.40 (d, 1H, J=8.4 Hz, H-5'), 7.14 (dd, 1H, J=1.8, 8.3 Hz, H-6), 7.02 (d, 1H, J=8.3 Hz, H-7), 5.83 (s, 1H, OH), 5.33 (bs, 1H, NH), 4.01 (s, 3H, OCH$_3$), 3.10 (t, 2H, J=7.8 Hz, HNCOCH$_2$), 2.78 (d, 3H, J=5 Hz, CH$_3$NH), 2.54 (t, 2H, J=7.8 Hz, CH$_2$Ar), 2.37 (s, 3H, SCH$_3$);
IR (KBr): δ ppm 3301, 2925, 1644, 1507, 1466, 1279, 1127, 1082, 1030 cm$^{-1}$;
MS (FAB) m/z 372 [MH$^+$], 394 [MNa$^+$].

Example 48

3-[2-(4'-hydroxy-3'-methoxyphenyl)-3-(methylthio)-benzofuran-5-yl]-1-morpholino-1-propanone (22n)

Through similar procedure to the method disclosed in Example 38, white solid type of 3-[2-(4'-hydroxy-3'-methoxyphenyl)-3-(methylthio)-benzofuran-5-yl]-1-morpholino-1-propanone (22n; 95 mg) showing following physicochemical property was obtained (yield: 51%).

m.p.: 130.6° C.;
$^1$H NMR (CDCl$_3$): δ ppm 7.85-7.9 (m, 2H, H-2' and H-6'), 7.50 (d, 1H, J=1.7 Hz, H-4), 7.41 (d, 1H, J=8.4 Hz, H-5'), 7.16 (dd, 1H, J=1.7, 8.1 Hz, H-6), 7.03 (d, 1H, J=8.1 Hz, H-7), 4.01 (s, 3H, OCH$_3$), 3.65 (s, 4H, CH$_2$OCH$_2$), 3.52 (t, 2H, J=4.7 Hz, CH$_2$NCH$_2$), 3.38 (t, 2H, J=4.7 Hz, CH$_2$NCH$_2$), 3.12 (t, 2H, J=7.8 Hz, >NCOCH$_2$), 2.70 (t, 2H, J=7.8 Hz, CH$_2$Ar), 2.37 (s, 3H, SCH$_3$);
IR (KBr): δ ppm 3434, 1615, 1502, 1465, 1290, 1233, 1113, 1032 cm$^{-1}$;
MS (EI) m/z 427 [M$^+$].

Example 49

3-[2-(4'-hydroxy-3'-methoxyphenyl)-3-(methylthio)-benzofuran-5-yl]-1-piperazino-1-propanone (22o)

Through similar procedure to the method disclosed in Example 39, white solid type of 3-[2-(4'-hydroxy-3'-methoxyphenyl)-3-(methylthio)-benzofuran-5-yl]-1-piperazino-1-propanone (22o; 124 mg) showing following physicochemical property was obtained (yield: 71%).

m.p: 152.6° C.;
$^1$H NMR (CDCl$_3$): δ ppm 7.84-7.9 (m, 2H, H-2' and H-6'), 7.51 (d, 1H, J=1.6 Hz, H-4), 7.40 (d, 1H, J=8.4 Hz, H-5'), 7.16 (dd, 1H, J=1.6, 8.4 Hz, H-6), 7.01 (d, 1H, J=8.4 Hz, H-7), 4.00 (s, 3H, OCH$_3$), 3.63 (t, 2H, J=5 Hz, CH$_2$N(C=O)CH$_2$), 3.39 (t, 2H, J=5 Hz, CH$_2$N(C=O)CH$_2$), 2.84 (t, 2H, J=5.3 Hz, CH$_2$NHCH$_2$), 2.74 (t, 2H, J=5.3 Hz, CH$_2$NHCH$_2$), 3.11 (t, 2H, J=7.9 Hz, >NCOCH$_2$), 2.70 (t, 2H, J=7.9 Hz, CH$_2$Ar), 2.37 (s, 3H, SCH$_3$);
IR (KBr): δ ppm 3438, 2920, 1637, 1503, 1465, 1280, 1125, 1027 cm$^{-1}$;
MS (EI) m/z 426 [M$^+$].

Example 50

3-[2-(4'-hydroxy-3'-methoxyphenyl)-3-(methylthio)-benzofuran-5-yl]-1-(4-benzylpiperazino)-1-propanone (22p)

Through similar procedure to the method disclosed in Example 40, colorless oil type of 3-[2-(4'-hydroxy-3'-methoxyphenyl)-3-(methylthio)-benzofuran-5-yl]-1-(4-benzylpiperazino)-1-propanone (22p; 136 mg) showing following physicochemical property was obtained (yield: 71%).

$^1$H NMR (CDCl$_3$): δ ppm 7.85-7.9 (m, 2H, H-2' and H-6'), 7.50 (d, 1H, J=1.8 Hz, H-4), 7.40 (d, 1H, J=8.4 Hz, H-5'), 7.24-7.3 (m, 5H, Ph), 7.16 (dd, 1H, J=1.8, 8.4 Hz, H-6), 7.03 (d, 1H, J=8.4 Hz, H-7), 4.01 (s, 3H, OCH$_3$), 3.65 (t, 2H, J=4.8 Hz, CH$_2$N(C=O)CH$_2$), 3.45 (s, 2H, PhCH$_2$N), 3.39 (t, 2H, J=4.8 Hz, CH$_2$N(C=O)CH$_2$), 3.10 (t, 2H, J=7.8 Hz, >NCOCH$_2$), 2.68 (t, 2H, J=7.8 Hz, CH$_2$Ar), 2.38 (t, 2H, J=5.1 Hz, CH$_2$NCH$_2$), 2.36 (s, 3H, SCH$_3$), 2.25 (t, 2H, J=5.1 Hz, CH$_2$NCH$_2$);
IR (KBr): δ ppm 2921, 1627, 1504, 1466, 1280, 1030 cm$^{-1}$;
MS (EI) m/z 516 [M$^+$].

Example 51

3-[2-(4'-hydroxy-3'-methoxyphenyl)-3-(methylthio)-benzofuran-5-yl]-1-(4-benzylpiperidino)-1-propanone (22q)

Through similar procedure to the method disclosed in Example 41, white solid type of 3-[2-(4'-hydroxy-3'-methoxyphenyl)-3-(methylthio)-benzofuran-5-yl]-1-(4-benzylpiperidino)-1-propanone (22q; 84 mg) showing following physicochemical property was obtained (yield: 47%).

m.p: 156.6° C.;

$^1$H NMR (CDCl$_3$): δ ppm 7.85-7.9 (m, 2H, H-2' and H-6'), 7.50 (bs, 1H, H-4), 7.41 (d, 1H, J=8.4 Hz, H-5'), 7.0-7.3 (m, 7H, Ph, H-6 and H-7), 5.86 (bs, 1H, OH), 4.65 (bd, 1H, J=12.8 Hz, CH$_2$NCH$_2$), 4.00 (s, 3H, OCH$_3$), 3.76 (bd, 1H, J=12.8 Hz, CH$_2$NCH$_2$), 3.10 (t, 2H, J=7.8 Hz, >NCOCH$_2$), 2.84 (bt, 1H, CH$_2$NCH$_2$), 2.67 (t, 2H, J=7.8 Hz, CH$_2$Ar), 2.38-2.54 (m, 3H, CH$_2$NCH$_2$ and PhCH$_2$), 2.36 (s, 3H, SCH$_3$), 1.5-1.75 (m, 4H, CH$_2$CH$_2$NCH$_2$CH$_2$), 0.75-1.2 (m, 1H, BnCH);

IR (KBr): δ ppm 2922, 1616, 1504, 1466, 1280 cm$^{-1}$;

MS (FAB) m/z 516 [MH$^+$].

Example 52

(R)-2-(2-(2-(4'-hydroxy-3'-methoxyphenyl)-3-(methylthio)-benzofuran-5-yl)acetamide-4-methylpentylamide (22r)

Through similar procedure to the method disclosed in Example 42, white solid type of (R)-2-(2-(2-(4'-hydroxy-3'-methoxyphenyl)-3-(methylthio)-benzofuran-5-yl)acetamide-4-methylpentylamide (22r; 67 mg) showing following physicochemical property was obtained (yield: 95%).

m.p: 179.0° C.;

$^1$H NMR (CDCl$_3$): δ ppm 7.84-7.9 (m, 2H, H-2' and H-6'), 7.49 (d, 1H, J=1.5 Hz, H-4), 7.39 (d, 1H, J=8.4 Hz, H-5'), 7.13 (dd, 1H, J=1.5, 8.4 Hz, H-6), 7.02 (d, 1H, J=8.4 Hz, H-7), 6.12 (bs, 1H, NH), 5.87 (bs, 1H, OH), 5.86 (bs, 1H, NH), 5.34 (bs, 1H, NH), 4.45 (m, 1H, CHNH), 34.01 (s, 3H, OCH$_3$), 3.10 (t, 2H, J=7.5 Hz, HNCOCH$_2$), 2.60 (t, 2H, J=7.5 Hz, CH$_2$Ar), 2.36 (s, 3H, SCH$_3$), 1.35-1.65 (m, 3H, CHMe$_2$ and CH$_2$CONH$_2$), 0.86 (dd, 6H, J=2.2, 6.2 Hz, CH(CH$_3$)$_2$);

IR (KBr): δ ppm 3300, 2957, 1653, 1507, 1465, 1257, 1031 cm$^{-1}$;

MS (FAB) m/z 471 [MH$^+$], 493 [MNa$^+$].

Example 53

N-phenyl-3-[2-(4'-hydroxy-3'-methoxyphenyl)-3-(methylthio)-benzofuran-5-yl)propionamide (22s)

Through similar procedure to the method disclosed in Example 43, white solid type of N-phenyl-3-[2-(4'-hydroxy-3'-methoxyphenyl)-3-(methylthio)-benzofuran-5-yl)propionamide (22s; 85 mg) showing following physicochemical property was obtained (yield: 48%).

m.p: 180.4° C.;

$^1$H NMR (CDCl$_3$): δ ppm 7.84-7.9 (m, 2H, H-2' and H-6'), 7.54 (bs, 1H, H-4), 7.4-7.46 (m, 3H, H-5' and Ph), 7.25-7.32 (m, 2H, Ph), 7.19 (dd, 1H, J=1.5, 8.4 Hz, H-6), 7.09 (m, 1H, Ph), 7.02 (d, 1H, J=8.4 Hz, H-7), 6.99 (bs, 1H, NH), 5.82 (s, 1H, OH), 4.01 (s, 3H, OCH$_3$), 3.20 (t, 2H, J=7.5 Hz, HNCOCH$_2$), 2.73 (t, 2H, J=7.5 Hz, CH$_2$Ar), 2.32 (s, 3H, SCH$_3$);

IR (KBr): δ ppm 3303, 1660, 1599, 1504, 1442, 1254, 1030 cm$^{-1}$;

MS (FAB) m/z 434 [MH$^+$].

Example 54

N-benzyl-3-[2-(4'-hydroxy-3'-methoxyphenyl)-3-(methylthio)-benzofuran-5-yl)propionamide (22t)

Through similar procedure to the method disclosed in Example 44, white solid type of N-benzyl-3-[2-(4'-hydroxy-3'-methoxyphenyl)-3-(methylthio)-benzofuran-5-yl)propionamide (22t; 113 mg) showing following physicochemical property was obtained (yield: 60%).

m.p: 147.6° C.;

$^1$H NMR (CDCl$_3$): δ ppm 7.85-7.9 (m, 2H, H-2' and H-6'), 7.51 (d, 1H, J=1.5 Hz, H-4), 7.39 (d, 1H, J=8.3 Hz, H-5'), 7.1-7.3 (m, 6H, Ph and H-6), 7.03 (d, 1H, J=8.3 Hz, H-7), 5.84 (s, 1H, OH), 5.60 (bt, 1H, NH), 4.41 (d, 2H, J=5.7 Hz, PhCH$_2$NH), 4.01 (s, 3H, OCH$_3$), 3.14 (t, 2H, J=7.5 Hz, HNCOCH$_2$), 2.60 (t, 2H, J=7.5 Hz, CH$_2$Ar), 2.33 (s, 3H, SCH$_3$);

IR (KBr): δ ppm 3435, 1636, 1543, 1505, 1456, 1255 cm$^{-1}$;

MS (FAB) m/z 448 [MH$^+$]

Example 55

2-[2-(4'-hydroxy-3'-methoxyphenyl)-3-(methylthio)-benzofuran-5-yl]acetamide (23a)

2M ammonia dissolved in 0.5 ml of methanol was added to the solution containing 192.6 mg of pentafluorophenyl 2-[2-(4'-hydroxy-3'-methoxyphenyl)-3-(methylthio)-benzofuran-5-yl]-acetate (20a; 0.38 mM) dissolved in 2 ml of methanol cooled at −780. The reaction mixture was left alone at room temperature, stirred for 5 minutes and the solvent was removed. The remaining residue was purified with Silica gel column chromatography with a mobile phase (dichloromethane:methanol=8:1) to obtain white solid type of 2-[2-(4'-hydroxy-3'-methoxyphenyl)-3-(methylthio)-benzofuran-5-yl]acetamide (23a; 130 mg).

Yield: 98%;

m.p: 208° C.;

$^1$H NMR (CDCl$_3$): δ ppm 7.85-7.91 (m, 2H, H-2' and H-6'), 7.58 (d, 1H, J=1.7 Hz, H-4), 7.49 (d, 1H, J=8.4 Hz, H-5'), 7.22 (dd, 1H, J=1.7, 8.4 Hz, H-6), 7.04 (d, 1H, J=8.4 Hz, H-7), 5.85 (s, 1H, OH), 5.37 (bs, 2H, CONH$_2$), 4.01 (s, 3H, OCH$_3$), 3.74 (s, 2H, CH$_2$Ar), 2.37 (s, 3H, SCH$_3$);

IR (KBr): δ ppm 3753, 3432, 1650, 1507, 1470, 1276, 1209 cm$^{-1}$;

MS (FAB) m/z 343 [MH$^+$].

Example 56

3-[2-(4'-hydroxy-3'-methoxyphenyl)-3-(methylthio)-benzofuran-5-yl)propionamide (23b)

Through similar procedure to the method disclosed in Example 55, white solid type of 3-[2-(4'-hydroxy-3'-methoxyphenyl)-3-(methylthio)-benzofuran-5-yl)propionamide (23b; 141 mg) showing following physicochemical property was obtained (yield: 95%).

m.p: 172.9° C.;

$^1$H NMR (CDCl$_3$): δ ppm 7.85-7.9 (m, 2H, H-2' and H-6'), 7.51 (d, 1H, J=1.8 Hz; H-4), 7.41 (d, 1H, J=8.4 Hz, H-5'), 7.18 (dd, 1H, J=1.8, 8.1 Hz, H-6), 7.02 (d, 1H, J=8.1 Hz, H-7), 5.83 (s, 1H, OH), 5.38 (bs, 2H, CONH$_2$), 4.01 (s, 3H, OCH$_3$), 3.11 (t, 2H, J=7.6 Hz, H$_2$NCOCH$_2$), 2.62 (t, 2H, J=7.6 Hz, CH$_2$Ar), 2.37 (s, 3H, SCH$_3$);

IR (KBr): δ ppm 3346, 1659, 1604, 1506, 1466, 1278, 1127, 1030 cm$^{-1}$;

MS (FAB) m/z 358 [MH$^+$].

Example 57

2-[2-(4'-hydroxy-3'-methoxyphenyl)-3-(methylthio)-benzofuran-5-yl)ethylamine (24a)

Through similar procedure to the method disclosed in Example 13, white solid type of 2-[2-(4'-hydroxy-3'-methoxyphenyl)-3-(methylthio)-benzofuran-5-ylethylamine (24a; 85 mg) showing following physicochemical property was obtained (yield: 62%).

m.p: 180.9° C.;

$^1$H NMR (CD$_3$OD): δ ppm 7.96 (d, 1H, J=2 Hz, H-2'), 7.79 (dd, 1H, J=2, 8.4 Hz, H-6'), 7.59 (d, 1H, J=1.8 Hz, H-4), 7.50 (d, 1H, J=8.4 Hz, H-5'), 7.23 (dd, 1H, J=1.8, 8.4 Hz, H-6), 6.91 (d, 1H, J=8.1 Hz, H-7), 3.95 (s, 3H, OCH$_3$), 3.23 (t, 2H, J=7.8 Hz, H$_2$NCH$_2$), 3.08 (t, 2H, J=7.8 Hz, CH$_2$Ar), 2.37 (s, 3H, SCH$_3$);

IR (KBr): δ ppm 3435, 1605, 1500, 1468, 1291, 1233, 1126, 1084, 1030 cm$^{-1}$;

MS (FAB) m/z 330 [MH$^+$].

Example 58

3-[2-(4''-hydroxy-3'-methoxyphenyl)-3-(methylthio)-benzofuran-5-yl)propylamine (24b)

Through similar procedure to the method disclosed in Example 13, white solid type of 3-[2-(4'-hydroxy-3'-methoxyphenyl)-3-(methylthio)-benzofuran-5-yl)propylamine (24b; 96 mg) showing following physicochemical property was obtained (yield: 65%).

m.p: 163.1° C.;

$^1$H NMR (CD$_3$OD): δ ppm 7.95 (d, 1H, J=2 Hz, H-2'), 7.78 (dd, 1H, J=2, 8.4 Hz, H-6'), 7.52 (d, 1H, J=1.8 Hz, H-4), 7.44 (d, 1H, J=8.4 Hz, H-5'), 7.19 (dd, 1H, J=1.8, 8.2 Hz, H-6), 6.91 (d, 1H, J=8.2 Hz, H-7), 3.95 (s, 3H, OCH$_3$), 2.93 (t, 2H, J=7.6 Hz, H$_2$NCH$_2$), 2.85 (t, 2H, J=7.6 Hz, CH$_2$Ar), 2.36 (s, 3H, SCH$_3$), 2.01 (dt, 2H, H$_2$NCH$_2$CH$_2$);

IR (KBr): δ ppm 3395, 1555, 1464, 1279, 1128 cm$^{-1}$;

MS (FAB) m/z 343 [M$^+$].

Example 59

Benzyl N-2-[2-(4'-hydroxy-3'-methoxyphenyl)-3-(methylthio)-benzofuran-5-yl]ethylcarbomate (25a)

0.04 ml of benzylchloroform (0.28 mM) was added to the solution containing 91.3 mg of 2-[2-(4'-hydroxy-3'-methoxyphenyl)-3-(methylthio)-benzofuran-5-yl)ethylamine (24a; 0.28 mM) dissolved in 2 ml of THF. The reaction mixture was heated at 65☐ and stirred for 2 hours. The reacted product was extracted with ethylacetate, dried with magnesium sulfate and the solvent was removed. The remaining residue was purified with Silica gel column chromatography with a mobile phase (hexane:ethylacetate=4:1) to obtain colorless oil type of benzyl N-2-[2-(4'-hydroxy-3'-methoxyphenyl)-3-(methylthio)-benzofuran-5-yl]ethylcarbomate (25a; 130 mg).

Yield: 95%;

$^1$H NMR (CDCl$_3$): δ ppm 7.85-7.9 (m, 2H, H-2' and H-6'), 7.49 (bs, 1H, H-4), 7.41 (d, 1H, J=8.3 Hz, H-5'), 7.3-7.37 (m, 5H, Ph), 7.12 (bd, 1H, 8.4 Hz, H-6), 7.03 (d, 1H, J=8.4 Hz, H-7), 5.84 (s, 1H, OH), 5.10 (s, 2H, PhCH$_2$O), 4.79 (bs, 1H, NH), 4.01 (s, 3H, OCH$_3$), 3.53 (dd, 2H, CONHCH$_2$), 2.95 (t, 2H, J=7 Hz, CH$_2$Ar), 2.34 (s, 3H, SCH$_3$);

IR (KBr): δ ppm 2927, 1765, 1605, 1502, 1466, 1243, 1207, 1175, 1035 cm$^{-1}$;

MS (FAB) m/z 486 [MNa$^+$].

Example 60

Benzyl N-3-[2-(4'-hydroxy-3'-methoxyphenyl)-3-(methylthio)-benzofuran-5-yl)propylcarbomate (25b)

Through similar procedure to the method disclosed in Example 59, colorless oil type of benzyl N-3-[2-(4'-hydroxy-3'-methoxyphenyl)-3-(methylthio)-benzofuran-5-yl)propylcarbomate (25b; 143 mg) showing following physicochemical property was obtained (yield: 98%).

$^1$H NMR (CDCl$_3$): δ ppm d 8.01 (d, 1H, J=1.8 Hz, H-2'), 7.92 (dd, 1H, J=1.8, 8.4 Hz, H-6'), 7.53 (d, 1H, J=2 Hz, H-4), 7.35-7.48 (m, 6H, H-5' and Ph), 7.24 (d, 1H, J=8.4 Hz, H-7), 7.19 (dd, 1H; J=2, 8.4 Hz, H-6), 5.31 (s, 2H, PhCH$_2$O), 3.93 (s, 3H, OCH$_3$), 3.73 (t, 2H, CONHCH$_2$), 2.86 (t, 2H, J=7.6 Hz, CH$_2$Ar), 2.38 (s, 3H, SCH$_3$), 1.97 (dt, 2H, CONHCH$_2$CH$_2$);

IR (KBr): δ ppm 2928, 1765, 1605, 1502, 1465, 1243, 1207, 1175, 1035 cm$^{-1}$;

MS (FAB) m/z 501.0 [MNa$^+$].

Example 61

Methyl 3-[2-(4'-(3-chloropropoxy)-3'-methoxyphenyl)-3-(methylthio)-benzofuran-5-yl) propionate (26)

991.2 mg of 1-bromo-3-chloropropane (6.3 mM) was added to the solution containing 343 mg of 2-[2-(4'-hydroxy-3'-methoxyphenyl)-3-(methylthio)-benzofuran-5-yl]acetate (9a; 0.28 mM) and 522.43 mg of potassium carbonate (3.78 mM) dissolved in 7 ml of acetone. The reaction mixture was heated for 2-3 days at 60-65° C. and remaining potassium carbonate and solvent were removed. The remaining residue was purified with Silica gel column chromatography with a mobile phase (hexane:ethylacetate=4:1) to obtain white solid type of methyl 3-[2-(4'-(3-chloropropoxy)-3'-methoxyphenyl)-3-(methylthio)-benzofuran-5-yl) propionate (26; 565 mg).

Yield: 85%;

m.p: 85.5° C.;

$^1$H NMR (CDCl$_3$): δ ppm d 7.92 (d, 1H, J=2 Hz, H-2'), 7.88 (dd, 1H, J=2, 8.3 Hz, H-6'), 7.51 (d, 1H, J=1.5 Hz, H-4), 7.41 (d, 1H, J=8.3 Hz, H-5'), 7.15 (dd, 1H, J=1.5, 8.4 Hz, H-6); 7.01 (d, 1H, J=8.4 Hz, H-7), 4.25 (t, 2H, J=6.0 Hz, ArOCH$_2$), 3.97 (s, 3H, OCH$_3$), 3.80 (t, 2H, J=6.3 Hz, CH$_2$Cl), 3.69 (s, 3H, CO$_2$CH$_3$), 3.09 (t, 2H, J=7.8 Hz, MeO$_2$CCH$_2$), 2.71 (t, 2H, J=7.8 Hz, CH$_2$Ar), 2.37 (s, 3H, SCH$_3$), 2.33 (m, 2H, ArOCH$_2$CH$_2$).

Example 62

Methyl 3-[2-{4'-[3-(diethylamino)propoxy]-3'-methoxyphenyl)-3-(methylthio)-benzofuran-5-yl) propionate (27)

0.1 ml of diethylamine (1.05 mM) was added to the solution containing 315.9 mg of 3-[2-(4'-(3-chloropropoxy)-3'-methoxyphenyl)-3-(methylthio)-benzofuran-5-yl) propionate (26; 0.7 mM) dissolved in 7 ml of methanol. The reaction mixture was heated for 2-3 days at 70° C. and remaining solvent were removed. The remaining residue was purified with Silica gel column chromatography with a mobile phase (hexane:ethylacetate=4:1) to obtain white solid type of methyl 3-[2-{4'-[3-(diethylamino)propoxy]-3'-methoxyphenyl)-3-(methylthio)-benzofuran-5-yl) propionate (27; 341 mg).

Yield: 92%;

m.p: 66.1° C.;

$^1$H NMR (CDCl$_3$): δ ppm d 7.91 (d, 1H, J=2 Hz, H-2'), 7.87 (dd, 1H, J=2, 8.3 Hz, H-6'), 7.50 (d, 1H, J=1.8 Hz, H-4), 7.41 (d, 1H, J=8.3 Hz, H-5'), 7.14 (dd, 1H, J=1.8, 8.6 Hz, H-6), 7.00 (d, 1H, J=8.6 Hz, H-7), 4.15 (t, 2H, J=6.7 Hz, ArOCH$_2$), 3.97 (s, 3H, OCH$_3$), 3.69 (s, 3H, CO$_2$CH$_3$), 3.09 (t, 2H, J=7.8 Hz, MeO$_2$CCH$_2$), 2.71 (t, 2H, J=7.8 Hz, CH$_2$Ar), 2.64 (t, 2H, J=7.1 Hz, CH$_2$NEt$_2$), 2.55 (q, 4H, J=7.1 Hz, 2×NCH$_2$CH$_3$), 2.37 (s, 3H, SCH$_3$), 2.02 (m, 2H, ArOCH$_2$CH$_2$), 1.04 (t, 6H, J=7.1 Hz, 2×NCH$_2$CH$_3$);

IR (KBr): δ ppm 2965, 1738, 1506, 1466, 1251, 1144, 1032 cm$^{-1}$;

MS (FAB) m/z 486 [MH$^+$].

Example 63

Methyl 3-[2-{4'-[3-(diethylamino)propoxy]-3'-methoxyphenyl)-benzofuran-5-yl)propionate (28)

Through similar procedure to the method disclosed in Example 3, white solid type of N-methyl 3-[2-(4'13-(diethylamino)propoxy]-3'-methoxyphenyl)-benzofuran-5-yl)propionate (28; 350 mg) showing following physicochemical property was obtained (yield: 84%).

m.p: 168.8° C.;

$^1$H NMR (CDCl$_3$): δ ppm d 7.36-7.44 (m, 4H, Ar), 7.10 (dd, 1H, J=1.8, 8.3 Hz, H-6), 6.94 (d, 1H, J=8.3 Hz, H-7), 6.87 (s, 1H, H-3), 4.18 (t, 2H, J=5.5 Hz, ArOCH$_2$), 3.95 (s, 3H, OCH$_3$), 3.68 (s, 3H, CO$_2$CH$_3$), 3.27 (t, 2H, J=7.8 Hz, CH$_2$NEt$_2$), 3.15 (q, 4H, J=7.3 Hz, 2×NCH$_2$CH$_3$), 3.04 (t, 2H, J=7.7 Hz, MeO$_2$CCH$_2$), 2.68 (t, 2H, J=7.7 Hz, CH$_2$Ar), 2.42 (m, 2H, ArOCH$_2$CH$_2$), 1.44 (t, 6H, J=7.3 Hz, 2×NCH$_2$CH$_3$);

IR (KBr): δ ppm 3741, 3395, 2952, 1734, 1513, 1460, 1227, 1142, 1026 cm$^{-1}$;

MS (FAB) m/z 440 [MH$^+$].

Example 64

3-[2-{4'-[3-(diethylamino)propoxy]-3'-methoxyphenyl}-3-(methylthio)-benzofuran-5-yl)propanol (29)

Through similar procedure to the method disclosed in Example 13, white solid type of 3-[2-{4'-[3-(diethylamino)propoxy]-3'-methoxyphenyl}-3-(methylthio)-benzofuran-5-yl)propanol (29; 270 mg) showing following physicochemical property was obtained (yield: 62%).

m.p: 114.2° C.;

$^1$H NMR (CDCl$_3$): δ ppm d 7.91 (d, 1H, J=1.8 Hz, H-2'), 7.88 (dd, 1H, J=1.8, 8.4 Hz, H-6'), 7.50 (d, 1H, J=1.5 Hz, H-4), 7.41 (d, 1H, J=8.4 Hz, H-5'), 7.16 (dd, 1H, J=1.5, 8.4 Hz, H-6), 6.97 (d, 1H, J=8.4 Hz, H-7), 4.20 (t, 2H, J=5 Hz, ArOCH$_2$), 3.95 (s, 3H, OCH$_3$), 3.72 (t, 2H, J=6.3 Hz, HOCH$_2$), 3.29 (t, 2H, J=7.8 Hz, CH$_2$NEt$_2$), 3.17 (q, 4H, J=7.2 Hz, 2×NCH$_2$CH$_3$), 2.85 (t, 2H, J=7.7 Hz, CH$_2$Ar), 2.42 (m, 2H, ArOCH$_2$CH$_2$), 2.38 (s, 3H, SCH$_3$), 1.97 (m, 2H, HOCH$_2$CH$_2$), 1.45 (t, 6H, J=7.2 Hz, 2×NCH$_2$CH$_3$);

IR (KBr): δ ppm 3393, 2941, 1648, 1506, 1467, 1249, 1143, 1034 cm$^{-1}$;

MS (FAB) m/z 458 [MH$^+$].

Example 65

3-[2-{4'-[3-(diethylamino)propoxy]-3'-methoxyphenyl}-3-benzofuran-5-yl)propanol (30)

Through similar procedure to the method disclosed in Example 13, white solid type of 3-[2-{4'-[3-(diethylamino)propoxy]-3'-methoxyphenyl}-3-benzofuran-5-yl)propanol (30; 220 mg) showing following physicochemical property was obtained (yield: 58%).

m.p: 149.8° C.;

$^1$H NMR (CDCl$_3$): δ ppm d 7.36-7.44 (m, 4H, Ar), 7.10 (dd, 1H, J=1.8, 8.3 Hz, H-6), 6.94 (d, 1H, J=8.3 Hz, H-7), 6.87 (s, 1H, H-3), 4.18 (t, 2H, J=5 Hz, ArOCH$_2$), 3.95 (s, 3H, OCH$_3$), 3.71 (t, 2H, J=6.4 Hz, HOCH$_2$), 3.28 (t, 2H, J=7.7 Hz, CH$_2$NEt$_2$), 3.17 (q, 4H, J=7.3 Hz, 2×NCH$_2$CH$_3$), 2.81 (t, 2H, J=7.7 Hz, CH$_2$Ar), 2.43 (m, 2H, ArOCH$_2$CH$_2$), 1.95 (m, 2H, HOCH$_2$CH$_2$), 1.45 (t, 6H, J=7.3 Hz, 2×NCH$_2$CH$_3$);

IR (KBr): δ ppm 3366, 2947, 2618, 1511, 1471, 1253, 1140, 1059 cm$^{-1}$; MS (FAB) m/z 412 [MH$^+$].

Example 66

[2-(3,4-dimethoxy-phenyl)-3-(methylsulfanyl)-benzofuran-5-yl)acetic acid methyl ester (31a)

174 mg of potassium carbonate (1.26 mM) and 298 mg of iodomethane (2.1 mM) were added to the solution containing 145 ml of 2-[2-(4'-hydroxy-3'-methoxyphenyl)-3-(methylthio)-1-benzofuran-5-yl]acetate (7a; 0.42 mM) dissolved in 1 ml of acetone. The reaction mixture was refluxed for 3 hours and remaining inorganic substances were removed with filtration. The remaining solvent was removed. The remaining residue was purified with Silica gel column chromatography with a mobile phase (hexane:ethylacetate=4:1) to obtain white solid type of [2-(3,4-dimethoxy-phenyl)-3-(methylsulfanyl)-benzofuran-5-yl)acetic acid methyl ester (31a; 100 mg).

Yield: 64%;

m.p: 91° C.;

$^1$H NMR (CDCl$_3$): δ ppm d 7.92 (s, 1H), 7.88 (d, 1H, J=2.0 z), 7.58 (d, 1H, J=1.7 z,), 7.44 (d, 1H, J=8.3 Hz), 7.22 (dd, 1, J=8.4 & 1.7 Hz), 6.96 (d, 1H, J=8.3), 3.99 (s, 3), 3.93 (s, 3H), 3.75 (s, 2H), 3.71 (s, 3H), 3.37 (s, 3H);

IR (KBr): δ ppm 2922, 1737, 1605, 1507, 1467, 1253, 1144, 1024, 808 cm$^{-1}$;

MS (FAB+) m/z 372 [M$^+$].

Example 67

3-[2-(3,4-dimethoxyphenyl)-3-methylsulfanyl-benzofuran-5-yl]propionic acid methyl ester (31b)

Through similar procedure to the method disclosed in Example 66, white solid type of 3-[2-(3,4-dimethoxyphenyl)-3-methylsulfanyl-benzofuran-5-yl]propionic acid methyl ester (31b; 130 mg) showing following physicochemical property was obtained (yield: 98.9%).

m.p: 85~87° C.;

$^1$H NMR (CDCl$_3$): δ ppm d 7.92-7.88 (m, 2H), 7.51 (d, 1H, J=1.3 Hz), 7.42 (d, 1H, J=8.4 Hz), 7.15 (dd, 1H, J=8.3, 1.8 Hz), 6.99 (d, 1H, J=7.0 Hz), 4.00 (s, 3H), 3.96 (s, 3H), 3.69 (s, 3H), 3.09 (t, 2H, J=7.5 Hz), 2.71 (t, 2H, J=8.0 Hz), 2.38 (s, 3H);

IR (KBr): δ ppm 2924, 1737, 1507, 1467, 1254, 1146, 1027 cm$^{-1}$;

MS (FAB+) m/z 386 [M$^{-1}$].

Example 68

[2-(3,4-dimethoxyphenyl)-benzofuran-5-yl]acetic acid methyl ester (32a)

Through similar procedure to the method disclosed in Example 66, white solid type of [2-(3,4-dimethoxyphenyl)-benzofuran-5-yl]acetic acid methyl ester (32a; 136 mg) showing following physicochemical property was obtained (yield: 95.8%).

m.p: 119° C.;

¹H NMR (CDCl₃): δ ppm d 7.45-7.34 (m, 4H), 7.15 (d, 1H, J=8.43 Hz), 6.90 (dd, 1H, J=8.43 Hz & J=1.83 Hz), 6.84 (d, 1H, J=1.29), 3.96 (s, 3H), 3.90 (s, 3H), 3.7-3.66 (m, 5H);

IR (KBr): δ ppm 2927, 1736, 1609, 1511, 1466, 1255, 1144, 1024, 939, 860, 802 cm⁻¹;

MS (FAB+) m/z 326 [M⁺].

Example 69

3-[2-(3,4-dimethoxy-phenyl)-benzofuran-5-yl]-propionic acid methyl ester (32b)

Through similar procedure to the method disclosed in Example 66, white solid type of 3-[2-(3,4-dimethoxy-phenyl)-benzofuran-5-yl]-propionic acid methyl ester (32b; 155 mg) showing following physicochemical property was obtained (yield: 98.8%).

m.p: 105~107° C.;
¹H NMR (CDCl₃): δ ppm d 7.45-7.36 (m, 4H), 7.09 (dd, 1H), 6.94 (d, 1H, J=8.4 Hz), 6.86 (d, 1H), 4.00 (s, 3H), 3.94 (s, 3H), 3.68 (s, 3H), 3.05 (t, 2H), 2.68 (t, 2H);

IR (KBr): δ ppm 2927, 1737, 1511, 1468, 1254, 1170, 1144, 1026 cm⁻¹;

MS (FAB+) m/z 340 [M⁺].

Example 70

[2-(3,4-dimethoxy-phenyl)-3-methylsulfanyl-benzofuran-5-yl]-acetic acid (33a)

Through similar procedure to the method disclosed in Example 5, white solid type of 3-[2-(3,4-dimethoxy-phenyl)-3-methylsulfanyl-benzofuran-5-yl]-acetic acid (33a; 260 mg) showing following physicochemical property was obtained (yield: 94.3%).

m.p: 165° C.;
¹H NMR (CDCl₃): δ ppm d 7.91 (s, 1H), 7.88 (d, 1H, J=2.0 Hz), 7.58 (d, 1H, J=1.29 Hz), 7.45 (d, 1H, J=8.4 Hz), 7.23 (dd, 1H, J=8.43 Hz & J=1.65 Hz), 6.97 (d, 1H, J=8.25), 4.0 (s, 3H), 3.95 (s, 3H), 3.78 (s, 2H), 2.36 (s, 3H);

IR (KBr): δ ppm 2920, 1706, 1506, 1466, 1253, 1145, 1090, 1026, 965, 802, 760 cm⁻¹;

MS (FAB+) m/z 358 [M⁺].

Example 71

3-[2-(3,4-dimethoxy-phenyl)-3-methylsulfanyl-benzofuran-5-yl]-propionic acid (33b)

Through similar procedure to the method disclosed in Example 5, white solid type of 3-3-[2-(3,4-dimethoxy-phenyl)-3-methylsulfanyl-benzofuran-5-yl]-propionic acid (33b; 320 mg) showing following physicochemical property was obtained (yield: 97.6%).

m.p: 164~166° C.;
¹H NMR (CD₃OD): δ ppm d 7.97 (d, 1H, J=2.0 Hz), 7.87 (dd, 1H, J=8.6, 2.2 Hz), 7.53 (d, 1H, J=1.1 Hz), 7.41 (d, 1H, J=8.4 Hz), 7.20 (dd, 1H, J=8.4, 1.8 Hz), 7.07 (d, 1H, J=8.6 Hz), 3.92 (s, 3H), 3.89 (s, 3H), 3.04 (t, 2H, J=7.5 Hz), 2.66 (t, 2H, J=7.5 Hz), 2.36 (s, 3H);

IR (KBr): δ ppm 2921, 1706, 1502, 1445, 1246, 1145, 1090, 1026 cm⁻¹;

MS (FAB+) m/z 372 [M⁺].

Example 72

[2-(3,4-dimethoxy-phenyl)-benzofuran-5-yl]-acetic acid (34a)

Through similar procedure to the method disclosed in Example 5, white solid type of [2-(3,4-dimethoxy-phenyl)-benzofuran-5-yl]-acetic acid (34a; 554 mg) showing following physicochemical property was obtained (yield: 96.1%).

m.p: 202° C.;
¹H NMR (CD₃OD): δ ppm d 7.46 (m, 4H), 7.20 (m, 1H), 7.03 (m, 2H), 3.93 (s, 3H), 3.88 (s, 3H), 3.65 (s, 3H);

IR (KBr): δ ppm 2482, 1727, 1602, 1503, 1462, 1250, 1134, 1014, 931, 853 cm⁻¹;

MS (FAB+) m/z 312 [M⁺].

Example 73

3-[2-(3,4-dimethoxy-phenyl)-benzofuran-5-yl]-propionic acid (34b)

Through similar procedure to the method disclosed in Example 5, white solid type of 3-[2-(3,4-dimethoxy-phenyl)-benzofuran-5-yl]-propionic acid (34b; 554 mg) showing following physicochemical property was obtained (yield: 95.8%).

m.p: 105~107° C.;
¹H NMR (CD3OD): δ ppm d 7.47-7.37 (m, 4H), 7.12 (dd, 1H, J=8.4, 1.8 Hz), 7.02 (d, 1H, J=8.3 Hz), 6.99 (d, 1H, J=0.8 Hz), 3.91 (s, 3H), 3.87 (s, 3H), 2.99 (t, 2H, J=7.7 Hz), 2.63 (t, 2H, J=7.7 Hz);

MS (FAB+) m/z 340[M⁺].

Example 74

[2-(3,4-dimethoxy-phenyl)-3-methylsulfanyl-benzofuran-5-yl]-acetic acid (35a)

Through similar procedure to the method disclosed in Example 5, white solid type of 3[2-(3,4-dimethoxy-phenyl)-3-methylsulfanyl-benzofuran-5-yl]-acetic acid (35a; 720 mg) showing following physicochemical property was obtained (yield: 80%).

m.p: 90~92° C.;
¹H NMR (CDCl₃): δ ppm 7.54 (s, 1H), 7.51 (d, 1H, J=8.4 Hz), 7.46 (dd, 1H, J=8.43 Hz &, J=2.01), 7.37 (d, 1H, J=2.04 Hz), 7.23 (dd, 1H, J=8.43 Hz & J=2.01 Hz), 6.95 (d, 1H, J=8.4), 6.90 (s, 1H) 4.06 (s, 2H), 4.0 (s, 3H), 3.95 (s, 3H);

IR (KBr): δ ppm 2928, 2856, 1790, 1718, 1518, 1466, 1254, 1141, 1088, 999, 801 cm⁻¹.

Example 75

3-[2-(3,4-dimethoxy-phenyl)-3-methylsulfanyl-benzofuran-5-yl]-propionic acid pentafluorophenyl ester (35b)

Through similar procedure to the method disclosed in Example 5, white solid type of 3-[2-(3,4-dimethoxy-phenyl)-3-methylsulfanyl-benzofuran-5-yl]-propionic acid pentafluorophenyl ester (35b; 710 mg) showing following physicochemical property was obtained (yield: 79%).

m.p: 111~113° C.;
¹H NMR (CDCl₃): δ ppm d 7.98-7.90 (m, 2H), 7.57 (d, 1H, J=1.6 Hz), 7.45 (d, 1H, J=8.3 Hz), 7.20 (dd, 1H, J=8.4, 1.8

Hz), 6.99 (d, 1H, J=8.3 Hz), 4.01 (s, 3H), 3.96 (s, 3H), 3.23 (t, 2H, J=7.5 Hz), 3.07 (t, 2H, J=7.7 Hz), 2.38 (s, 3H);
IR (KBr): δ ppm 2926, 1789, 1520, 1469, 1254, 1145, 1096, 999 cm$^{-1}$.

Example 76

[2-(3,4-dimethoxy-phenyl)-benzofuran-5-yl]-acetic acid pentafluorophenyl ester (36a)

Through similar procedure to the method disclosed in Example 5, white solid type of 3-[2-(3,4-dimethoxy-phenyl)-benzofuran-5-yl]-acetic acid pentafluorophenyl ester (36a; 540 mg) showing following physicochemical property was obtained (yield: 69.4%).

m.p: 127° C.;
$^1$H NMR (CDCl$_3$): 5 ppm d 7.54 (s, 1H), 7.51 (d, 1H, J=8.4 Hz), 7.46 (dd, 1H, J=8.43 Hz &, J=2.01), 7.37 (d, 1H, J=2.04 Hz), 7.23 (dd, 1H, J=8.43 Hz & J=2.01 Hz), 6.95 (d, 1H, J=8.4), 6.90 (s, 1H) 4.06 (s, 2H), 4.0 (s, 3H), 3.95 (s, 3H);
IR (KBr): 5 ppm 2928, 2856, 1790, 1718, 1518, 1466, 1254, 1141, 1088, 999, 801 cm$^{-1}$;
MS (FAB+) m/z 388 [M$^+$].

Example 77

3-[2-(3,4-dimethoxy-phenyl)-benzofuran-5-yl]-propionic acid pentafluorophenyl ester (36b)

Through similar procedure to the method disclosed in Example 5, white solid type of 3-3-[2-(3,4-dimethoxy-phenyl)-benzofuran-5-yl]-propionic acid pentafluorophenyl ester (36b; 563 mg) showing following physicochemical property was obtained (yield: 99%).

m.p: 98~100° C.;
$^1$H NMR (CDCl$_3$): δ ppm d 7.47-7.37 (m, 4H), 7.14 (dd, 1H, J=8.4, 1.8 Hz), 6.95 (d, 1H, J=8.4 Hz), 6.87 (d, 1H), 4.00 (s, 3H), 3.94 (s, 3H), 3.18 (t, 2H, J=7.7 Hz), 3.04 (t, 2H, J=7.1 Hz);
IR (KBr): 5 ppm 2926, 1787, 1520, 1469, 1254, 1143, 1098, 998 cm$^{-1}$;
MS (FAB+) m/z 326 [M$^+$].

Example 78

2-[2-(3,4-dimethoxy-phenyl)-3-methylsulfanyl-benzofuran-5-yl)-1-(4-phenyl-piperazin-1-yl)-ethanone (37a)

Triethylamine and 12.992 mg of 1-phenyl-piperazine (0.080 mM) were added to the solution containing 35 mg of 3-[2-(3,4-dimethoxy-phenyl)-3-methylsulfanyl-benzofuran-5-yl]-acetic acid (35a; 0.068 mM) dissolved in 2 ml of dichloromethane. The reaction mixture was stirred for 16 hours and the remaining solvent was removed. The remaining residue was purified with Silica gel column chromatography with a mobile phase (dichloromethane:methanol=20:1) to obtain white solid type of 2-[2-(3,4-dimethoxy-phenyl)-3-methylsulfanyl-benzofuran-5-yl)-1-(4-phenyl-piperazin-1-yl)-ethanone (37a; 223 mg).

Yield: 95.7%;
m.p: 160° C.;
$^1$H NMR (CDCl$_3$): 5 ppm d 7.91 (S, 1H), d 7.88 (d, 1H, J=2.01) d 7.55 (d, 1H, J=1.29), 7.44 (d, 1H, J=8.43 Hz), 7.28-7.17 (m, 3H), 6.96 (d, 1H, J=8.79), 6.89 (m, 3H), 3.99 (s, 3H), 3.95 (s, 3H), 3.93 (s, 2H), 3.85 (t, 2H, J=6), 3.67 (t, 2H, J=4.77), 3.16 (t, 2H, J=5.13), 2.98 (t, 2H, J=5.13), 2.34 (s, 3H);
IR (KBr): δ ppm 2921, 1643, 1600, 1509, 1464, 1253, 1230, 1145, 1024, 758, 694 cm$^{-1}$;
MS (FAB+) m/z 503 [MH$^+$].

Example 79

3-[2-(3,4-dimethoxy-phenyl)-3-methylsulfanyl-benzofuran-5-yl]-1-(4-phenyl-piperazin-1yl)-propan-1-one (37b)

Through similar procedure to the method disclosed in Example 5, white solid type of 3-[2-(3,4-dimethoxy-phenyl)-3-methylsulfanyl-benzofuran-5-yl]-1-(4-phenyl-piperazin-1-yl)-propan-1-one (37b; 250 mg) showing following physicochemical property was obtained (yield: 99%).

m.p: 118~120° C.;
$^1$H NMR (CDCl$_3$): δ ppm d 7.91-7.89 (m, 2H), 7.53 (s, 1H), 7.42 (d, 1H, J=8.3 Hz), 7.26-7.17 (m, 3H), 6.98 (d, 1H, J=9.2 Hz), 6.90-6.86 (m, 3H), 4.00 (s, 3H), 3.96 (s, 3H), 3.80 (m, 2H), 3.55 (m, 2H), 3.17-3.12 (m, 4H), 2.99 (m, 2H), 2.75 (t, 2H, J=8.3 Hz), 2.36 (s, 3H);
IR (KBr): δ ppm 2923, 1644, 1601, 1504, 1466, 1253, 1146, 1023, 758 cm$^{-1}$;
MS (FAB+) m/z 516 [MH$^+$].

Example 80

1-(4-benzyl-piperazin-1-yl)-2-[2-(3,4-dimethoxy-phenyl)-3-methylsulfanyl-benzofuran-5-yl]-ethanone (37c)

Through similar procedure to the method disclosed in Example 78, white solid type of 1-(4-benzyl-piperazin-1-yl)-2-[2-(3,4-dimethoxy-phenyl)-3-methylsulfanyl-benzofuran-5-yl]-ethanone (37c; 114 mg) showing following physicochemical property was obtained (yield: 98.2%).

m.p: 70° C.;
$^1$H NMR (CDCl$_3$): δ ppm d 7.91 (m, 2H); d 7.50 (d, 1H, J=1.44), 7.42 (d, 1H, J=8.43 Hz), 7.3-7.2 (m, 5H), 7.15 (dd, 1H, J=8.4 & J=81.83 Hz), 6.99 (d, 1H, J=8.22 Hz), 4.0 (s, 3H), 3.96 (s, 3H), 3.86 (s, 2H), 3.73 (t, 2H, J=4.59), 3.55 (m, 4H), 2.52 (t, 2H, J=4.77), 2.35 (m, 5H);
IR (KBr): δ ppm 2922, 1642, 1509, 1465, 1348, 1253, 1144, 989, 754, 699 cm$^{-1}$;
MS (FAB+) m/z 517 [MH$^+$].

Example 81

1-(4-benzyl-piperazin-1-yl)-3-[2-(3,4-dimethoxy-phenyl)-3-methylsulfanyl-benzofuran-5-yl]-propan-1-one (37d)

Through similar procedure to the method disclosed in Example 78, white solid type of 1-(4-benzyl-piperazin-1-yl)-3-[2-(3,4-dimethoxy-phenyl)-3-methylsulfanyl-benzofuran-5-yl]-propan-1-one (37d; 102 mg) showing following physicochemical property was obtained (yield: 97%).

m.p: 100~102° C.;
$^1$H NMR (CDCl$_3$+CD$_3$OD): δ ppm d 7.99 (d, 1H, J=1.8 Hz), 7.95 (dd, 1H, J=8.4, 2.0 Hz), 7.51 (d, 1H), 7.45 (d, 1H, J=8.4 Hz), 7.27-7.17 (m, 6H), 7.06 (d, 1H, J=8.4 Hz), 3.99 (s, 3H), 3.96 (s, 3H), 3.61 (m, 2H), 3.37 (m, 4H), 3.10 (t, 2H, J=7.1 Hz), 2.38 (m, 5H), 2.04 (m, 2H);

IR (KBr): δ ppm 2925, 1642, 1509, 1467, 1347, 1254, 1145, 1000, 753 cm$^{-1}$;
MS (FAB+) m/z 531 [MH$^+$].

Example 82

2-[2-(3,4-dimethoxy-phenyl)-benzofuran-5-yl]-1-(4-phenyl-piperazin-1-yl)-ethanone (38a)

Through similar procedure to the method disclosed in Example 78, white solid type of 2-[2-(3,4-dimethoxy-phenyl)-benzofuran-5-yl]-1-(4-phenyl-piperazin-1-yl)-ethanone (38a; 95 mg) showing following physicochemical property was obtained (yield: 92%).
m.p: 54° C.;
$^1$H NMR (CDCl$_3$): δ ppm d 7.4-7.2 (m, 9H), 7.07 (d, 1, J=6.96 Hz), 6.4 (d, 1H, J=8.43 Hz), 6.82 (s, 1H), 3.99 (s, 3H), 3.93 (s, 3H), 3.81 (s, 2H), 3.73 (s, 2H), 3.55 (s, 4H), 2.54 (s, 2H), 2.33 (s, 2H);
IR (KBr): δ ppm 2936, 1640, 1511, 1465, 1346, 1253, 1142, 989, 862, 801, 754, 701 cm$^{-1}$;
MS (FAB+) m/z 471 [MH$^+$].

Example 83

3-[2-(3,4-dimethoxy-phenyl)-benzofuran-5-yl]-1-(4-phenyl-piperazin-1-yl)-propan-1-one (38b)

Through similar procedure to the method disclosed in Example 78, white solid type of 3-[2-(3,4-dimethoxy-phenyl)-benzofuran-5-yl]-1-(4-phenyl-piperazin-1-yl)-propan-1-one (38b; 86 mg) showing following physicochemical property was obtained (yield: 98%).
m.p: 122~124° C.;
$^1$H NMR (CDCl$_3$): δ ppm d 7.44-7.35 (m, 4H), 7.26-7.21 (m, 2H), 7.12 (dd, 1H), 6.96-6.84 (m, 5H), 3.99 (s, 3H), 3.94 (s, 3H), 3.79 (t, 2H), 3.53 (t, 2H), 3.12-3.06 (m, 4H), 2.97 (t, 2H), 2.72 (t, 2H, J=8.3 Hz);
IR (KBr): δ ppm 2924, 1645, 1510, 1464, 1253, 1144, 1023 cm$^{-1}$;
MS (FAB+) m/z 471 [MH$^+$].

Example 84

1-(4-benzyl-piperazin-1-yl)-2-[2-(3,4-dimethoxy-phenyl)-benzofuran-5-yl]-ethanone (38c)

Through similar procedure to the method disclosed in Example 78, white solid type of 1-(4-benzyl-piperazin-1-yl)-2-[2-(3,4-dimethoxy-phenyl)-benzofuran-5-yl]-ethanone (38c; 97 mg) showing following physicochemical property was obtained (yield: 93.4%).
m.p: 129° C.;
$^1$H NMR (CDCl$_3$): δ ppm d 7.42 (m, 3H), d 7.24 (m, 2H) 7.15 (m, 1H), 6.94 (d, 1H, J=8.61 Hz), 6.88 (s, 2H), 6.86 (s, 2H), 3.99 (s, 3H), 3.94 (s, 3H), 3.88 (s, 2H), 3.83 (s, 2H), 3.65 (s, 2H), 3.16 (s, 2H), 2.98 (s, 2H);
IR (KBr): δ ppm 2917, 1601, 1512, 1466, 1342, 1252, 1143, 1022, 862, 758, 694 cm$^{-1}$;
MS (FAB+) m/z 457 [MH$^+$].

Example 85

1-(4-benzyl-piperazin-1-yl)-3-[2-(3,4-dimethoxy-phenyl)-benzofuran-5-yl]-propan-1-one (38d)

Through similar procedure to the method disclosed in Example 78, white solid type of 1-(4-benzyl-piperazin-1-yl)-3-[2-(3,4-dimethoxy-phenyl)-benzofuran-5-yl]-propan-1-one (38d; 96 mg) showing following physicochemical property was obtained (yield: 98%).
m.p: 87~89° C.;
$^1$H NMR (CDCl$_3$): δ ppm d 7.45-7.23 (m, 9H), 7.09 (dd, 1H), 6.95 (d, 1H, J=8.6 Hz), 6.85 (s, 1H), 4.00 (s, 3H), 3.94 (s, 3H), 3.64 (t, 2H), 3.44 (s, 2H), 3.37 (t, 2H), 3.06 (t, 2H, J=7.0 Hz), 2.66 (t, 2H, J=7.9 Hz), 2.40 (t, 2H), 2.20 (t, 2H);
IR (KBr): δ ppm 2928, 1643, 1511, 1465, 1254, 1142, 1023 cm$^{-1}$;
MS (FAB+) m/z 485 [MH$^+$].

Example 86

2-[2-(3,4-dimethoxy-phenyl)-3-methylsulfanyl-benzofuran-5-yl]-ethanol (39a)

Through similar procedure to the method disclosed in Example 13, white solid type of 2-[2-(3,4-dimethoxy-phenyl)-3-methylsulfanyl-benzofuran-5-yl]-ethanol (39a; 164 mg) showing following physicochemical property was obtained (yield: 90%).
m.p: 96° C.;
$^1$H NMR (CDCl$_3$): δ ppm d 7.92 (s, 1H), 7.89 (d, 1H, J=1.83 Hz), 7.53 (d, 1H, J=1.65 Hz), 7.44 (d, 1H, J=8.25 Hz), 7.17 (dd, 1H, J=8.43 & 1.65 Hz), 6.97 (d, 1H, J=8.04), 4.0 (s, 3H), 3.95 (s, 3H), 3.92 (t, 2H, J=6.6 Hz), 3.0 (t, 2H, J=6.42), 2.38 (s, 3H);
IR (KBr): δ ppm 3499, 2925, 1507, 1466, 1253, 1144, 1026, 860, 807, 760 cm$^{-1}$;
MS (FAB+) m/z 344 [M$^+$].

Example 87

3-[2-(3,4-dimethoxy-phenyl)-3-methylsulfanyl-benzofuran-5-yl]-propan-1-ol (39b)

Through similar procedure to the method disclosed in Example 13, white solid type of 3-[2-(3,4-dimethoxy-phenyl)-3-methylsulfanyl-benzofuran-5-yl]-propan-1-ol (39b, 184 mg) showing following physicochemical property was obtained (yield: 99%).
m.p: 87~89° C.;
$^1$H NMR (CDCl$_3$): δ ppm d 7.92-7.89 (m, 2H), 7.51 (s, 1H), 7.42 (d, 1H, J=8.4 Hz), 7.16 (d, 1H, J=8.0 Hz), 6.98 (d, 1H, J=8.3 Hz), 4.00 (s, 3H), 3.96 (s, 3H), 3.73 (t, 2H, J=6.1 Hz), 2.85 (t, 2H, J=7.3 Hz), 2.38 (s, 3H), 1.98 (m, 2H);
IR (KBr): δ ppm 3365, 2926, 1605, 1506, 1467, 1254, 1174, 1145, 1027 cm$^{-1}$;
MS (FAB+) m/z 358 [M$^+$].

Example 88

2-[2-(3,4-dimethoxy-phenyl)-benzofuran-5-yl]-ethanol (40a)

Through similar procedure to the method disclosed in Example 13, white solid type of 2-[2-(3,4-dimethoxy-phenyl)-benzofuran-5-yl]-ethanol (40a, 225 mg) showing following physicochemical property was obtained (yield: 97%).
m.p: 122° C.;
$^1$H NMR (CDCl$_3$): δ ppm d 7.47-7.41 (m, 3H), 7.38 (m, 1H), 7.14 (m, 1H), 6.95 (d, 1H, J=8.25 Hz), 6.87 (s, 1H), 4.0 (s, 3H), 3.94 (s, 3H), 3.85 (t, 2H, J=7.1 Hz), 2.96 (t, 2H, J=6.6 Hz);
IR (KBr): δ ppm 3394, 2933, 1608, 1511, 1466, 1252, 1142, 1025, 941, 860, 804, 762 cm$^{-1}$;
MS (FAB+) m/z 298 [M$^+$].

Example 89

3-[2-(3,4-dimethoxy-phenyl)-benzofuran-5-yl]-propan-1-ol (40b)

Through similar procedure to the method disclosed in Example 13, white solid type of 3-[2-(3,4-dimethoxy-phenyl)-benzofuran-5-yl]-propan-1-ol (40b, 235 mg) showing following physicochemical property was obtained (yield: 76%).

m.p: 99~101° C.;
$^1$H NMR (CDCl$_3$): δ ppm d 7.45-7.36 (m, 4H), 7.10 (dd, 1H), 6.94 (d, 1H, J=8.4 Hz), 6.86 (d, 1H), 4.00 (s, 3H), 3.94 (s, 3H), 3.71 (m, 2H), 2.81 (t, 2H, J=7.5 Hz), 2.00-1.90 (m, 2H);
IR(KBr): δ ppm 3339, 2926, 1513, 1469, 1256, 1228, 1169, 1143, 1023 cm$^{-1}$;
MS (FAB+) m/z 312 [M$^+$].

Example 90

3-(2-(4-hydroxy-3-methoxyphenyl)-3-(methylthio)benzofuran-5-yl)-N,N-dipropylpropanamide Through similar procedure to the method disclosed in Example 59, 3-(2-(4-hydroxy-3-methoxyphenyl)-3-(methylthio)benzofuran-5-yl)-N,N dipropylpropanamide showing following physicochemical property was obtained.
Yield: 81%;
m.p: 185° C.;
$^1$H NMR (CDCl$_3$): δ ppm 7.85-7.89 (dd, 1H, J=1.8, 8.4 Hz, H-6'), 7.51 (s, 1H), 7.40 (d, 1H, J=8.4 Hz, H-5'), 7.17 (dd, 1H, J=8.2 Hz), 7.02 (d, 1H, J=8.2 Hz), 5.85 (s, 1H), 4.01 (s, 3H, OCH$_3$), 3.27 (t, 2H, J=8.7 Hz), 3.08-3.15 (m, 4H), 2.67 (t, 2H, J=8.7 Hz), 3.08-3.15 (m, 4H), 2.66 (t, 2H, J=6.3 Hz), 2.36 (s, 3H), 1.49-1.58 (m, 4H), 0.84-0.90 (m, 6H)

Example 91

3-(2-(4-hydroxy-3-methoxyphenyl)-3-(methylthio)benzofuran-5-yl)-1-(piperidin-1-yl)propan-1-one Through similar procedure to the method disclosed in Example 78, 3-(2-(4-hydroxy-3-methoxyphenyl)-3-(methylthio)benzofuran-5-yl)-1-(piperidin-1-yl)propan-1-one showing following physicochemical property was obtained
Yield: 71%;
m.p: 147° C.;
$^1$H NMR (CDCl$_3$): δ ppm 7.85-7.89 (dd, 1H, J=1.8, 8.4 Hz, H-6'), 7.51 (s, 1H), 7.40 (d, 1H, J=8.4 Hz, H-5'), 7.17 (dd, 1H, J=8.2 Hz), 7.02 (d, 1H, J=8.2 Hz), 5.82 (s, 1H), 4.01 (s, 3H, OCH$_3$), 3.57 (t, 2H, J=8.7 Hz), 3.36 (t, 2H, J=8.7 Hz), 3.08 (t, 2H, J=6.3 Hz), 2.69 (t, 2H, J=6.3 Hz), 2.36 (s, 3H), 1.56 (m, 6H)

Example 92

3-(2-(4-hydroxy-3-methoxyphenyl)-3-(methylthio)benzofuran-5-yl)-1-(pyrrolidin-1-yl)propan-1-one Through similar procedure to the method disclosed in Example 78, 3-(2-(4-hydroxy-3-methoxyphenyl)-3-(methylthio)benzofuran-5-yl)-1-(pyrrolidin-1-yl)propan-1-one showing following physicochemical property was obtained
Yield: 75%;
m.p: 155° C.;
$^1$H NMR (CDCl$_3$): δ ppm 7.85-7.89 (dd, 1H, J=1.8, 8.4 Hz, H-6'), 7.51 (s, 1H), 7.40 (d, 1H, J=8.4 Hz, H-5'), 7.17 (dd, 1H, J=8.2 Hz), 7.02 (d, 1H, J=8.2 Hz), 5.83 (s, 1H), 4.01 (s, 3H, OCH$_3$), 3.50 (t, 2H, J=8.7 Hz), 3.30 (t, 2H, J=8.7 Hz), 3.12 (t, 2H, J=6.3 Hz), 2.64 (t, 2H, J=6.3 Hz), 2.37 (s, 3H), 1.84 (m, 4H)

Example 93

3-(2-(3,4-Dimethoxyphenyl)-3-(methylthio)benzofuran-5-yl)-N,N-dipropylpropanamide Through similar procedure to the method disclosed in Example 59, 3-(2-(3,4-Dimethoxyphenyl)3-(methylthio)benzofuran-5-yl)-N,N-dipropylpropanamide showing following physicochemical property was obtained
Yield: 84%;
m.p: 116° C.;
$^1$H NMR (CDCl$_3$): δ ppm 7.90 (dd, 1H, J=1.8, 8.4 Hz, H-6'), 7.52 (s, 1H), 7.41 (d, 1H, J=8.4 Hz, H-5'), 7.17 (dd, 1H, J=8.2 Hz), 6.98 (d, 1H, J=8.2 Hz), 4.00 (s, 3H, OCH$_3$), 3.95 (s, 3H), 3.28 (t, 2H, J=8.7 Hz), 3.08-3.12 (m, 4H), 2.67 (t, 2H, J=8.7 Hz), 3.08-3.15 (m, 4H), 2.66 (t, 2H, J=6.3 Hz), 2.37 (s, 3H), 1.49-1.54 (m, 4H), 0.84-0.90 (m, 6H)

Example 94

3-(2-(3,4-Dmethoxyphenyl)-3-(methylthio)benzofuran-5-yl)-1-(piperidin-1-yl)propan-1-one Through similar procedure to the method disclosed in Example 78, 3-(2-(3,4-Dmethoxyphenyl)-3-(methylthio)benzofuran-5-yl)-1-(piperidin-1-yl)propan-1-one showing following physicochemical property was obtained
Yield: 78%;
m.p: 124° C.;
$^1$H NMR (CDCl$_3$): δ ppm 7.90 (dd, 1H, J=1.8, 8.4 Hz, H-6'), 7.52 (s, 1H), 7.41 (d, 1H, J=8.4 Hz, H-5'), 7.17 (dd, 1H, J=8.2 Hz), 6.98 (d, 1H, J=8.2 Hz), 4.00 (s, 3H, OCH$_3$), 3.95 (s, 3H), 3.57 (t, 2H, J=8.7 Hz), 3.36 (t, 2H, J=8.7 Hz), 3.10 (t, 2H, J=6.3 Hz), 2.69 (t, 2H, J=6.3 Hz), 2.37 (s, 3H), 1.56 (m, 6H)

Example 95

3-(2-(3,4-Dmethoxyphenyl)-3-(methylthio)benzofuran-5-yl)-1-(pyrrolidin-1-yl)propan-1-one Through similar procedure to the method disclosed in Example 78, 3-(2-(3,4-Dmethoxyphenyl)-3-(methylthio)benzofuran-5-yl)-1-(pyrrolidin-1-yl)propan-1-one showing following physicochemical property was obtained
Yield: 79%;
m.p: 117° C.;
$^1$H NMR (CDCl$_3$): δ ppm 7.90 (dd, 1H, J=1.8, 8.4 Hz, H-6'), 7.52 (s, 1H), 7.41 (d, 1H, J=8.4 Hz, H-5'), 7.17 (dd, 1H, J=8.2 Hz), 6.98 (d, 1H, J=8.2 Hz), 4.00 (s, 3H, OCH$_3$), 3.95 (s, 3H), 3.49 (t, 2H, J=8.7 Hz), 3.31 (t, 2H, J=8.7 Hz), 3.12 (t, 2H, J=6.3 Hz), 2.63 (t, 2H, J=6.3 Hz), 2.37 (s, 3H), 1.84 (m, 4H)

Example 96

2-(2-(4-hydroxy-3-methoxyphenyl)-3-(methylthio)benzofuran-5-yl)-1-(piperidin-1-yl)ethanone Through similar procedure to the method disclosed in Example 78, 2-(2-(4-hydroxy-3-methoxyphenyl)-3-(methylthio)benzofuran-5-yl)-1-(piperidin-1-yl)ethanone showing following physicochemical property was obtained.

Yield: 80%;
m.p.: 143.5° C.;
¹H NMR (CDCl₃): δ ppm 7.42-7.48 (m, 4H, Ar), 7.20 (dd, 1H, J=1.8, 8.4 Hz, H-6), 7.11 (d, 1H, J=8.2 Hz, H-7), 6.96 (S, 1H, H-3), 5.85 (bs, 1H), 4.40 (d, 1H, 6.3 Hz), 4.00 (s, 3H), 3.92-3.86 (m, 3H), 2.96 (m, 1H), 2.59 (m, 1H), 2.34 (s, 3H, SCH₃), 1.57-1.69 (m, 2H), 1.08 (m, 1H), 0.88-0.90 (m, 4H)

Example 97

2-(2-(4-hydroxy-3-methoxyphenyl)-3-(methylthio) benzofuran-5-yl)-1-((2S,6R)-2,6-dimethylmorpholino)ethanone Through similar procedure to the method disclosed in Example 78, 2-(2-(4-hydroxy-3-methoxyphenyl)-3-(methylthio)benzofuran-5-yl)-1-((2S,6R)-2,6-dimethylmorpholino)ethanone showing following physicochemical property was obtained.

Yield: 75%;
m.p.: 82° C.;
¹H NMR (CDCl₃): δ ppm 7:42-7.48 (m, 4H, Ar), 7.20 (dd, 1H, J=1.8, 8.4 Hz, H-6), 7.11 (d, 1H, J=8.2 Hz, H-7), 6.96 (S, 1H, H-3), 5.84 (bs, 1H), 4.51 (d, 1H, 13.3 Hz), 4.01 (s, 3H), 3.86 (s, 2H), 3.72 (d, 1H, J=13.2 Hz), 3.49 (m, 1H), 3.26 (m, 1H), 2.75 (m, 1H), 2.31-2.39 (m, 4H), 1.18 (d, 3H, J=6.3 Hz), 1.08 (d, 3H, J=6.3 Hz)

Example 98

2-(2-(4-hydroxy-3-methoxyphenyl)-3-(methylthio) benzofuran-5-yl)-N,N-dimethylacetamide Through similar procedure to the method disclosed in Example 59, 2-(2-(4-hydroxy-3-methoxyphenyl)-3-(methylthio)benzofuran-5-yl)-N,N-dimethylacetamide showing following physicochemical property was obtained.

Yield: 75%;
m.p.: 154.2° C.;
¹H NMR (CDCl₃): δ ppm 7.42-7.48 (m, 4H, Ar), 7.20 (dd, 1H, J=1.8, 8.4 Hz, H-6), 7.11 (d, 1H, J=8.2 Hz, H-7), 6.96 (S, 1H, H-3), 5.89 (bs, 1H), 4.00 (s, 3H), 3.84 (s, 2H), 3.05 (s, 3H), 2.99 (s, 3H), 2.35 (s, 3H)

Example 99

2-(2-(4-hydroxy-3-methoxyphenyl)-3-(methylthio) benzofuran-5-yl)-1-(4-methylpiperazin-1-yl)ethanone Through similar procedure to the method disclosed in Example 78, 2-(2-(4-hydroxy-3-methoxyphenyl)-3-(methylthio)benzofuran-5-yl)-1-(4-methylpiperazin-1-yl)ethanone showing following physicochemical property was obtained.

Yield: 65%;
m.p.: 167.9° C.;
¹H NMR (CDCl₃): δ ppm 7.42-7.48 (m, 4H, Ar), 7.20 (dd, 1H, J=1.8, 8.4 Hz, H-6), 7.11 (d, 1H, J=8.2 Hz, H-7), 6.96 (S, 1H, H-3), 5.89 (bs, 1H), 4.29 (m, 1H), 4.00 (s, 3H), 3.86 (s, 2H), 3.71-3.75 (m, 2H), 3.48-3.58 (m, 2H), 2.35-2.40 (m, 5H), 2.26 (m, 4H), 0.77-0.89 (m, 3H)

Example 100

Methyl 2-(2-(4-acetoxy-3-methoxyphenyl)-3-(methylthio)benzofuran-5-yl)propanoate Through similar procedure to the method disclosed in Example 5, Methyl 2-(2-(4-acetoxy-3-methoxyphenyl)-3-(methylthio)benzofuran-5-yl)propanoate showing following physicochemical property was obtained.

Yield: 55%;
¹H NMR (CDCl₃): δ ppm 7.90-8.01 (m, 3H, Ar), 7.62 (s, 1H), 7.45 (d, 1H, J=8.2 Hz, H-7), 7.25-7.30 (m, 2H), 7.14 (d, 1H, J=8.4 Hz), 3.94 (s, 3H), 3.87 (q, 1H, J=6.3 Hz), 3.68 (s, 3H), 2.38 (s, 3H, SCH₃), 2.35 (s, 3H), 1.59 (d, 3H, J=6.3 Hz), 1.08 (m, 1H), 0.88-0.90 (m, 4H)

Example 101

2-(2-(4-hydroxy-3-methoxyphenyl)-3-(methylthio) benzofuran-5-yl)-1-(piperidin-1-yl)propan-1-one Through similar procedure to the method disclosed in Example 78, 2-(2-(4-hydroxy-3-methoxyphenyl)-3-(methylthio)benzofuran-5-yl)-1-(piperidin-1-yl)propan-1-one showing following physicochemical property was obtained.

Yield: 55%;
m.p.: 168° C.;
¹H NMR (CDCl₃): δ ppm 7.42-7.48 (m, 4H, Ar), 7.21 (dd, 1H, J=1.8, 8.4 Hz, H-6), 7.01 (d, 1H, J=8.2 Hz, H-7), 6.96 (S, 1H, H-3), 5.88 (bs, 1H), 4.00-4.06 (m, 4H), 3.77 (m, 1H), 3.32-3.43 (m, 3H), 2.35 (s, 3H), 1.51 (d, 3H, J=6.9 Hz)

Example 102

N,N-Diethyl-2-(2-(4-hydroxy-3-methoxyphenyl)-3-(methylthio)benzofuran-5-yl)propanamide Through similar procedure to the method disclosed in Example 59, N,N-Diethyl-2-(2-(4-hydroxy-3-methoxyphenyl)-3-(methylthio)benzofuran-5-yl)propanamide showing following physicochemical property was obtained.

Yield: 65%;
m.p.: 200° C.;
¹H NMR (CDCl₃): δ ppm 7.42-7.48 (m, 4H, Ar), 7.21 (dd, 1H, J=1.8, 8.4 Hz, H-6), 7.01 (d, 1H, J=8.2 Hz, H-7), 6.96 (S, 1H, H-3), 5.88 (bs, 1H), 3.93-4.00 (m, 4H), 3.38 (m, 1H), 3.07-3.28 (m, 2H), 2.35 (s, 3H), 1.51 (d, 3H, J=6.9 Hz), 1.10 (t, 3H, J=6.9 Hz), 1.01 (t, 3H, J=6.9 Hz)

Example 103

2-(2-(3,4-Dimethoxyphenyl)-3-(methylthio)benzofuran-5-yl)-1-(piperidin-1-yl)ethanone Through similar procedure to the method disclosed in Example 78, 2-(2-(3,4-Dimethoxyphenyl)-3-(methylthio)benzofuran-5-yl)-1-(piperidin-1-yl)ethanone showing following physicochemical property was obtained.

Yield: 72%;
m.p.: 126° C.;
¹H NMR (CDCl₃): δ ppm 7.42-7.48 (m, 4H, Ar), 7.21 (dd, 1H, J=1.8, 8.4 Hz, H-6), 7.01 (d, 1H, J=8.2 Hz, H-7), 6.96 (S, 1H, H-3), 3.99 (s, 3H), 3.93 (s, 3H), 3.86 (s, 2H), 3.60 (m, 2H), 3.43 (m, 2H), 2.36 (s, 3H), 1.36 (m, 2H)

Example 104

2-(2-(3,4-Dimethoxyphenyl)-3-(methylthio)benzofuran-5-yl)-1-(pyrrolidin-1-yl)ethanone Through similar procedure to the method disclosed in Example 78, 2-(2-(3,4-Dimethoxyphenyl)-3-(methylthio) benzofuran-5-yl)-1-(pyrrolidin-1-yl)ethanone showing following physicochemical property was obtained.
Yield: 80%;
m.p.: 138° C.;
$^1$H NMR (CDCl$_3$): δ ppm 7.42-7.48 (m, 4H, Ar), 7.21 (dd, 1H, J=1.8, 8.4 Hz, H-6), 7.01 (d, 1H, J=8.2 Hz, H-7), 6.96 (S, 1H, H-3), 3.99 (s, 3H), 3.93 (s, 3H), 3.78 (s, 2H), 3.50 (m, 4H), 2.37 (s, 3H), 1.89 (m, 4H)

Example 105

2-(2-(3,4-Dimethoxyphenyl)-3-(methylthio)benzofuran-5-yl)-1-morpholinoethanone

Through similar procedure to the method disclosed in Example 78, 2-(2-(3,4-Dimethoxyphenyl)-3-(methylthio) benzofuran-5-yl)-1-morpholinoethanone showing following physicochemical property was obtained.
Yield: 62%;
m.p.: 155° C.;
$^1$H NMR (CDCl$_3$): δ ppm 7.42-7.48 (m, 4H, Ar), 7.21 (dd, 1H, J=1.8, 8.4 Hz, H-6), 7.01 (d, 1H, J=8.2 Hz, H-7), 6.96 (S, 1H, H-3), 3.99 (s, 3H), 3.93 (s, 3H), 3.86 (s, 2H), 3.67 (bs, 4H), 3.50 (bs, 4H), 2.37 (s, 3H)

Example 106

2-(2-(3,4-Dimethoxyphenyl)-3-(methylthio)benzofuran-5-yl)-1-(4-methylpiperidin-1-yl)ethanone Through similar procedure to the method disclosed in Example 78, 2-(2-(3,4-Dimethoxyphenyl)-3-(methylthio) benzofuran-5-yl)-1-(4-methylpiperidin-1-yl)ethanone showing following physicochemical property was obtained.
Yield: 82%;
m.p.: 83° C.;
$^1$H NMR (CDCl$_3$): δ ppm 7.42-7.48 (m, 4H, Ar), 7.21 (dd, 1H, J=1.8, 8.4 Hz, H-6), 7.01 (d, 1H, J=8.2 Hz, H-7), 6.96 (S, 1H, H-3), 4.65 (m, 1H), 3.99 (s, 3H), 3.93 (s, 3H), 3.86 (s, 2H), 2.96 (m, 2H), 2.58 (m, 1H), 2.36 (s, 3H), 1.53-1.69 (m, 8H), 1.11 (m, 1H), 0.88 (d, 3H, J=6.3 Hz)

Example 107

2-(2-(3,4-Dimethoxyphenyl)-3-(methylthio)benzofuran-5-yl)-1-((2S,6R)-2,6-dimethylmorpholino)ethanone Through similar procedure to the method disclosed in Example 78, 2-(2-(3,4-Dimethoxyphenyl)-3-(methylthio) benzofuran-5-yl)-1-((2S,6R)-2,6-dimethylmorpholino)ethanone showing following physicochemical property was obtained.
Yield: 52%;
m.p.: 147° C.;
$^1$H NMR (CDCl$_3$): δ ppm 7.42-7.48 (m, 4H, Ar), 7.21 (dd, 1H, J=1.8, 8.4 Hz, H-6), 7.01 (d, 1H, J=8.2 Hz, H-7), 6.96 (S, 1H, H-3), 4.51 (d, 1H, 13.3 Hz), 3.99 (s, 3H), 3.93 (s, 3H), 3.86 (s, 2H), 3.72 (d, 1H, J=13.2 Hz), 3.49 (m, 1H), 3.26 (m, 1H), 2.75 (m, 1H), 2.31-2.39 (m, 1H), 1.18 (d, 3H, J=6.3 Hz), 1.08 (d, 3H, J=6.3 Hz), Example 108

2-(2-(3,4-Dimethoxyphenyl)-3-(methylthio)benzofuran-5-yl)-N-propylacetamide

Through similar procedure to the method disclosed in Example 59, 2-(2-(3,4-Dimethoxyphenyl)-3-(methylthio) benzofuran-5-yl)-N-propylacetamide showing following physicochemical property was obtained.
Yield: 78%;
$^1$H NMR (CDCl$_3$): δ ppm 7.42-7.48 (m, 4H, Ar), 7.21 (dd, 1H, J=1.8, 8.4 Hz, H-6), 7.01 (d, 1H, J=8.2 Hz, H-7), 6.96 (S, 1H, H-3), 4.73 (d, 1H, J=6.9 Hz), 3.99 (s, 3H), 3.93 (s, 3H), 3.84 (s, 2H), 2.45-2.93 (m, 4H), 2.36 (s, 3H), 1.60-1.77 (m, 4H)

Example 109

N,N-Diethyl-3-(2-(3,4-dimethoxyphenyl)benzofuran-5-yl)propanamide

Through similar procedure to the method disclosed in Example 13, N,N-Diethyl-3-(2-(3,4-dimethoxyphenyl)benzofuran-5-yl)propanamide showing following physicochemical property was obtained.
Yield: 64%;
m.p.: 164.3° C.;
$^1$H NMR (CDCl$_3$): δ ppm 7.36-7.44 (m, 4H, Ar), 7.09 (dd, 1H, J=1.8, 8.4 Hz, H-6), 6.93 (d, 1H, J=8.2 Hz, H-7), 6.84 (S, 1H, H-3), 3.98 (s, 3H), 3.93 (s, 3H), 3.36 (q, 2H, J=6.9 Hz), 3.19 (q, 2H, J=6.9 Hz), 3.05 (t, 2H, J=8.4 Hz), 2.65 (t, 2H, J=8.4 Hz), 1.08 (m, 6H)

Example 110

N3-(2-(3,4-Dimethoxyphenyl)benzofuran-5-yl)-1-(pyrrolidin-1-yl)propan-1-one

Through similar procedure to the method disclosed in Example 78, 3-(2-(3,4-Dimethoxyphenyl)benzofuran-5-yl)-1-(pyrrolidin-1-yl)propan-1-one showing following physicochemical property was obtained.
Yield: 54%;
m.p.: 157.2° C.;
$^1$H NMR (CDCl$_3$): δ ppm 7.36-7.44 (m, 4H, Ar), 7.09 (dd, 1H, J=1.8, 8.4 Hz, H-6), 6.93 (d, 1H, J=8.2 Hz, H-7), 6.84 (S, 1H, H-3), 3.99 (s, 3H), 3.93 (s, 3H), 3.45 (m, 2H), 3.26 (m, 2H), 3.05 (t, 2H, J=8.4 Hz), 2.62 (t, 2H, J=8.4 Hz), 1.77-1.86 (m, 4H)

Example 111

3-(2-(3,4-Dimethoxyphenyl)benzofuran-5-yl)-1-(piperidin-1-yl)propan-1-one

Through similar procedure to the method disclosed in Example 78, 3-(2-(3,4-Dimethoxyphenyl)benzofuran-5-yl)-1-(piperidin-1-yl)propan-1-one showing following physicochemical property was obtained.
Yield: 65%;
m.p.: 129.6° C.;

¹H NMR (CDCl₃): δ ppm 7.36-7.44 (m, 4H, Ar), 7.09 (dd, 1H, J=1.8, 8.4 Hz, H-6), 6.93 (d, 1H, J=8.2 Hz, H-7), 6.85 (S, 1H, H-3), 3.99 (s, 3H), 3.93 (s, 3H), 3.57 (m, 2H), 3.33 (m, 2H), 3.06 (t, 2H, J=8.4 Hz), 2.70 (t, 2H, J=8.4 Hz), 1.43-1.59 (m, 6H)

Example 112

3-(2-(3,4-Dimethoxyphenyl)benzofuran-5-yl)-1-morpholinopropan-1-one

Through similar procedure to the method disclosed in Example 78, 3-(2-(3,4-Dimethoxyphenyl)benzofuran-5-yl)-1-morpholinopropan-1-one showing following physicochemical property was obtained.
Yield: 58%;
m.p.: 139.2° C.;
¹H NMR (CDCl₃): δ ppm 7.36-7.44 (m, 4H, Ar), 7.09 (dd, 1H, J=1.8, 8.4 Hz, H-6), 6.93 (d, 1H, J=8.2 Hz, H-7), 6.85 (S, 1H, H-3), 3.99 (s, 3H), 3.93 (s, 3H), 3.61 (bs, 4H), 3.47 (m, 2H), 3.35 (m, 2H), 3.06 (t, 2H, J=8.4 Hz), 2.70 (t, 2H, J=8.4 Hz)

Example 113

3-(2-(3,4-Dimethoxyphenyl)benzofuran-5-yl)-1-((2S,6R)-2,6-dimethylmorpholino)propan-1-one Through similar procedure to the method disclosed in Example 78, 3-(2-(3,4-Dimethoxyphenyl)benzofuran-5-yl)-1-(2S,6R)-2,6-dimethylmorpholino)propan-1-one showing following physicochemical property was obtained.
Yield: 59%;
m.p.: 163.2° C.;
¹H NMR (CDCl₃): δ ppm 7.36-7.44 (m, 4H, Ar), 7.09 (dd, 1H, J=1.8, 8.4 Hz, H-6), 6.93 (d, 1H, J=8.2 Hz, H-7), 6.85 (S, 1H, H-3), 4.46 (d, 1H, 13.3 Hz), 3.99 (s, 3H), 3.93 (s, 3H), 3.86 (s, 2H), 4.45-4.53 (m, 3H), 3.23 (m, 1H), 2.62-3.08 (m, 7H), 2.27 (m, 1H), 1.18 (d, 3H, J=6.3 Hz), 1.08 (d, 3H, J=6.3 Hz)

Example 114

2-(2-(4-Hydroxy-3-methoxyphenyl)benzofuran-5-yl)-1-(piperidin-1-yl)ethanone

Through similar procedure to the method disclosed in Example 78, 2-(2-(4-Hydroxy-3-methoxyphenyl)benzofuran-5-yl)-1-(piperidin-1-yl)ethanone showing following physicochemical property was obtained.
Yield: 59%;
m.p.: 151° C.;
¹H NMR (CDCl₃): δ ppm 7.35-7.44 (m, 4H, Ar), 7.13 (dd, 1H, J=1.8, 8.4 Hz, H-6), 6.98 (d, 1H, J=8.2 Hz, H-7), 6.82 (S, 1H, H-3), 5.78 (s, 1H), 4.00 (s, 3H), 3.81 (s, 2H), 3.58 (m, 2H), 3.41 (m, 2H), 1.55 (m, 2H), 1.33-1.35 (m, 3H)

Example 115

2-(2-(4-Hydroxy-3-methoxyphenyl)benzofuran-5-yl)-1-(pyrrolidin-1-yl)ethanone

Through similar procedure to the method disclosed in Example 78, 2-(2-(4-Hydroxy-3-methoxyphenyl)benzofuran-5-yl)-1-(pyrrolidin-1-yl)ethanone showing following physicochemical property was obtained.
Yield: 65%;
m.p.: 193° C.;
¹H NMR (CDCl₃): δ ppm 7.35-7.44 (m, 4H, Ar), 7.13 (dd, 1H, J=1.8, 8.4 Hz, H-6), 6.98 (d, 1H, J=8.2 Hz, H-7), 6.82 (S, 1H, H-3), 5.82 (s, 1H), 4.00 (s, 3H), 3.82 (s, 2H), 3.43-3.53 (m, 4H), 1.81-1.91 (m, 4H)

Example 116

N,N-Diethyl-2-(2-(4-hydroxy-3-methoxyphenyl)benzofuran-5-yl)acetamide

Through similar procedure to the method disclosed in Example 59, N,N-Diethyl-2-(2-(4-hydroxy-3-methoxyphenyl)benzofuran-5-yl)acetamide showing following physicochemical property was obtained.
Yield: 73%;
m.p.: 180° C.;
¹H NMR (CDCl₃): δ ppm 7.35-7.44 (m, 4H, Ar), 7.13 (dd, 1H, J=1.8, 8.4 Hz, H-6), 6.98 (d, 1H, J=8.2 Hz, H-7), 6.82 (S, 1H, H-3), 5.84 (s, 1H), 3.99 (s, 3H), 3.78 (s, 2H), 3.30-3.49 (m, 4H), 1.07-1.16 (m, 6H)

Example 117

2-(2-(4-Hydroxy-3-methoxyphenyl)benzofuran-5-yl)-N,N-dipropylacetamide

Through similar procedure to the method disclosed in Example 59, 2-(2-(4-Hydroxy-3-methoxyphenyl)benzofuran-5-yl)-N,N-dipropylacetamide showing following physicochemical property was obtained.
Yield: 77%;
m.p.: 122° C.;
¹H NMR (CDCl₃): δ ppm 7.35-7.44 (m, 4H, Ar), 7.13 (dd, 1H, J=1.8, 8.4 Hz, H-6), 6.98 (d, 1H, J=8.2 Hz, H-7), 6.82 (S, 1H, H-3), 5.84 (s, 1H), 4.00 (s, 3H), 3.78 (s, 2H), 3.19-3.33 (m, 4H), 1.25-1.61 (m, 4H), 0.85-0.90 (m, 6H)

Example 118

2-(2-(4-Hydroxy-3-methoxyphenyl)benzofuran-5-yl)-1-((2S,6R)-2,6-dimethylmorpholino)ethanone Through similar procedure to the method disclosed in Example 78, 2-(2-(4-Hydroxy-3-methoxyphenyl)benzofuran-5-yl)-1-((2S,6R)-2,6-dimethylmorpholino)ethanone showing following physicochemical property was obtained.
Yield: 78%;
m.p.: 189° C.;
¹H NMR (CDCl₃): δ ppm 7.35-7.44 (m, 4H, Ar), 7.13 (dd, 1H, J=1.8, 8.4 Hz, H-6), 6.98 (d, 1H, J=8.2 Hz, H-7), 6.82 (S, 1H, H-3), 5.80 (s, 1H), 4.50 (m, 1H), 4.00 (s, 3H), 3.81 (s, 2H), 3.72 (m, 1H), 3.48 (m, 1H), 3.23 (m, 1H), 2.73 (m, 1H), 2.33 (m, 1H), 1.18 (d, 3H, J=6.3 Hz), 1.08 (d, 3H, J=6.3 Hz)

Example 119

1-(4-Benzylpiperidin-1-yl)-2-(2-(4-hydroxy-3-methoxyphenyl)benzofuran-5-yl)ethanone Through similar procedure to the method disclosed in Example 78, 1-(4-Benzylpiperidin-1-yl)-2-(2-(4-hydroxy-3-methoxyphenyl)benzofuran-5-yl)ethanone showing following physicochemical property was obtained.
Yield: 73%;
m.p.: 198° C.;

¹H NMR (CDCl₃): δ ppm 7.43-7.45 (m, 2H, Ar), 7.25-7.39 (m, 2H), 7.22-7.27 (m, 3H), 7.14 (dd, 1H, J=1.8, 8.4 Hz), 6.97 (d, 1H, J=8.4 Hz, H-7), 6.82-6.90 (m, 4H), 4.00 (s, 3H), 3.80-3.87 (m, 4H), 3.64 (m, 2H), 3.14 (m, 2H), 2.97 (m, 2H), 1.28 (m, 2H), 0.86 (m, 1H)

Example 120

2-(2-(4-Hydroxy-3-methoxyphenyl)benzofuran-5-yl)-1-(4-phenylpiperazin-1-yl)ethanone Through similar procedure to the method disclosed in Example 78, 2-(2-(4-Hydroxy-3-methoxyphenyl)benzofuran-5-yl)-1-(4-phenylpiperazin-1-yl)ethanone showing following physicochemical property was obtained.

Yield: 74%;
m.p.: 145° C.;
¹H NMR (CDCl₃): δ ppm 7.36-7.43 (m, 4H, Ar), 7.06-7.23 (m, 5H), 6.98 (d, 1H, J=8.4 Hz), 6.82 (s, 1H), 4.68 (m, 1H), 4.01 (s, 3H), 3.85 (m, 1H), 3.80 (s, 2H), 3.74 (m, 1H), 2.89 (m, 1H), 2.48-2.52 (m, 3H), 1.85 (m, 1H)

Example 121

Methyl 2-(2-(4-acetoxy-3-methoxyphenyl)benzofuran-5-yl)propanoate

Through similar procedure to the method disclosed in Example 5, Methyl 2-(2-(4-acetoxy-3-methoxyphenyl)benzofuran-5-yl)propanoate showing following physicochemical property was obtained.

Yield: 76%;
¹H NMR (CDCl₃): 5 ppm 7.38-7.50 (m, 4H, Ar), 7.20-7.24 (m, 2H), 7.09 (d, 1H, J=8.4 Hz), 6.94 (s, 1H), 3.91 (s, 3H), 3.80 (q, 1H, J=6.3 Hz), 3.66 (s, 3H), 2.32 (s, 3H), 1.55 (d, 3H, J=6.3 Hz)

Example 122

2-(2-(4-Hydroxy-3-methoxyphenyl)benzofuran-5-yl)-1-(piperidin-1-yl)propan-1-one

Through similar procedure to the method disclosed in Example 78, 2-(2-(4-Hydroxy-3-methoxyphenyl)benzofuran-5-yl)-1-(piperidin-1-yl)propan-1-one showing following physicochemical property was obtained.

Yield: 76%;
m.p.: 199° C.;
¹H NMR (CDCl₃): 5 ppm 7.35-7.43 (m, 4H, Ar), 7.13 (d, 1H, J=8.4 Hz), 6.98 (d, 1H, J=8.4 Hz), 6.82 (s, 1H), 5.78 (bs, 1H), 3.93-4.00 (m, 5H), 3.74 (m, 1H), 3.32-3.46 (m, 4H), 1.48 (d, 3H, J=6.9 Hz), 1.25-1.29 (m, 4H)

Example 123

2-(2-(4-Hydroxy-3-methoxyphenyl)benzofuran-5-yl)-1-(4-methylpiperidin-1-yl)propan-1-one Through similar procedure to the method disclosed in Example 78, 2-(2-(4-Hydroxy-3-methoxyphenyl)benzofuran-5-yl)-1-(4-methylpiperidin-1-yl)propan-1-one showing following physicochemical property was obtained.

Yield: 79%;
m.p.: >200° C.;
¹H NMR (CDCl₃): δ ppm 7.36-7.43 (m, 4H, Ar), 7.06-7.23 (m, 5H), 4.64 (m, 1H), 3.74-4.00 (m, 5H), 2.91 (m, 1H), 2.50-2.62 (m, 2µl), 1.25-1.59 (m, 4H), 0.93 (d, 3H, J=6.6 Hz), 0.73 (d, 3H, J=6.6 Hz)

Example 124

2-(2-(4-Hydroxy-3-methoxyphenyl)benzofuran-5-yl)-1-morpholinopropan-1-one

Through similar procedure to the method disclosed in Example 78, 2-(2-(4-Hydroxy-3-methoxyphenyl)benzofuran-5-yl)-1-morpholinopropan-1-one showing following physicochemical property was obtained.

Yield: 63%;
m.p.: 188° C.;
¹H NMR (CDCl₃): δ ppm 7.36-7.43 (m, 4H, Ar), 7.06-7.23 (m, 5H), 3.99 (s, 3H), 3.93 (q, 1H, J=6.6 Hz), 3.62-3.83 (m, 2H), 3.37-3.57 (m, 6H), 1.50 (d, 3H, J=6.9 Hz)

Example 125

N,N-Diethyl-2-(2-(4-hydroxy-3-methoxyphenyl)benzofuran-5-yl)propanamide

Through similar procedure to the method disclosed in Example 59, N,N-Diethyl-2-(2-(4-hydroxy-3-methoxyphenyl)benzofuran-5-yl)propanamide showing following physicochemical property was obtained.

Yield: 73%;
m.p.: 192° C.;
¹H NMR (CDCl₃): δ ppm 7.36-7.43 (m, 4H, Ar), 7.06-7.23 (m, 5H), 5.76 (s, 1H), 4.00 (s, 3H), 3.91 (q, 1H), 3.50 (m, 1H), 3.48-3.11 (m, 3H), 1.48 (d, 3H), 1.09 (t, 3H), 0.99 (t, 3H, J=6.3 Hz)

Example 126

2-(2-(4-Hydroxy-3-methoxyphenyl)benzofuran-5-yl)-N,N-dimethylpropanamide

Through similar procedure to the method disclosed in Example 59, 2-(2-(4-Hydroxy-3-methoxyphenyl)benzofuran-5-yl)-N,N-dimethylpropanamide showing following physicochemical property was obtained.

Yield: 66%;
m.p.: 173° C.;
¹H NMR (CDCl₃): δ ppm 7.36-7.43 (m, 4H, Ar), 7.06-7.23 (m, 5H), 5.76 (s, 1H), 4.00 (s, 3H), 3.47 (q, 1HJ=6.9 Hz), 2.97 (s, 3H), 2.92 (s, 3H), 1.48 (d, 3H, J=6.3 Hz)

Example 127

2-(2-(4-Hydroxy-3-methoxyphenyl)benzofuran-5-yl)-N,N-dipropylpropanamide

Through similar procedure to the method disclosed in Example 59, 2-(2-(4-Hydroxy-3-methoxyphenyl)benzofuran-5-yl)-N,N-dipropylpropanamide showing following physicochemical property was obtained.

Yield: 73%;
m.p.: 160° C.;
¹H NMR (CDCl₃): δ ppm 7.36-7.43 (m, 4H, Ar), 7.06-7.23 (m, 5H), 3.89-4.00 (m, 4H), 3.46 (m, 1H), 3.29 (m, 1H), 2.93-3.15 (m, 2H), 1.25-1.55 (m, 5H), 0.84 (q, 6H, J=7.5 Hz)

Example 128

2-(2-(4-Hydroxy-3-methoxyphenyl)benzofuran-5-yl)-1-((2S,6R)-2,6-dimethylmorpholino)propan-1-one Through similar procedure to the method disclosed in Example 78, 2-(2-(4-Hydroxy-3-methoxyphenyl)benzofuran-5-yl)-1-((2S,6R)-2,6-dimethylmorpholino)propan-1-one showing following physicochemical property was obtained.

Yield: 53%;
m.p.: 115° C.;
$^1$H NMR (CDCl$_3$): δ ppm 7.36-7.43 (m, 4H, Ar), 7.06-7.23 (m, 5H), 5.76 (s, 1H), 4.54 (m, 1H), 4.01 (s, 3H), 3.90 (m, 1H), 3.72 (m, 1H), 3.45-3.80 (m, 2H) 2.70 (m, 1H), 2.32 (m, 1H) 1.56 (d, 3H, J=6.3 Hz), 1.18 (d, 3H, J=6.3 Hz), 1.08 (d, 3H, J=6.3 Hz)

Example 129

2-(2-(4-Hydroxy-3-methoxyphenyl)benzofuran-5-yl)-1-(pyrrolidin-1-yl)propan-1-one Through similar procedure to the method disclosed in Example 78, 2-(2-(4-Hydroxy-3-methoxyphenyl)benzofuran-5-yl)-1-(pyrrolidin-1-yl)propan-1-one showing following physicochemical property was obtained.

Yield: 77%;
m.p.: 172° C.;
$^1$H NMR (CDCl$_3$): δ ppm 7.36-7.43 (m, 4H, Ar), 7.06-7.23 (m, 5H), 4.00 (s, 3H), 3.80 (q, 1H, J=6.6 Hz), 3.21-3.56 (m, 4H), 1.76-1.-89 (m, 4H), 1.26 (d, 3H, J=6.9 Hz)

Example 130

2-(2-(4-Hydroxy-3-methoxyphenyl)benzofuran-5-yl)-N-propylpropanamide

Through similar procedure to the method disclosed in Example 59, 2-(2-(4-Hydroxy-3-methoxyphenyl)benzofuran-5-yl)-N-propylpropanamide showing following physicochemical property was obtained.

Yield: 89%;
m.p.: 146.9° C.;
$^1$H NMR (CDCl$_3$): δ ppm 7.36-7.43 (m, 4H, Ar), 7.06-7.23 (m, 5H), 5.78 (s, 1H), 5.33 (bs, 1H), 4.01 (s, 3H), 3.64 (q, 1H), 3.15 (q, 2H), 1.57 (d, 3H), 1.41 (m, 2H), 0.80 (t, 3H,)

Example 131

N,N-Diethyl-2-(2-(3,4-dimethoxyphenyl)benzofuran-5-yl)acetamide

Through similar procedure to the method disclosed in Example 59, N,N-Diethyl-2-(2-(3,4-dimethoxyphenyl)benzofuran-5-yl)acetamide showing following physicochemical property was obtained.

Yield: 77%;
m.p.: 134° C.;
$^1$H NMR (CDCl$_3$): δ ppm 7.36-7.45 (m, 4H, Ar), 7.14 (d, 1H, J=8.4 Hz), 6.90 (d, 1H, J=8.4 Hz), 6.85 (s, 1H), 3.99-3.93 (s, 3H), 3.78 (s, 2H), 3.30-3.47 (m, 4H), 1.02-1.16 (d, 6H)

Example 132

2-(2-(3,4-Dimethoxyphenyl)benzofuran-5-yl)-1-(piperidin-1-yl)ethanone

Through similar procedure to the method disclosed in Example 78, 2-(2-(3,4-Dimethoxyphenyl)benzofuran-5-yl)-1-(piperidin-1-yl)ethanone showing following physicochemical property was obtained Yield: 77%;
m.p.: 115° C.;
$^1$H NMR (CDCl$_3$): δ ppm 7.36-7.45 (m, 4H, Ar), 7.14 (d, 1H, J=8.4 Hz), 6.90 (d, 1H, J=8.4 Hz), 6.85 (s, 1H), 4.60 (d, 1H), 3.99 (s, 3H), 3.94 (s, 3H), 3.81 (s, 2H), 3.57-3.63 (m, 2H), 3.38-3.48 (m, 2H), 1.48-1.72 (m, 4H), 1.3-1.4 (m, 2H)

Example 133

2-(2-(3,4-Dimethoxyphenyl)benzofuran-5-yl)-1-(4-methylpiperidin-1-yl)ethanone

Through similar procedure to the method disclosed in Example 78, 2-(2-(3,4-Dimethoxyphenyl)benzofuran-5-yl)-1-(4-methylpiperidin-1-yl)ethanone showing following physicochemical property was obtained Yield: 77%;
m.p.: 139° C.;
$^1$H NMR (CDCl$_3$): δ ppm 7.36-7.45 (m, 4H, Ar), 7.14 (d, 1H, J=8.4 Hz), 6.90 (d, 1H, J=8.4 Hz), 6.85 (s, 1H), 4.60 (d, 1H), 3.99 (s, 3H), 3.94 (s, 3H), 3.81 (s, 2H), 2.94 (t, 1H), 2.98 (t, 1H), 1.47-1.72 (m, 5H), 1.00-1.03 (m, 1H), 0.88 (d, 3H)

Example 134

2-(2-(3,4-Dimethoxyphenyl)benzofuran-5-yl)-1-morpholinoethanone

Through similar procedure to the method disclosed in Example 78, 2-(2-(2-(3,4-Dimethoxyphenyl)benzofuran-5-yl)-1-morpholinoethanone showing following physicochemical property was obtained Yield: 77%;
m.p.: 130° C.;
$^1$H NMR (CDCl$_3$): δ ppm 7.36-7.45 (m, 4H, Ar), 7.14 (d, 1H, J=8.4 Hz), 6.90 (d, 1H, J=8.4 Hz), 6.85 (s, 1H), 4.00 (s, 3H), 3.94 (s, 3H), 3.82 (s, 2H), 3.66 (s, 4H), 3.48 (s, 4H)

Example 135

2-(2-(3,4-Dimethoxyphenyl)benzofuran-5-yl)-N,N-dimethylacetamide

Through similar procedure to the method disclosed in Example 59, 2-(2-(3,4-Dimethoxyphenyl)benzofuran-5-yl)-N,N-dimethylacetamide showing following physicochemical property was obtained Yield: 77%;
m.p.: 175° C.;
$^1$H NMR (CDCl$_3$): δ ppm 7.36-7.45 (m, 4H, Ar), 7.14 (d, 1H, J=8.4 Hz), 6.90 (d, 1H, J=8.4 Hz), 6.85 (s, 1H), 3.99 (s, 3H), 3.93 (s, 3H), 3.80 (s, 2H), 3.03 (s, 3H), 2.98 (s, 3H)

Example 136

2-(2-(3,4-Dimethoxyphenyl)benzofuran-5-yl)-1-(pyrrolidin-1-yl)ethanone

Through similar procedure to the method disclosed in Example 78, 2-(2-(3,4-Dimethoxyphenyl)benzofuran-5-yl)-1-(pyrrolidin-1-yl)ethanone showing following physicochemical property was obtained Yield: 77%;
m.p.: >200° C.;
$^1$H NMR (CDCl$_3$): δ ppm 7.36-7.45 (m, 4H, Ar), 7.14 (d, 1H, J=8.4 Hz), 6.90 (d, 1H, J=8.4 Hz), 6.85 (s, 1H), 3.74 (s, 2H), 3.43-3.53 (m, 4H), 1.81-1.96 (m, 4H)

Example 137

1-(4-Benzylpiperidin-1-yl)-2-(2-(3,4-dimethoxyphenyl)benzofuran-5-yl)ethanone Through similar procedure to the method disclosed in Example 78, 1-(4-Benzylpiperidin-1-yl)-2-(2-(3,4-dimethoxyphenyl)benzofuran-5-yl)ethanone showing following physicochemical property was obtained Yield: 77%;
m.p.: 115° C.;
$^1$H NMR (CDCl$_3$): δ ppm 7.36-7.45 (m, 4H, Ar), 7.14 (d, 1H, J=8.4 Hz), 6.90 (d, 1H, J=8.4 Hz), 6.85 (s, 1H), 4.57-4.72 (m, 1H), 3.99 (s, 3H), 3.94 (s, 3H), 3.83 (s, 2H), 3.80 (s, 2H), 2.83 (m, 1H), 2.42-2.60 (m, 4H), 2.00 (s, 1H), 1.60-1.73 (m, 2H)

Example 138

2-(2-(3,4-Dimethoxyphenyl)benzofuran-5-yl)-1-(4-methylpiperazin-1-yl)ethanone Through similar procedure to the method disclosed in Example 78, 2-(2-(3,4-Dimethoxyphenyl)benzofuran-5-yl)-1-(4-methylpiperazin-1-yl)ethanone showing following physicochemical property was obtained Yield: 77%;
m.p.: 130° C.;
$^1$H NMR (CDCl$_3$): δ ppm 7.36-7.45 (m, 4H, Ar), 7.14 (d, 1H, J=8.4 Hz), 6.90 (d, 1H, J=8.4 Hz), 6.85 (s, 1H), 3.68 (t, 2H), 3.50 (t, 2H), 2.36 (t, 2H), 2.19-2.24 (m, 5H),

Example 139

3-(2-(4-Hydroxy-3-methoxyphenyl)benzofuran-5-yl)-1-(piperidin-1-yl)propan-1-one Through similar procedure to the method disclosed in Example 78, 3-(2-(4-Hydroxy-3-methoxyphenyl)benzofuran-5-yl)-1-(piperidin-1-yl)propan-1-one showing following physicochemical property was obtained Yield: 77%;
m.p.: 197° C.;
$^1$H NMR (CDCl$_3$): δ ppm 7.38 (t, 4H, Ar), 7.10 (d, 1H, J=8.4 Hz), 6.90 (d, 1H, J=8.4 Hz), 6.81 (s, 1H), 6.04 (s, 1H), 4.11 (s, 1H), 3.56 (t, 2H, J=8.7 Hz), 3.33 (t, 2H, J=8.7 Hz), 3.05 (t, 2H, J=6.9 Hz), 2.66 (t, 2H, J=6.9 Hz), 1.52 (m, 6H),

Example 140

2-(2-(3,4-Dimethoxyphenyl)-3-(methylthio)benzofuran-5-yl)propanoic acid

Through similar procedure to the method disclosed in Example 70, 2-(2-(3,4-Dimethoxyphenyl)-3-(methylthio)benzofuran-5-yl)propanoic acid showing following physicochemical property was obtained Yield: 75%;
m.p.: >200° C.;
$^1$H NMR (CD$_3$OD): δ ppm 7.98 (d, 1H, J=1.8 Hz), 7.88 (dd, 1H, J=1.8, 8.4 Hz), 7.62 (d, 1H, J=1.8 Hz), 7.47 (d, 1H, J=8.4 Hz), 7.29 (dd, 1H, J=1.8, 8.4 Hz), 7.08 (d, 1H, J=8.4 Hz), 3.92 (s, 3H), 3.90 (s, 3H), 3.85 (q, 1H, J=6.9 Hz) 2.37 (s, 3H), 2.52 (d, 3H, J=6.9 Hz)

Example 141

N-[2-(3,4-Dimethoxy-phenyl)-benzofuran-5-yl]-propionamide

Through similar procedure to the method disclosed in Example 59, N-[2-(3,4-Dimethoxy-phenyl)-benzofuran-5-yl]-propionamide showing following physicochemical property was obtained Yield: 79%;
m.p: 187° C.;
$^1$H NMR (CDCl$_3$): δ ppm 7.88 (s, 1H), 7.42 (d, 2H, J=8.6 Hz), 7.35 (d, 1H, J=1.7 Hz), 7.20 (dd, 1H, J=8.6 Hz, J=1.8 Hz), 6.94 (d, 1H, J=8.4 Hz), 6.86 (s, 1H), 3.99 (s, 3H), 3.94 (s, 3H), 2.42 (m, 2H), 1.28 (t, 3H, J=7.5 Hz)

Example 142

N-[2-(3,4-Dimethoxy-phenyl)-benzofuran-5-yl]-butyramide

Through similar procedure to the method disclosed in Example 59, N-[2-(3,4-Dimethoxy-phenyl)-benzofuran-5-yl]-butyramide showing following physicochemical property was obtained Yield: 55%;
m.p: >200° C.;
$^1$H NMR (CDCl$_3$): δ ppm 7.89 (s, 1H), 7.42 (d, 2H, J=8.6 Hz), 7.36 (d, 1H, J=2.0 Hz), 7.20 (m, 1H), 6.94 (d, 1H, J=8.3 Hz), 6.87 (s, 1H), 3.99 (s, 3H), 3.94 (s, 3H), 2.37 (t, 2H, J=7.3 Hz), 1.80 (m, 2H), 1.04 (t, 3H, J=7.4 Hz)

Example 143

2-(3,4-dimethoxyphenyl)-N-propylbenzofuran-5-amine

Through similar procedure to the method disclosed in Example 59, 2-(3,4-dimethoxyphenyl)-N-propylbenzofuran-5-amine showing following physicochemical property was obtained Yield: 44%;
m.p: 88° C.;
$^1$H NMR (CDCl$_3$): δ ppm 7.39 (dd, 1H, J=8.2 Hz, J=1.8 Hz), 7.34 (d, 1H, J=2.0 Hz), 7.30 (d, 1H, J=8.8 Hz), 6.91 (d, 1H, J=8.4 Hz), 6.78 (s, 1H), 6.73 (d, 1H, J=2.4 Hz), 6.58 (dd, 1H, J=8.6 Hz, J=2.4 Hz), 3.98 (s, 3H), 3.92 (s, 3H), 3.11 (t, 2H, J=7.0 Hz), 1.69 (m, 2H), 1.03 (t, 3H, J=7.5 Hz)
MS (FAB) m/z 311 (M+H)

Example 144

Butyl-[2-(3,4-dimethoxy-phenyl)-benzofuran-5-yl]-amine

Through similar procedure to the method disclosed in Example 59, Butyl-[2-(3,4-dimethoxy-phenyl)-benzofuran-5-yl]-amine showing following physicochemical property was obtained Yield: 18%;
$^1$H NMR (CDCl$_3$): δ ppm 7.40 (dd, 1H, J=8.4 Hz, J=2.0 Hz), 7.35 (d, 1H, J=2.0 Hz), 7.30 (d, 1H, J=8.6 Hz), 6.92 (d, 1H, J=8.4 Hz), 6.79 (s, 1H), 6.73 (d, 1H, J=2.4 Hz), 6.59 (dd, 1H, J=8.8 Hz, J=2.4 Hz), 3.99 (s, 3H), 3.93 (s, 3H), 3.15 (t, 2H, J=7.0 Hz), 1.53 (m, 4H), 0.98 (t, 3H, J=7.3 Hz)

MS (FAB) m/z 325 (M+H)

Example 145

5-Allyloxy-2-(3,4-dimethoxy-phenyl)-benzofuran

Through similar procedure to the method disclosed in Example 70, 5-Allyloxy-2-(3,4-dimethoxy-phenyl)-benzofuran showing following physicochemical property was obtained
Yield: 21%;
m.p: 118° C.;
$^1$H NMR (CDCl$_3$): δ ppm 7.39 (m, 3H), 7.04 (d, 1H, J=2.6 Hz), 6.94 (d, 1H, J=8.3 Hz), 6.89 (dd, 1H, J=8.8 Hz, J=2.6 Hz), 6.85 (s, 1H), 6.11 (m, 1H), 5.43 (m, 1H), 5.30 (m, 1H), 4.57 (m, 1H), 3.99 (s, 3H), 3.93 (s, 3H)

Example 146

52-(3,4-Dimethoxy-phenyl)-5-propoxy-benzofuran

Through similar procedure to the method disclosed in Example 70, 2-(3,4-Dimethoxy-phenyl)-5-propoxy-benzofuran showing following physicochemical property was obtained
Yield: 4%;
m.p: 114° C.;
$^1$H NMR (CDCl$_3$): δ ppm. 7.88 (dd, 1H, J=8.4 Hz, J=2.0 Hz), 7.68 (d, 1H, J=2.0 Hz), 7.35 (m, 1H), 7.02 (d, 1H, J=8.6 Hz), 6.96 (d, 1H, J=8.6 Hz), 6.77 (m, 2H), 3.93 (m, 8H), 1.82 (m, 2H), 1.04 (t, 3H, J=7.3 Hz)

Experimental Example 1

In Vitro Activity Test 1-1. Inhibition Test of Beta Amyloid Aggregation

Synthetic beta amyloid 1-42 (BACHEM) was dissolved in DMSO in order to 250 μm solution and diluted with PBS into ¹⁄₁₀ on fluorescent black plate to induce aggregation. By comparing with inhibition activity of the tanshinone compounds prepared in Example 1 on beta amyloid aggregation, the test sample showing more than 50% inhibition activity at 10 μg/ml was chosen to use and added to react for 1 hour at room temperature. ThT (Thioflavin T) was diluted with 50 mM glycine buffer solution and the diluted solution was added to each well by 150 μl/well. The absorbance was determined by microplate reader (SAFIRE, TECAN) at 450 nm excitation wavelength/480 nm emission wavelength and the inhibition activity of the test sample on beta amyloid aggregation was transformed into IC$_{50}$.

As can be shown in FIG. 1, the compound 18b (Example 28) showed most potent inhibitory effect on the aggregation of beta amyloid.

1-2. Inhibition Test of Beta Amyloid Aggregation Lysis

Synthetic beta amyloid, Ab(1-42) [Bachem Cat. No. H1368; H-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-ILe-Ala-OH]) was dissolved in DMSO in order that it induces aggregation at the concentration of 25 microM for 1 week. The test group added with aggregated betaamyloid and test samples inhibiting the inhibition of aggregation and a control group added with only A were reacted together at room temperature for 1 hour on fluorescent black plate. ThT (Thioflavin T) was diluted with 50 mM glycine buffer solution to be 5 microliter and the diluted solutions were added to each well by 150 μg/well. The fluorescence intensity of each group was determined by microplate reader (SAFIRE, TECAN) at 450 nm excitation wavelength/480 nm emission wavelength after shaking together for 10 seconds.

1-3. Inhibition Test of Beta Amyloid Toxicity

To determine the inhibitory activity of the compounds prepared in Examples on beta-amyloid toxicity, following test was performed according to the procedure disclosed in the literature (Gillardon, F. et al., *Brain Research*, 706 (1), pp. 169-172, 1996).

HT22 mouse neuronal cell line was incubated in DMEM (Dulbecco's Modified Eagle's Medium, Gibco-BRL) medium supplemented with 10% FBS (Fetal Bovine Serum, Hyclone) and 1% penicillin/streptomycin (Sigma Co.). Prior to test, HT22 cell was incubated on 96 well plates with a density of 5×10$^3$ cell/well and further incubated in serum free DMEM medium for 1 hour before the treatment of test sample. Various concentration of compounds prepared in Examples used as a test sample was added thereto and incubated for 1 hour. Aggregated beta amyloid 25-35 (US peptide) was treated thereto to the concentration of 25 μm and incubated for 18 hours to induce cell necrosis. 5 mg/ml of MIT (3-(4,5-dimethyl-2-thiazolyl)-2,5-diphenyl-2H-tetrazolium bromide) solution was added each well with 15 μl/well and the well was incubated for 4 hours. Dissolving buffer solution (10% SDS, 50% dimethyl formamide, pH 4.7) was added to each well with 100 μl/well and reacted for overnight. 18 hours after the reaction, the absorbance of solution was determined by microplate reader (SAFIRE, TECAN) at 570 nm/630 nm wavelength (Gillardon, F. et al., *Brain Research*, 706 (1) pp 169-172, 1996).

1-4. Determination of Cytotoxicity

To determine the toxicity of test sample, HT22 cell was incubated in accordance with similar method disclosed in 1-3 and various concentration of the test sample prepared in Examples 1-89 was added to the cell to incubate for 18 hours. MTT solution and Dissolving buffer solution was added to cell serially and the absorbance was determined by microplate reader (SAFIRE, TECAN) at 570 nm.

As can be shown in FIG. 1, the compounds 15a, 15b, 16 and 18b showed potent inhibition effect on the beta-amyloid aggregation and beta-amyloid toxicity, particularly, compound 18b (Example 28) among them showed most potent inhibitory effect on the aggregation of beta amyloid and potent solubilizing activity of beta-amyloid.

Experimental Example 2

In Vivo Activity Test

Experimental Design

For passive avoidance test, male ICR mouse weighing 25 g purchased from Samtaco Co. was bred with five mice per cage and the cage was kept with following condition maintaining the temperature of 22±2° C. and the relative humidity of 50±5% under the regularly controlled light/dark condition with an interval of 12 hours.

Synthetic beta amyloid 1-42 (BACHEM) was dissolved in DMSO in order to be 250 μm solution and diluted with PBS to 10 nM and aggregated at 37° C. for four days (Passive Avoidance test) or six days (Y maze test).

Aggregated beta amyloid 1-42 was administered into the mice according to the procedure disclosed in the literature (Lausen & Belknap, *J. Pharmacol. Methods*, 16 pp 355-357, 1986).

50 μl of aggregated beta amyloid 1-42 was administrated into the 2.4 mm depth of bregma region with 50 μl of Hamilton micro-syringe equipped with 26-gauge needle. The behavior tests were divided into Y maze test and PA (passive avoidance) test after the beta amyloid administration. Y maze test was performed 2 days after the administration and PA test was 3 days after the administration. Each test was done with more than 10 mice.

At the end of the experiment, the brain of animals was delivered and kept in 10% formalin solution to staining.

Drug Treatment

After the administration of beta amyloid, the test compounds, i.e., 15a, 15b, 16 and 18b prepared in Examples were administrated into the mice at the interval of once a day in case of Y maze test and the test samples were continuously administrated for three days in case of passive avoidance test. The concentration test samples in orally administration group was set to 100 mg/kg treatment group and especially, the various concentrations of compound 18b, 50 mg/kg, 100 mg/kg, and 200 mg/kg were adopted to determine its drug dose-dependency. In case of Y maze test, the feed was administered using by pellet feed for 8 days and one among those pellet was designed to containing 3 mg of drug.

Behavior Procedure

AD Acute Model Experiment—Y Maze Test

To test the cognitive capacity effects of the four compounds, i.e., compounds 15a, 15b, 16, and 18b, selected from Experimental Example 1, following Y maze test was performed according to the procedure disclosed in the literature (*Psychopharmacology*, 94, pp. 491-95, 1998).

The Y-maze test was performed two days after the administration of beta-amyloid. Y-maze box was made of black acrylic and was composed of three arms (length: 40 cm, Height: 10 cm, Width 5 cm) having identical angle each other. The mice were positioned at the center of the maze and let to move freely within the maze for eight minutes. Thereafter, the entering order of the mice into the pathway was observed and the entering time was determined when four limbs of the mice were entered within the pathway. To determine the spatial memory, the percentage of spontaneous alteration behavior was calculated by applying the measured alteration frequency to following empirical formula 1 and the frequency of actual alteration behavior was assigned once at the time that the mice had entered the three pathways continuously.

Spontaneous alteration(%)=[actual alteration/total arm entries−2]×100   [Math Formula 1]

Figure 2:
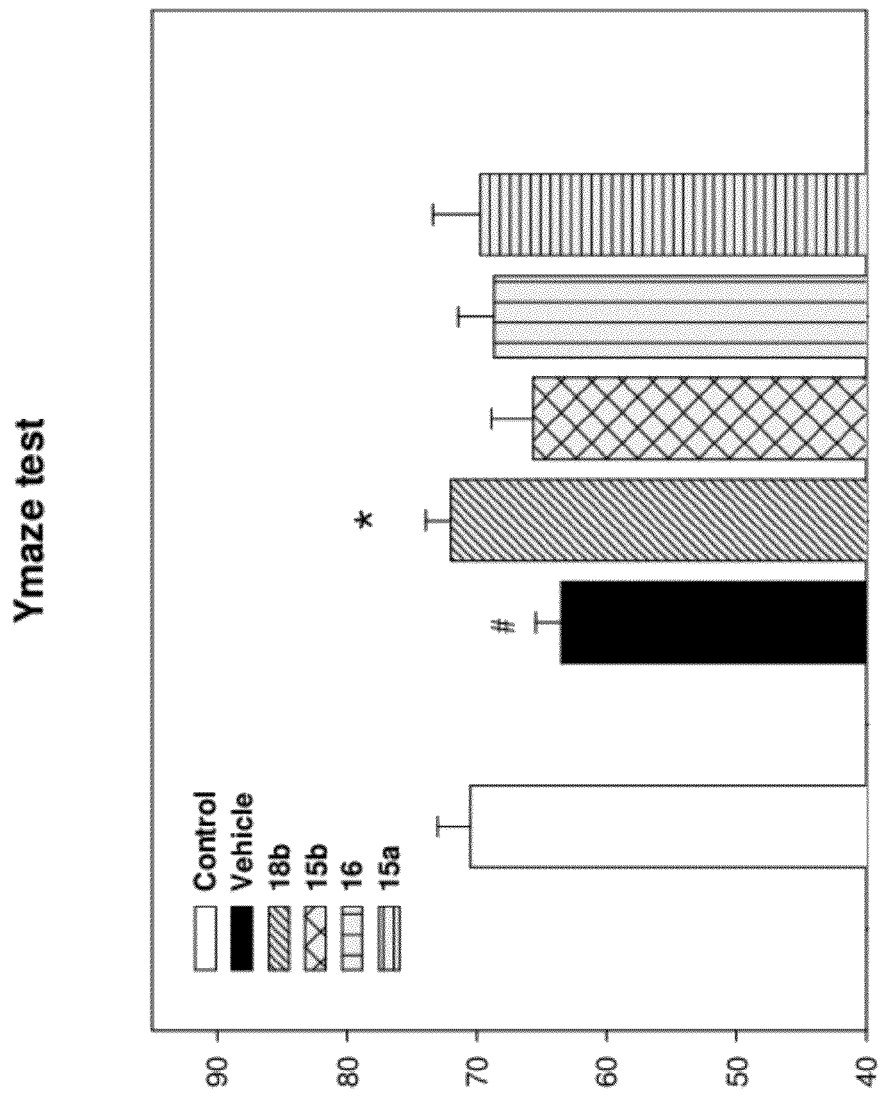
FIG. 2 shows the result of Y maze test using animal model treated with beta-amyloid and inventive compounds.

FIG. 2 indicates the result of the Y maze test with the four compounds selected from Experimental Example 1 (See FIG. 2).

Figure 3:
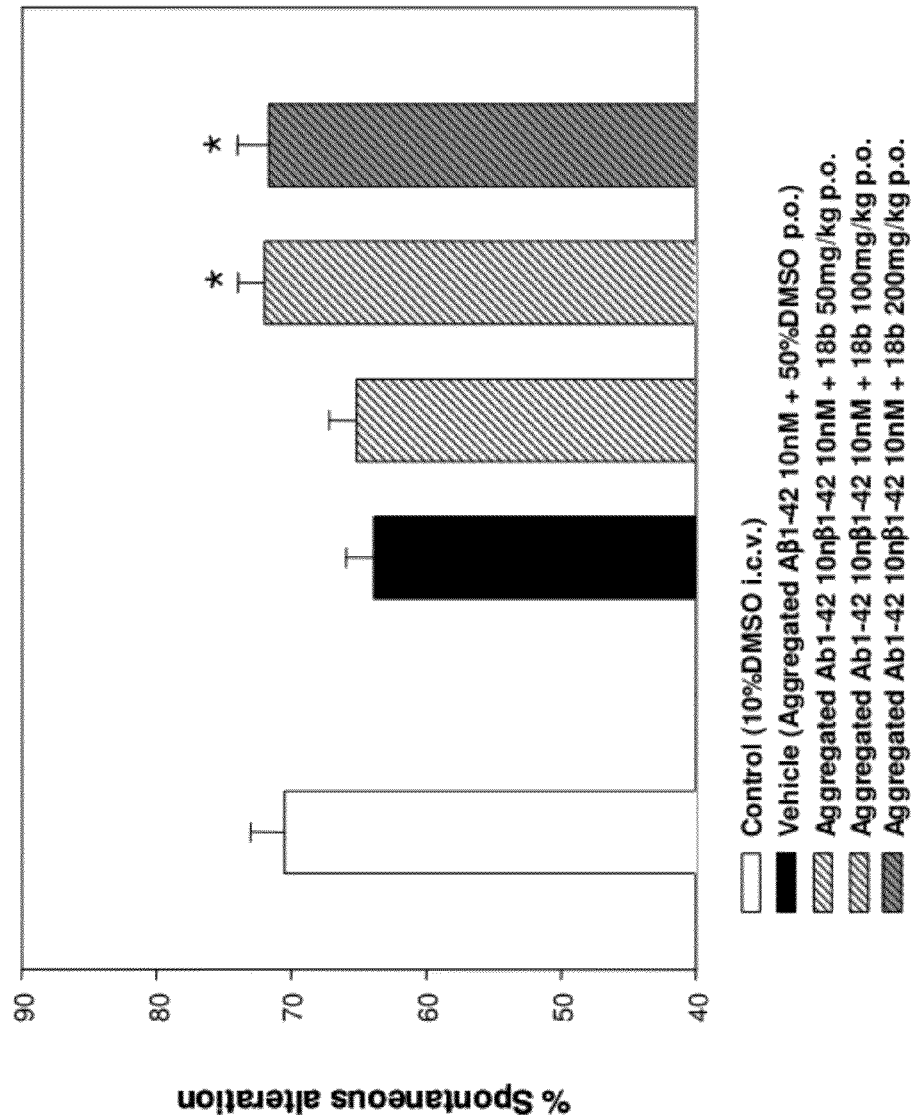
FIG. 3 shows the result of Y maze test using animal model treated with various concentrations of inventive compound (18b) in a dose dependent manner.

As can be seen in FIG. 2, the compound 18b shows potent recovering effect on memory learning capacity damaged by beta-amyloid in a dose dependent manner. Also FIG. 3 shows that the recovering effect of the compound was increased in a dose-dependent manner. The treatment group with more than 100 mg/kg showed the most excellent effect on the memory learning capacity (See FIG. 3).

2-2-2. AD Acute Model Experiment—Passive Avoidance Test

To test the cognitive capacity effects of the four compounds, i.e., compounds 15a, 15b, 16, and 18b, selected from Experimental Example 1, following Passive Avoidance test was performed according to the procedure disclosed in the literature (*J. Neurochem.*, 71, pp. 875-878, 1998).

Three days after the beta-amylaid administration, the passive avoidance test was performed by determining the time until every mouse entered into the dark compartment from the light compartment (step-through latency). The passive avoidance box was divided into two compartments, i.e., one is white chamber and another is dark chamber equipped with a grid floor providing an inescapable shock.

During the first acquisition trial, each mouse was placed in the lighted compartment; as soon as they entered the dark compartment, the door was closed, and they received an electric shock through the grid floor (0.6 Ma, 3 s). Thereafter, the mice were transferred to their home cage. 24 hours after the training trial, the mice were again placed in the lighted compartment and the time until they re-entered the dark compartment was measured (step-through latency). At this trial, the cut off latency was set to 300 seconds.

Figure 4:
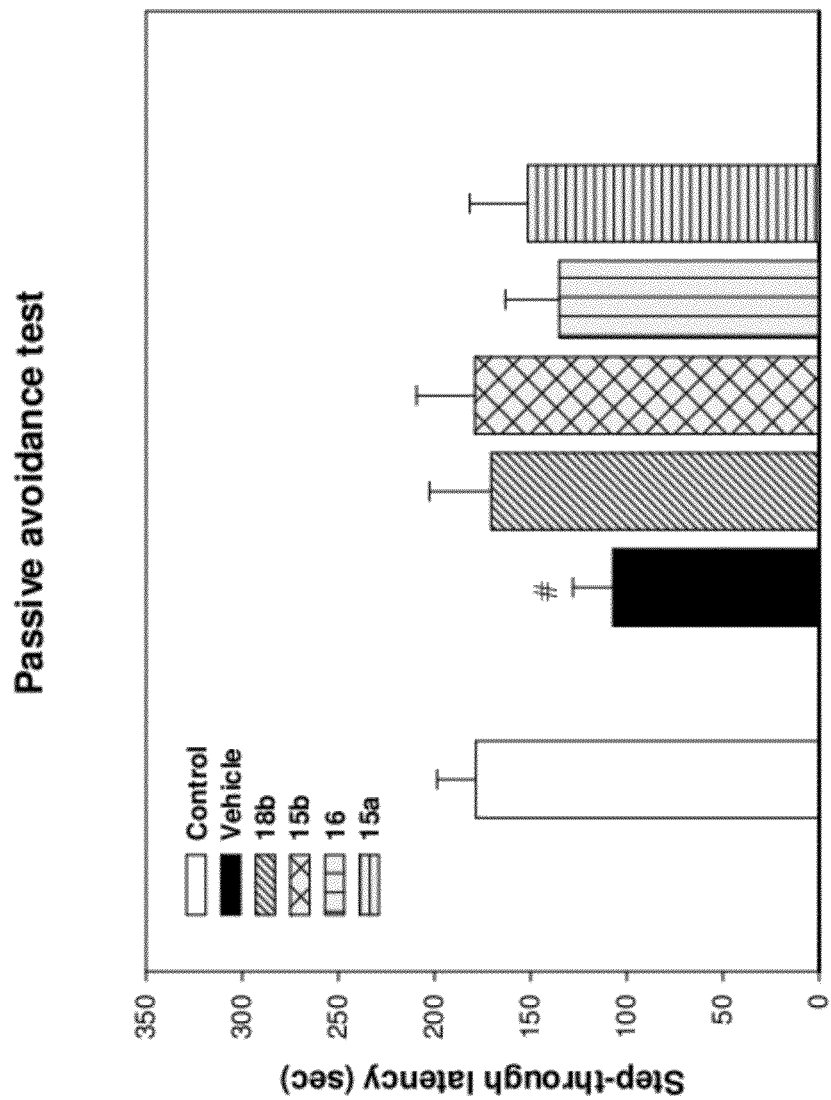
FIG. 4 represents the result of passive avoidance test using animal model treated with beta-amyloid and inventive compounds.
Figure 5:
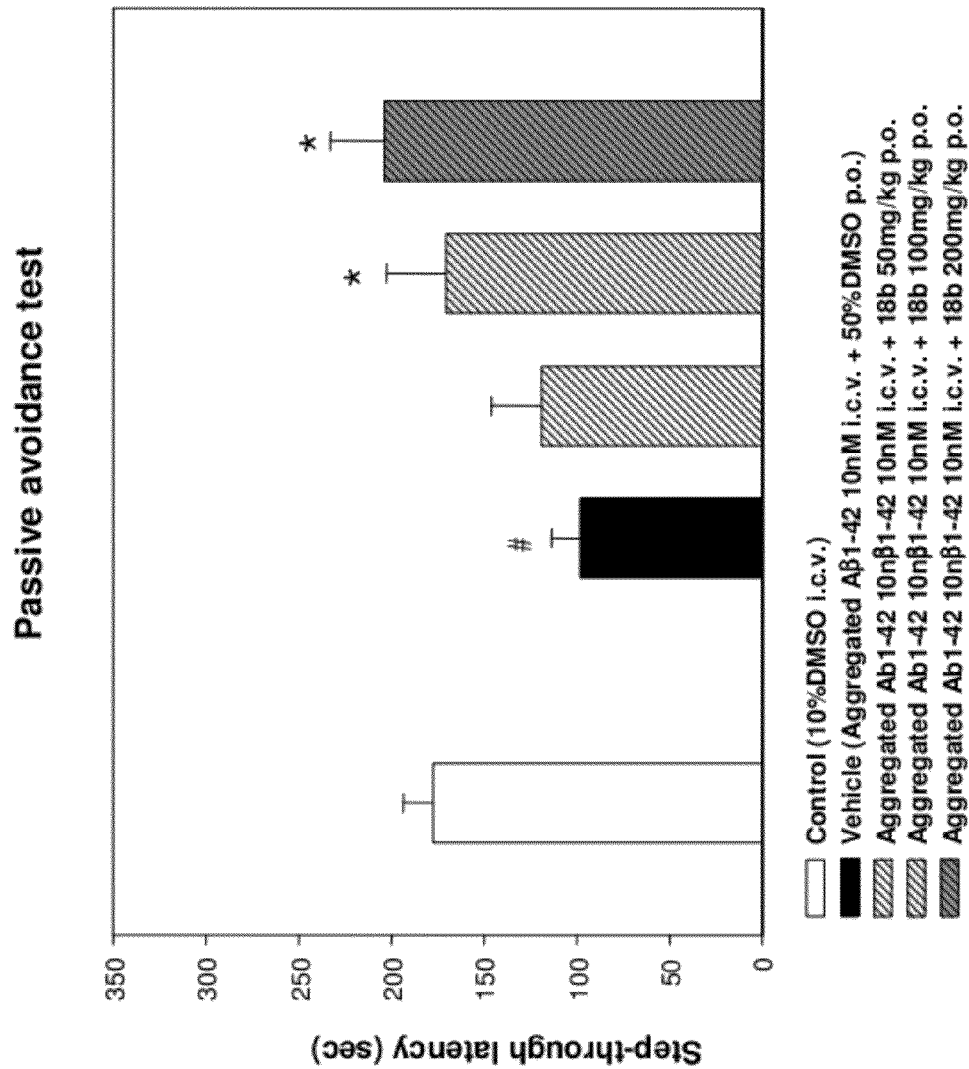
FIG. 5 represents the result of passive avoidance test using animal model treated with various concentrations of inventive compound (18b) in a dose dependent manner.

At the result of the above-describe test, the compound 18b exhibited potent recovering effect on memory learning damaged by beta-amyloid (See FIG. 4). Also FIG. 3 shows that the recovering effect of the compound was increased in a dose-dependent manner. The treatment group with more than 100 mg/kg showed the most excellent effect on the memory learning capacity (See FIG. 5).

Water Maze Test

To test the cognitive capacity effects of two compounds, i.e., compounds 15a and 18b selected from Experimental Examples, following water maze test was performed according to the procedure disclosed in the literature (*J. Neurosci. Methods.*, 11, pp. 47-60, 1984).

The water maze test was performed with using round aquarium. The temperature of water in the aquarium was maintained at 23° C. and the height of the water was arranged to be 1 cm higher than the level of platform. The platform was placed in the middle of one among 4 arbitrary quadrants in the aquarium and skim milk powder was poured into the water in order that the mouse could not show the platform. The spatial evidence for searching platform position was given to the mice at the wall surfaces surrounding the aquarium and the test was performed.

The test was performed continuously for 5 days four times a day and the interval of each trial was set to 30 seconds. During each trial, the mice was let to start randomly from four starting points and the time (latency) until they found the hidden platform for 60 seconds was measured. Noldus program (Etho vision software) was used as a tracking system.

Figure 6:
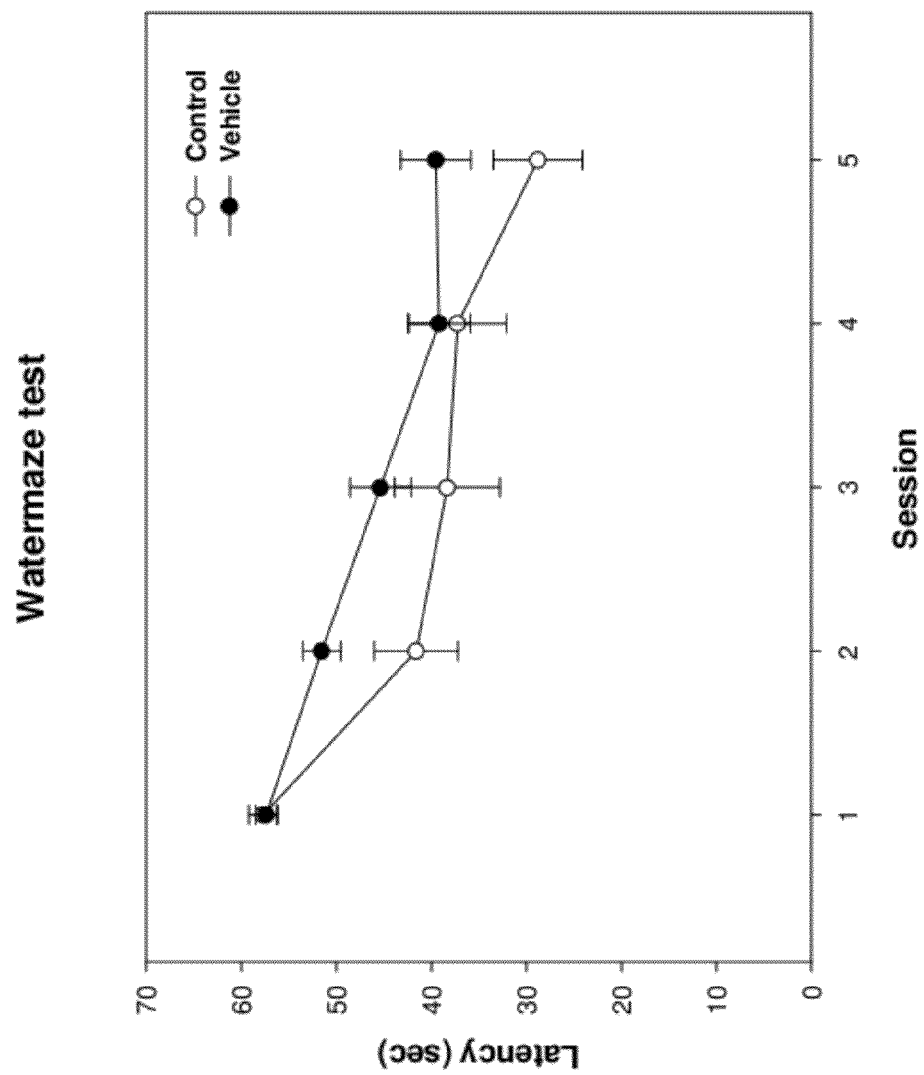
FIG. 6 represents the result of water maze test to determine the memory learning capacity in the mice where beta-amyloid was injected into a ventricle of their brains.

As can be seen in FIG. 6, it has confirmed that the memory learning capacity in the mice where beta-amyloid was injected into a ventricle of their brains was decreased (See FIG. 6).

Figure 7:
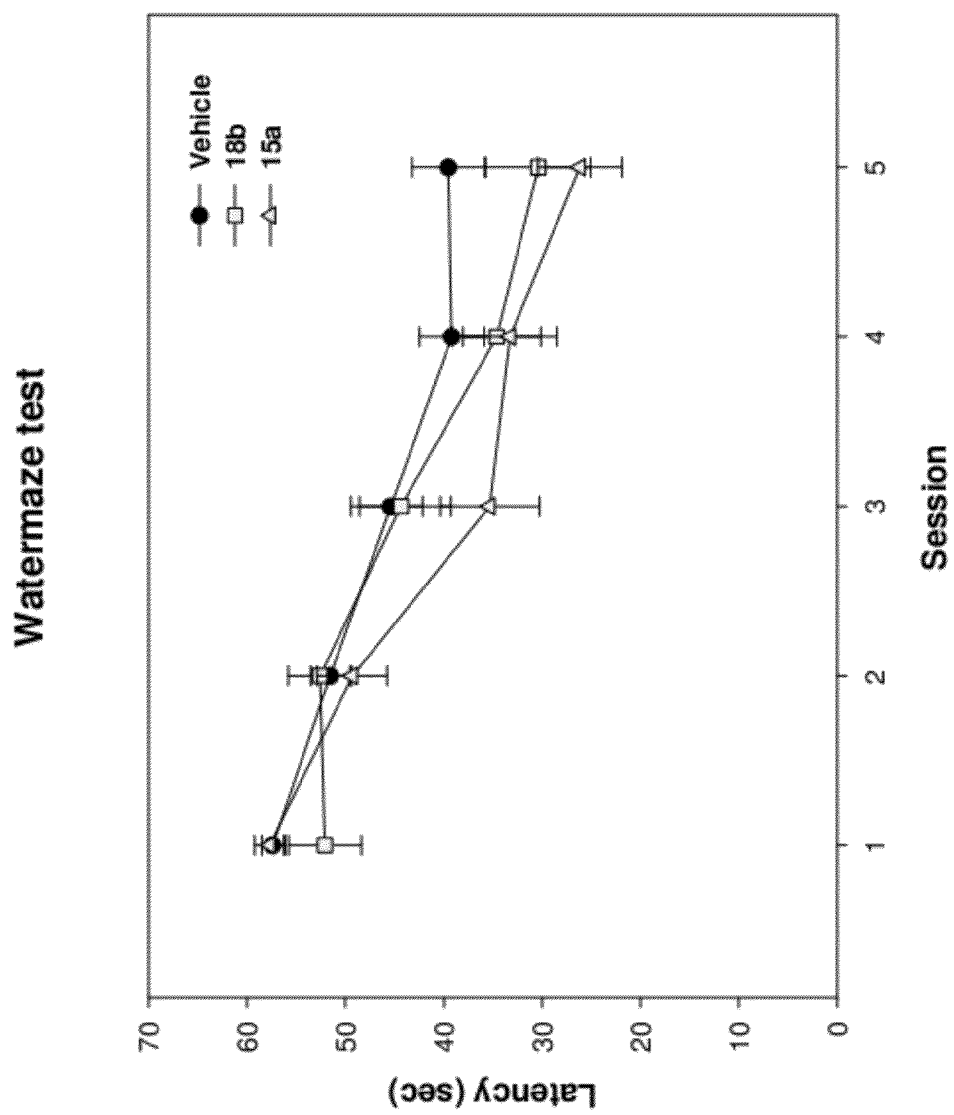
FIG. 7 presents the result of water maze test to determine the memory learning capacity in the mice treated with beta-amyloid and inventive compounds.

As can be seen in FIG. 7, it showed the result of the memory learning capacity in the mice treated with the inventive compounds 15a and 18b (See FIG. 7).

It has been confirmed that the inventive compounds recovered the decreased memory learning capacity in vivo in the mice treated beta-amyloid, of which result was consistent with the results of inhibition test of beta-amyloid aggregation and beta-amyloid toxicity test in vitro.

2-3-4 Cognitive Capacity Test

To test the cognitive capacity effects of four compounds, i.e., compounds 15a, 15b, 16 and 18b selected from Experimental Examples, following cognitive capacity test was performed according to the procedure disclosed in the literature (*Behav. Brain Res.*, 31, pp. 47-59. 1988)

The cognitive capacity test was performed by using an open field box consisting of black acrylic 50×50×30(height)

and the identical two objects which showed similar preference between each other were placed at 5 cm far away from the walls in a opposite direction.

The mice were allowed to explore the box for 3 minutes three times before testing (adaptive training). During training, the exploring time to find two objects placed in the box was determined for 3 minutes. In testing phase after 24 hours, one of the two objects was changed to new object and then the exploration time was measured again for 3 minutes in the box. Exploration behavior was calculated by following Math formula 2 and defined as follow: touching the object or sniffing it with putting their heads at a distance=2 cm to the objects.

$$\text{Preference index} = \text{exploration time for new object} / \text{exploration time for total object} \quad [\text{Math Formula 2}]$$

Figure 8:
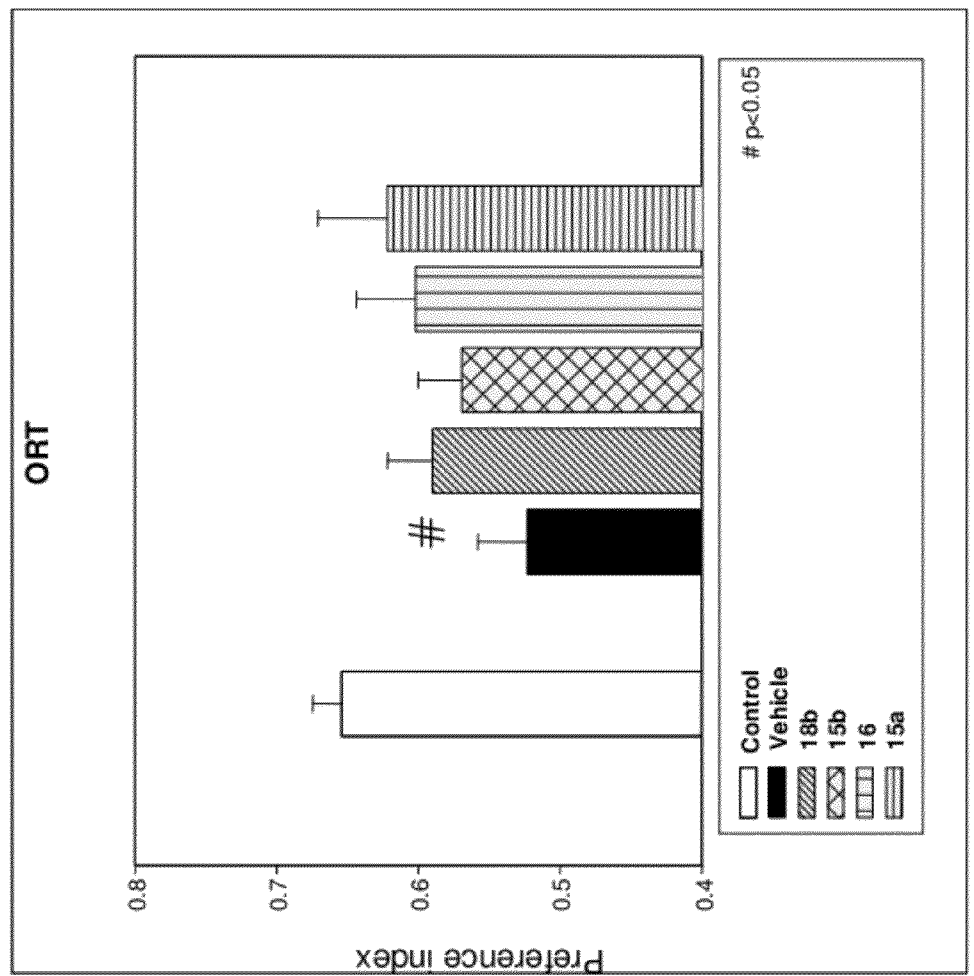
FIG. 8 depicts the result of cognitive capacity test memory to determine the recovering activity of learning study using animal model treated with beta-amyloid and inventive compounds.

As the result of the above test, it has confirmed that the group treated with the inventive compounds increased memory-learning capacity resulting in increased preference index while the group treated with beta amyloid could not concentrate on either object or could not be curious on new object. (See FIG. 8).

2-4. Immunochemistry Staining of AD Acute Model Mouse Recovering Cognitive Capacity 2-4-1. Brain Delivery and Pretreatment Before Staining At the end of behavior test, the mouse brain was delivered, kept in 10% formalin solution for 24 hours and transferred to 30% sucrose solution. After fixing the brain, the brain was performed to coronal section with a width of 40 micrometer using by cryostat. The sliced brain was performed to staining with cresyl violet to confirm the injury of brain neuronal cell, with ChAT to confirm the injury of cholinergic neuron and with GFAP to confirm the activation of astrocytes.

2-4-2. Cresyl Violet Staining

After the tissue was placed on gelatin-coated slide to stain with Cresyl violet, the tissue was performed to dehydration using ethanol. The tissue was incubated for about 3 minutes and dipped into 0.5% Cresyl Violet solution for 30 mins. After the solution was performed to re-hydration with ethanol, the slice was dipped into xylene for 3 minutes. The dried tissue was fixed with Canada balsam mounting medium.

2-4-3. Immunohistochemistry

In the washing process between all the antibody incubation, PBST was used to wash the tissues. To reduce the activity of endogenous peroxidase enzyme, the tissue was pre-treated with 0.5% $H_2O_2$ and then treated with 5% FBS at room temperature for 1 hour to remove non-specific binding. The tissue was incubated at 4° C. for overnight using by mouse anti-GFAP (1:200) monoclonal antibody and goat-anti-ChAT (1:200) polyclonal antibody. A horse radish peroxidase-conjugated anti-mouse IgG and anti-goat IgG secondary antibody (1:600) were incubated at room temperature for 1 hour and detected by DAB kit after the incubation.

To observe the neuronal injury and recovery, NeuN staining was performed, and GFAP staining was performed to observe the activation of astrocytes. ChAT staining was performed to observe to observe the injury and recovery of cholinergic neuron and the results were shown in FIGS. 9 to 11.

Figure 9:
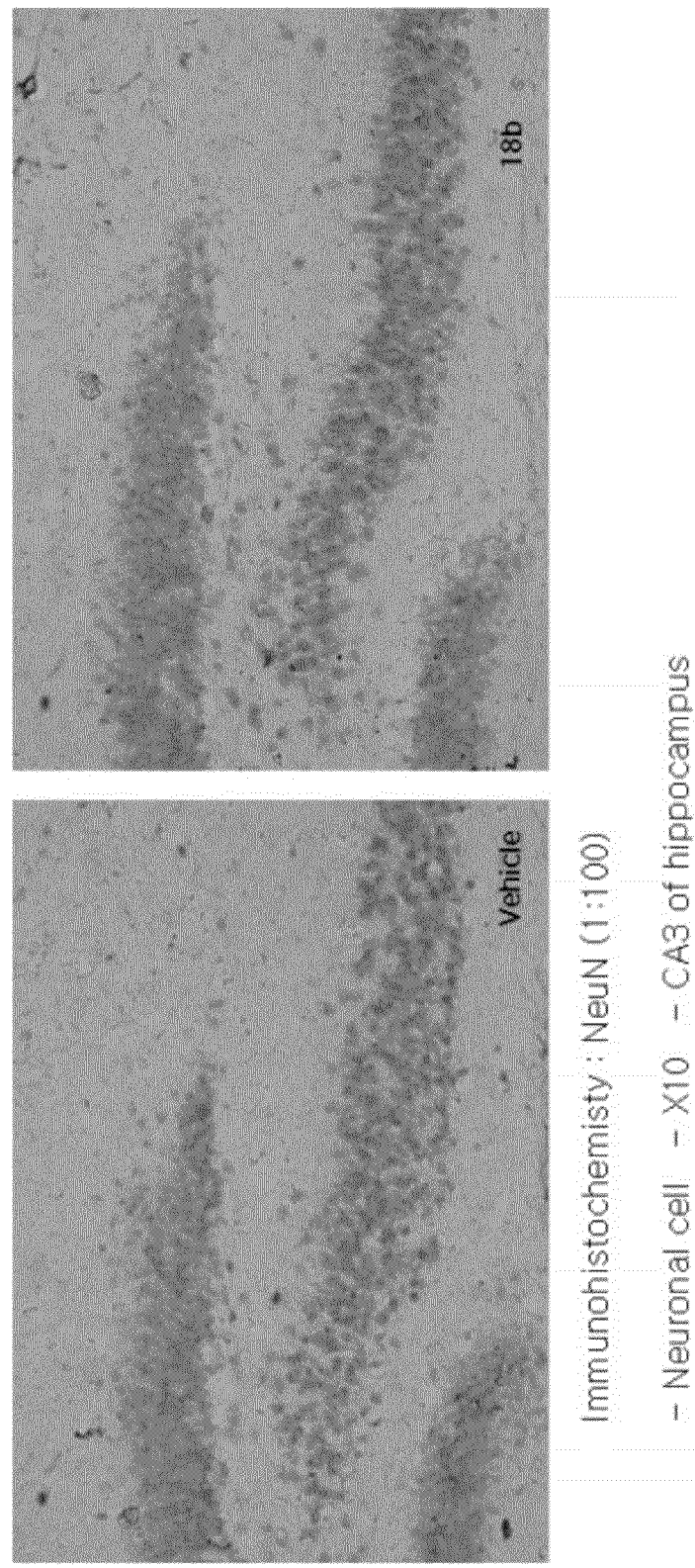
FIG. 9 depicts a neuron staining result of animal model having injured learning capacity caused by beta-amyloid treatment.

As can be shown in FIG. 9, it has been confirmed that the density of neuronal cell at CA region in Hippocampus was increased in case that the memory learning capacity was recovered by treatment with inventive compounds in learning memory-injured mouse model caused by beta-amyloid treatment.

Figure 10:
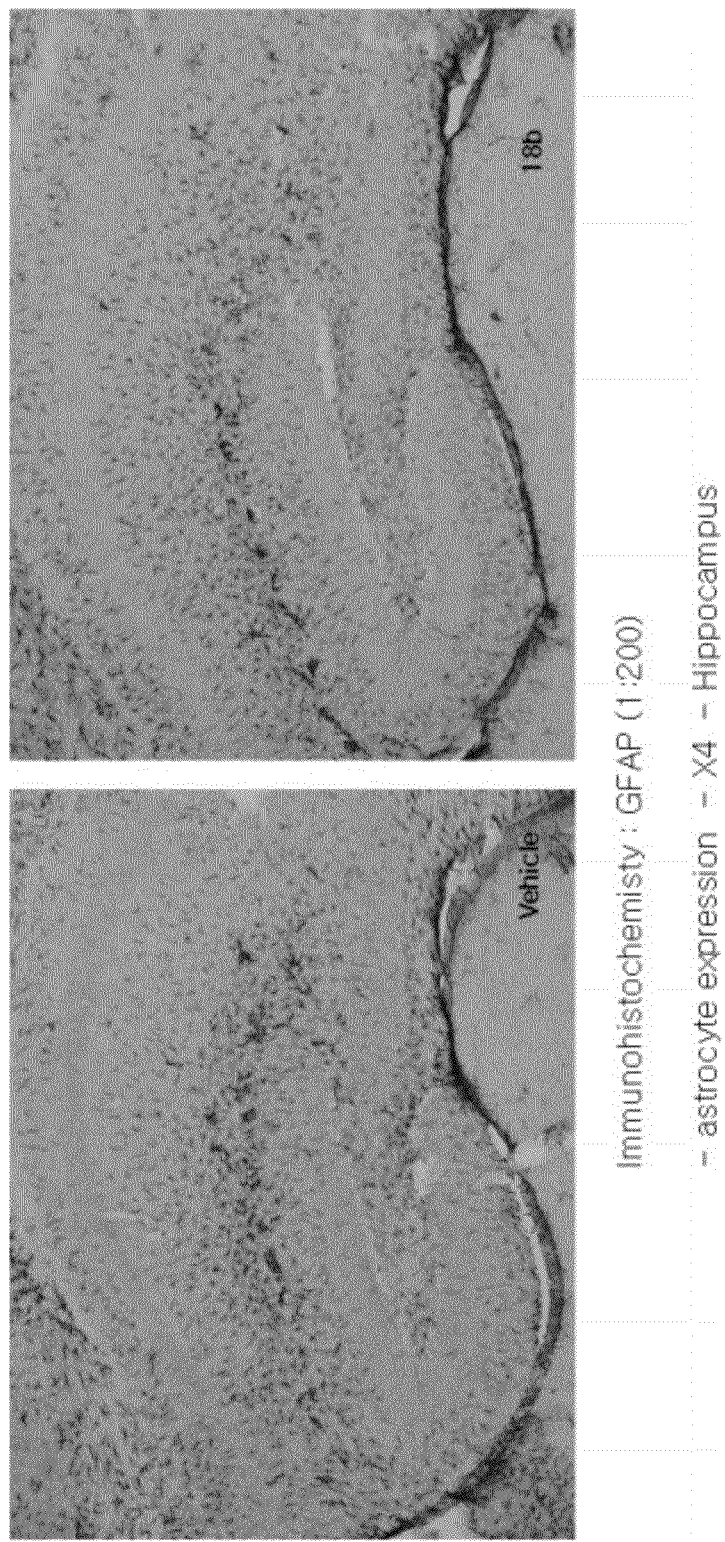
FIG. 10 depicts GFAP staining result of animal model having injured learning capacity caused by beta-amyloid treatment.
Figure 11:
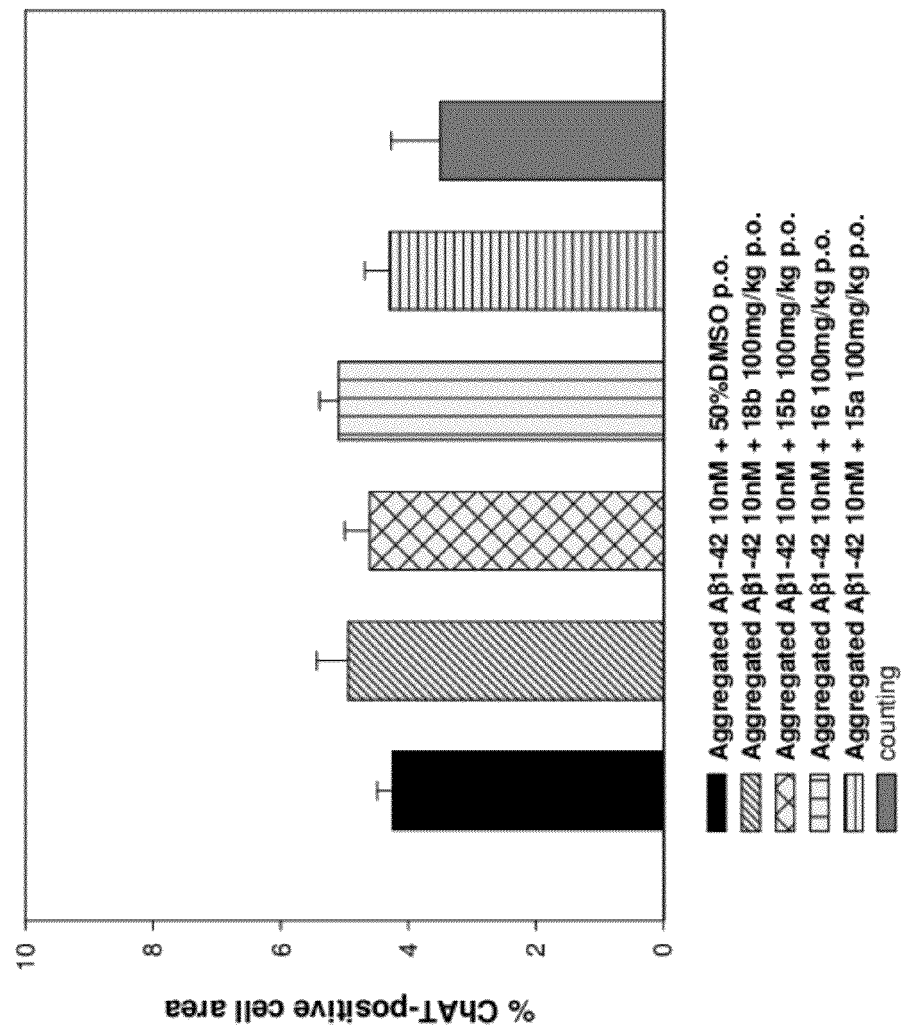
FIG. 11 depicts chAT staining result of animal model having injured learning capacity caused by beta-amyloid treatment.

FIG. 10 showed that the group treated with the inventive compounds reduced the activation of astrocytes and the memory learning recovered group increased the area of cholinergic neuron as shown in FIG. 11.

Experimental Example 3

In Vivo Physiological Activity 3-1. Experimental Design 13 months old dementia model male mice expressing APPswe was used in the experiment and the mice was divided into two groups, i.e., control group consisting of 2 mice and test groups consisting of 4 mice. Each mouse had been fed with the feed mixed with 3 mg of compound 11b everyday for 4 months.

3-2. Behavior Procedure 3-2-1. Y Maze Test

To test the cognitive capacity effects of the compound 11b chosen from the result of Experimental Example 1, following Y maze test was performed according to the procedure disclosed in the literature (*Psychopharmacology*, 94, pp 491-95, 1998).

From two days after the administration of beta-amyloid, the Y-maze test was performed. Y-maze box was made of black acrylic and composed of three arms (length: 40 cm, Height: 10 cm, Width 5 cm) having identical angle each other. The mice were positioned at the center of the maze and let to move freely in the maze for eight minutes. Thereafter, the entering order of the mice into the pathway was observed and the entering time was determined when four limbs was entered within the pathway. To determine the spatial memory, the percentage of spontaneous alteration behavior was calculated by applying measured alteration frequency to following math formula 1 and the frequency of actual alteration behavior was assigned once at the time that the mice had entered the three pathways continuously.

Figure 12:
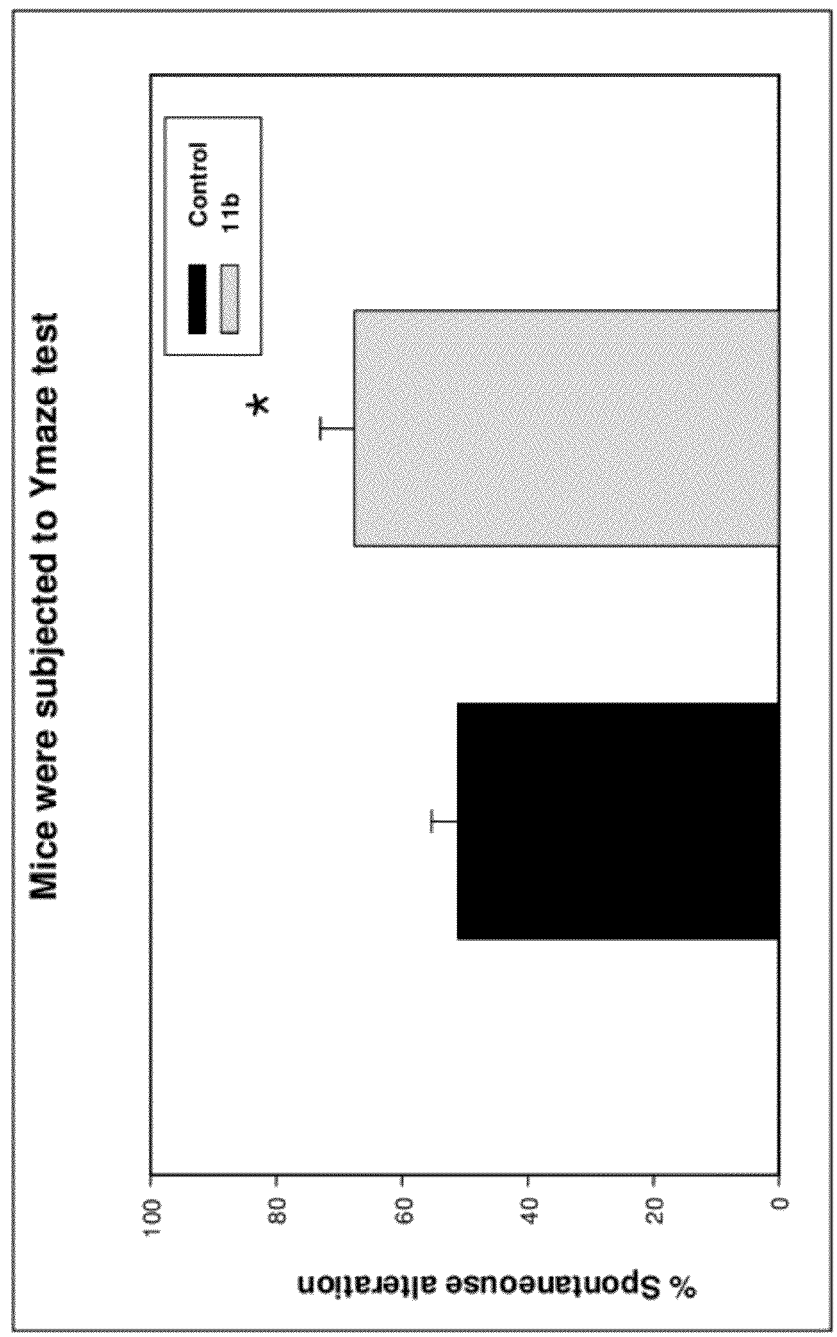
FIG. 12 presents the determined result of Y maze test of Experimental Example 3-2-1.

As can be seen in FIG. 12, the transgenic mice treated with compound 11b showed more increased curiosity about new object than control group (See FIG. 12).

3-2-2. Inhibitory Activity of Beta Amyloid Plaque Formation (a). Brain Delivery Using RIPA (Radio Immuno Precipitation Assay) Buffer Solution At the end of behavior test, the brain of mouse was delivered and the left hemisphere was frozen to be used as a cryo-section material. The remaining right hemisphere was used to measure the formation of beta-amyloid according to the procedure disclosed in the literature (*J. Neurosci*, 21 (12), pp 4183-4187, 2001).

For obtaining RIPA buffer soluble faction, the half brain of a mouse was macerated with ultrasonic waves (2×25 struck, output 20%) in 1 ml of RIPA buffer containing 150 mg/ml protease inhibitor cocktail and the tissues were centrifuged at 20.000 g for 5 minutes.

(b). ELISA Analysis

The amount of beta-amyloid in the brains of mice was determined by Aβ-specific ELISA method according to the manual provided from Biosource Co and ELISA kit (KHB 3482, Biosource Co.) was used in the experiment. Ab(1-40 & 42) provided as standard peptides was dissolved in given buffer solution (55 mM sodium bicarbonate. pH 9.0) and diluted to several concentrations ranging from 0 to 1000 pg/ml to obtain calibration curve. 25 g or 50 g of the delivered brain from the mice were diluted to 100 µl with dilution buffer and the diluted brains were added to ELISA strip. After incubation for 2 hours, each well was washed 4 times with wash buffer and detecting antibody was added to each well to incubate for 2 hours. After the incubation, all the wells were washed 4 times again and the secondary antibody formed by HRP polymer was added thereto to incubate for 2 hours. The incubated wells were washed five times and stabilized chromogen was added thereto to induce color reaction. After 30 minutes, stop solution was added to each well to stop the reaction. The level of color reaction was determined at 450 nm using by spectrophotometer and the absolute amount of beta-amyloid in the samples was transformed by comparing with standard value. The brain of the mice treated with the compound 18b for 4 months was delivered and the amount of beta-amyloid in supernatant obtained from the dissolved brain tissue was determined according to ELISA method.

Figure 13:
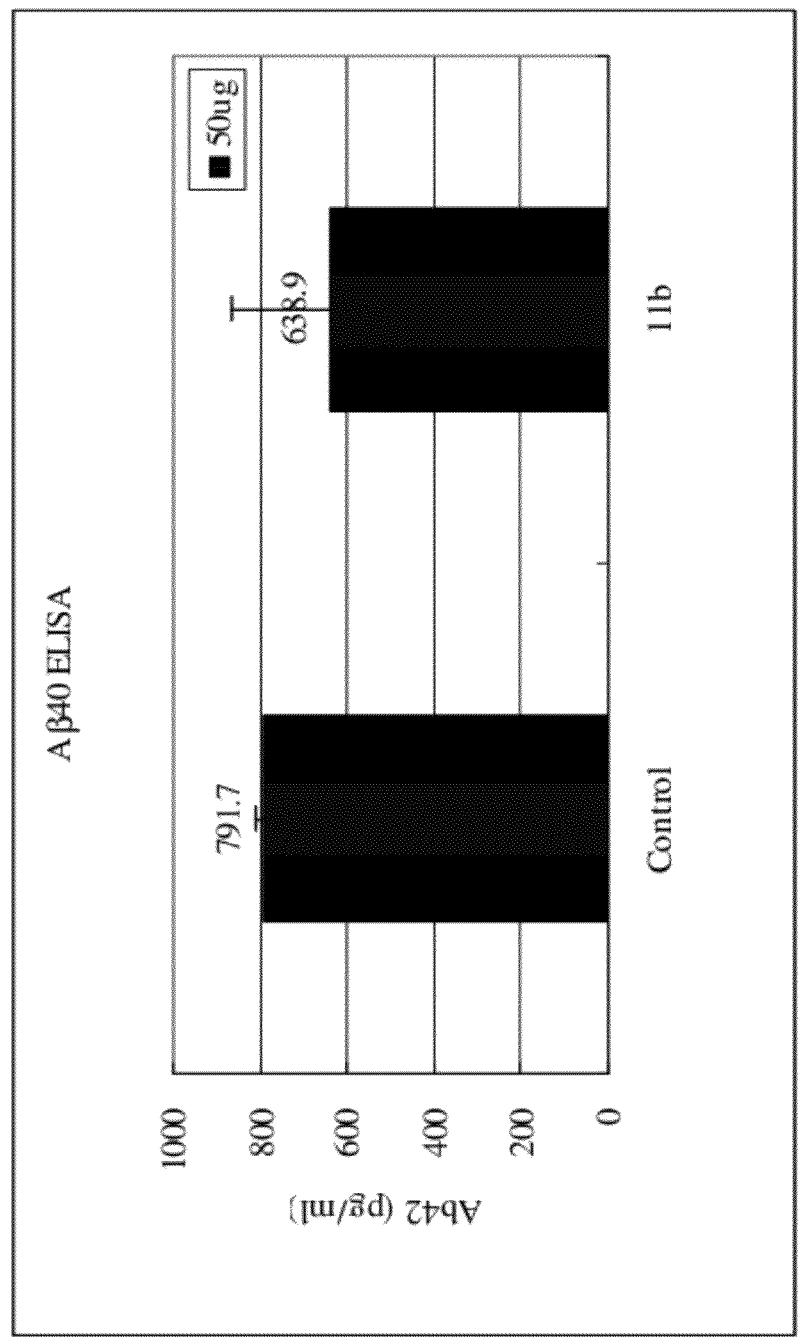
FIG. 13 presents the determined result of Aβ-40 ELISA test of Experimental Example 3-2-2.

At the result, there showed no difference in the change of the amount of A 42 and the amount of A 40 was slightly reduced through A 40 ELISA test, which showed no significance statistically (See FIG. 13).

(c). Brain Sections Staining Using Low Temperature Maintaining Apparatus.

Before staining, the left hemisphere of delivered brain was fixed in 10% formalin solution for overnight and transferred to 20% sucrose solution for 2 days to remove remaining water of the tissue. Using by low-temperature maintaining apparatus, the tissue was cut to a thickness of 40 μm with coronal and stored in store solution.

(d). Congo Red Staining Method.

The six tissue sections per mouse were placed on the slide glass and then stained with 0.2% alkali Congo-Red solution. Thereafter, the stained tissues were dehydrated with 100% ethanol and treated with xylene to remove the dehydrating agent. Then the tissues were covered with cover glass by using balsam in order not to forming air bubble. The existence of a plaque in the tissues was observed through optical microscope connecting with digital camera and the calculated number, size, and area of the plaque in the brain tissue were shown in FIG. 14.

Figure 14:
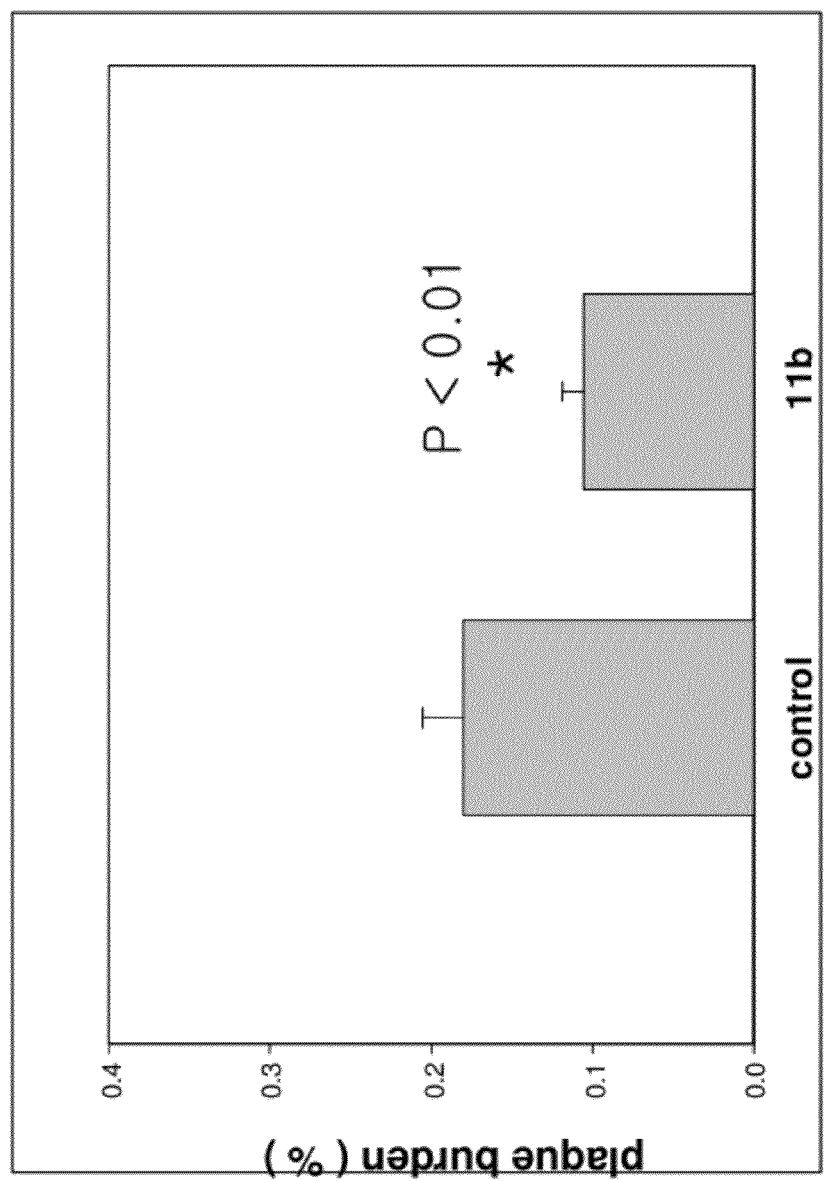
FIG. 14 presents transformed percentage (%) of area of beta-amyloid aggregation in transgenic mice treated with inventive compound.

As shown in the FIG. 14, the numbers, size, and area of plaque in transgenic mice treated with the compound 18b were significantly reduced (See FIG. 14).

Figure 15:
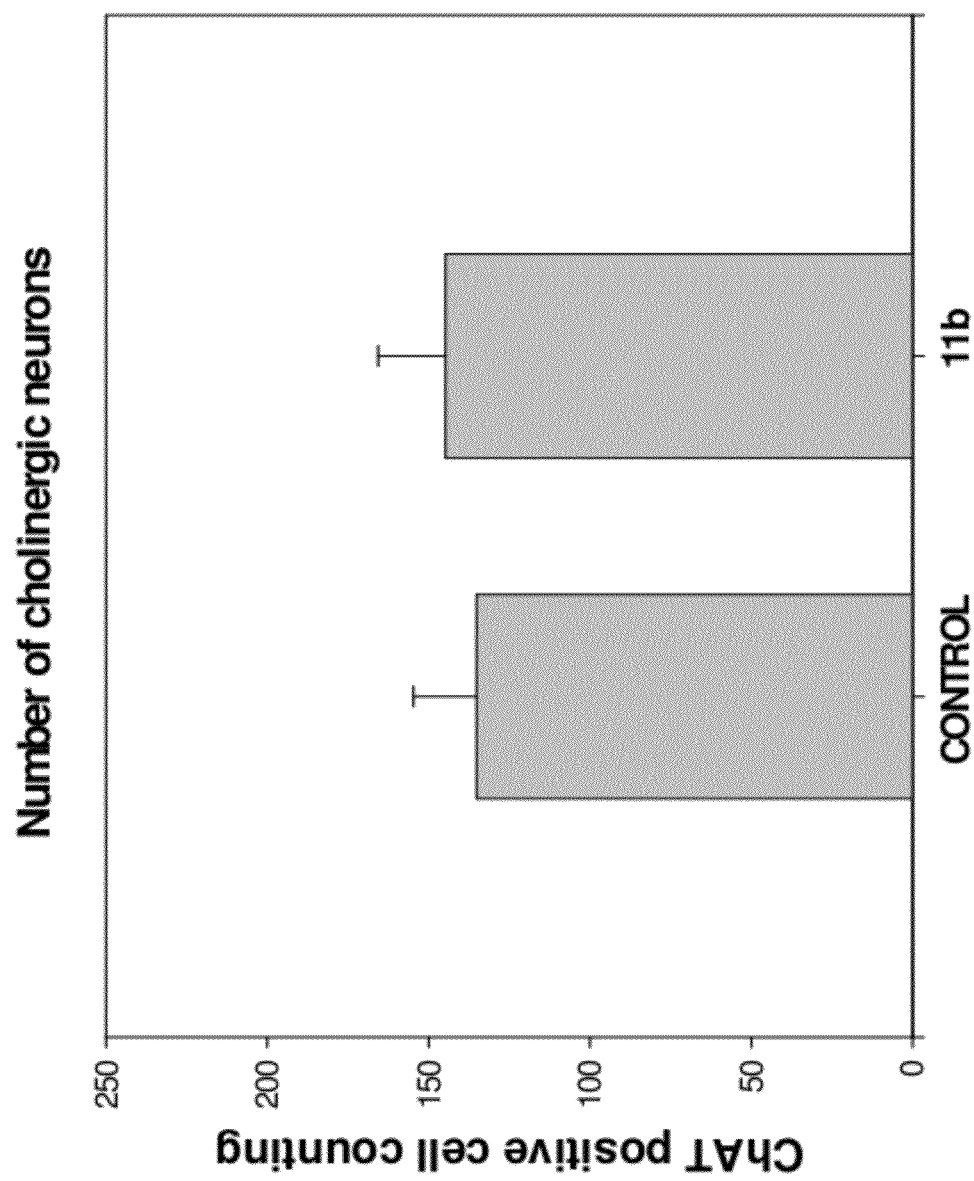
FIG. 15 presents the number of cholinergic neuron in transgenic mice treated with inventive compound.

Ab burden percentages indicates the ratio calculated from comparing with the area of plague with the total area and the result was shown in FIG. 15.

(e). ChAT Antibody Staining

Four tissue sections per mouse were added to PBST to flocculate and then anti-ChAT was added thereto with a ratio of 1:100. The solution was reacted together for overnight at 4° C. and the tissues were washed with PBST. Secondary antibody (HRP conjugated a-goat IgG antibody) was added thereto and mixed together with the mixed ratio of 1:1000 at room temperature one hour before the reaction.

After washing again with PBST, the tissues were stained to brown color with DAB kit as a staining agent. The stained tissues were photographed using by optical microscope connecting with distal camera and then the number of the ChAT positive neuron in the tissues was determined.

As shown in FIG. 15, it has been confirmed that the number of neuron in transgenic mice treated with the compound 18b was slightly increased (See FIG. 15).

Hereinafter, the formulating methods and kinds of excipients will be described, but the present invention is not limited to them. The representative preparation examples were described as follows.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

Hereinafter, the formulating methods and kinds of excipients will be described, but the present invention is not limited to them. The representative preparation examples were described as follows.

| Preparation of powder | |
|---|---|
| Compound (18b) | 20 mg |
| Lactose | 100 mg |
| Talc | 10 mg |

Powder preparation was prepared by mixing above components and filling sealed package.

| Preparation of tablet | |
|---|---|
| Compound (11b) | 10 mg |
| Corn Starch | 100 mg |
| Lactose | 100 mg |
| Magnesium Stearate | 2 mg |

Tablet preparation was prepared by mixing above components and entabletting.

| Preparation of capsule | |
|---|---|
| Compound (18b) | 10 mg |
| Corn starch | 100 mg |
| Lactose | 100 mg |
| Magnesium Stearate | 2 mg |

Tablet preparation was prepared by mixing above components and filling gelatin capsule by conventional gelatin preparation method.

| Preparation of injection | |
|---|---|
| Compound (11b) | 10 mg |
| Distilled water for injection | optimum amount |
| PH controller | optimum amount |

Injection preparation was prepared by dissolving active component, controlling pH to about 7.5 and then filling all the components in 2 ample and sterilizing by conventional injection preparation method.

| Preparation of liquid | |
|---|---|
| Compound (18b) | 20 mg |
| Sugar | 5~10 g |
| Citric acid | 0.05~0.3% |
| Caramel | 0.005~0.02% |
| Vitamin C | 0.1~1% |
| Distilled water | 79~94% |
| $CO_2$ gas | 0.5~0.82% |

Liquid preparation was prepared by dissolving active component, filling all the components and sterilizing by conventional liquid preparation method.

| Preparation of health care food | |
|---|---|
| Compound (11b) | 1000 mg |
| Vitamin mixture | optimum amount |
| Vitamin A acetate | 70 mg |
| Vitamin E | 1.0 mg |
| Vitamin B$_1$ | 0.13 mg |
| Vitamin B$_2$ | 0.15 mg |
| Vitamin B6 | 0.5 mg |
| Vitamin B12 | 0.2 mg |
| Vitamin C | 10 mg |
| Biotin | 10 mg |
| Amide nicotinic acid | 1.7 mg |
| Folic acid | 50 mg |
| Calcium pantothenic acid | 0.5 mg |
| Mineral mixture | optimum amount |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |
| Calcium carbonate | 100 mg |
| Magnesium chloride | 24.8 mg |

The above-mentioned vitamin and mineral mixture may be varied in many ways. Such variations are not to be regarded as a departure from the spirit and scope of the present invention.

| Preparation of health beverage | |
|---|---|
| Compound (18b) | 1000 mg |
| Citric acid | 1000 mg |
| Oligosaccharide | 100 g |
| Apricot concentration | 2 g |
| Taurine | 1 g |
| Distilled water | 900 ml |

Health beverage preparation was prepared by dissolving active component, mixing, stirred at 85□ for 1 hour, filtered and then filling all the components in 1000 ml ample and sterilizing by conventional health beverage preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

As described in the present invention, the novel benzofuran derivatives of the present invention showed potent inhibiting activity of beta-amyloid aggregation and cell cytotoxicity resulting in stimulating the proliferation of neuronal cells as well as recovering activity of memory learning injury caused by neuronal cell injury using transformed animal model with beta-amyloid precursor gene, therefore the compounds can be useful in treating or preventing cognitive function disorder.

The invention claimed is:

1. A compound represented by general formula (I), or a pharmaceutically acceptable salt thereof:

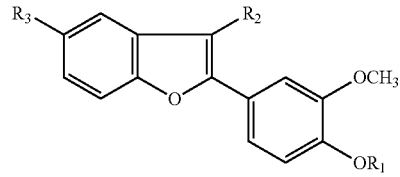

Chemical Formula I wherein

R$_1$ is a hydrogen atom, C$_1$-C$_6$ alkyl group, C$_2$-C$_6$ alkyl ketone group or —(CH$_2$)$_n$-Q, of which Q is an ether group or amine group substituted with C$_1$-C$_6$ lower alkyl group;

R$_2$ is a hydrogen atom, or an ether group or thio group substituted with C$_1$-C$_6$ alkyl group;

R$_3$ is

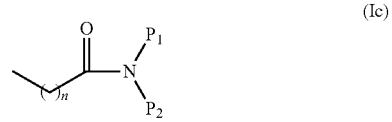

(Ic)

wherein P$_1$, P$_2$ is independently, at least one selected from the group consisting of a hydrogen atom, C$_1$-C$_6$ alkyl group, phenyl group, benzyl group and 2-methyl-3-acetamide group, n is an integer of 0-9.

2. The compound of claim 1, wherein R$_1$ is a methyl group, ethyl group, methylketone group or ethyl ketone group; Q is a methoxy group, an ethoxy group, dimethylamino group or diethylamino group; R$_2$ is a hydrogen atom or methylthio group; R$_3$ is a group of general formula (Ic) wherein P$_1$, P$_2$ is independently a methyl group, an ethyl group, a dimethyl group, a diethyl group or 2-methyl-3-acetamide group.

3. The compound of claim 1, wherein said compound is selected from the group consisting of:

N,N-diethyl 3-[2-(4'-hydroxy-3'-methoxyphenyl)-3-(methylthio)-benzofuran-5-yl]-propionamide, N,N-dimethyl 3-[2-(4'-hydroxy-3'-methoxyphenyl)-3-(methylthio)-benzofuran-5-yl]-propionamide, N-methyl 3-[2-(4'-hydroxy-3'-methoxyphenyl)-3-(methylthio)-benzofuran-5-yl]-propionamide, N,N-diethyl 2-[2-(4'-hydroxy-3'-methoxyphenyl)-3-(methylthio)-benzofuran-5-yl]-acetamide, N,N-dimethyl 2-[2-(4'-hydroxy-3'-methoxyphenyl)-3-(methylthio)-benzofuran-5-yl]-acetamide, N-methyl 2-[2-(4'-hydroxy-3'-methoxyphenyl)-3-(methylthio)-benzofuran-5-yl]-acetamide, (R)-2-(2-(2-(4-hydroxy-3-methoxyphenyl)-3-(methylthio)-benzofuran-5-yl]-acetamide-4-methylpentanamide, N-phenyl 3-[2-(4'-hydroxy-3'-methoxyphenyl)-3-(methylthio)-benzofuran-5-yl]-propionamide, N-benzyl 3-[2-(4'-hydroxy-3'-methoxyphenyl)-3-(methylthio)-benzofuran-5-yl]-propionamide, (R)-3-(2-[2-(4-hydroxy-3-methoxyphenyl)-3-(methylsulfanyl)-1-benzofuran-5-yl]-acetylamino-4-methylpentanamide, N-phenyl 2-[2-(4'-hydroxy-3'-methoxyphenyl)-3-(methylthio)-benzofuran-5-yl]-acetamide,
N-benzyl 2-[2-(4'-hydroxy-3'-methoxyphenyl)-3-(methylthio)-benzofuran-5-yl]-acetamide,
2-[2-(4'-hydroxy-3'-methoxyphenyl)-3-(methylthio)-benzofuran-5-yl]acetamide,
3-[2-(4'-hydroxy-3'-methoxyphenyl)-3-(methylthio)-benzofuran-5-yl]propionamide,
3-(2-(4-Hydroxy-3-methoxyphenyl)-3-(methylthio)benzofuran-5-yl)-N,N-dipropylpropanamide,
3-(2-(3,4-Dimethoxyphenyl)-3-(methylthio)benzofuran-5-yl)-N,N-dipropylpropanamide,
2-(2-(4-Hydroxy-3-methoxyphenyl)-3-(methylthio)benzofuran-5-yl)-N,N-dimethylacetamide,
2-(2-(3,4-Dimethoxyphenyl)-3-(methylthio)benzofuran-5-yl)-N-propylacetamide,
N,N-Diethyl-3-(2-(3,4-dimethoxyphenyl)benzofuran-5-yl)propanamide,
N,N-Diethyl-2-(2-(4-hydroxy-3-methoxyphenyl)benzofuran-5-yl)acetamide,
2-(2-(4-Hydroxy-3-methoxyphenyl)benzofuran-5-yl)-N,N-dipropylacetamide,
N,N-Diethyl-2-(2-(3,4-dimethoxyphenyl)benzofuran-5-yl)acetamide, and
2-(2-(3,4-Dimethoxyphenyl)benzofuran-5-yl)-N,N-dimethylacetamide.

4. A pharmaceutical composition comprising the compound represented by general formula (I) as set forth in claim 1 or the pharmaceutically acceptable salt thereof, together with pharmaceutically acceptable carriers or diluents.

5. A method of treatment comprising administering the compound represented by general formula (I) as set forth in claim 1 or the pharmacologically acceptable carrier thereof; to a human or mammal in need of treatment of a cognitive function disorder selected from the group consisting of Alzheimer type dementia, cerebrovascular type dementia, Creutzfeldt-jakob's disease, and Parkinson's disease.

6. A health care food comprising the compound represented by general formula (I) as set forth in claim 1, or the pharmacologically acceptable salt thereof, together with a sitologically acceptable additive for the alleviation of cognitive function disorder.

7. The health care food of claim 6, the health care food is a form of powder, granule, tablet, capsule or beverage.

8. A method of inhibiting accumulated beta-amyloid in a mammal comprising administering to said mammal the compound represented by general formula (I) as set forth in claim 1 or the pharmacologically acceptable salt thereof, together with a pharmaceutically acceptable carrier thereof.

* * * * *